US008658367B2

(12) United States Patent
Quake et al.

(10) Patent No.: US 8,658,367 B2
(45) Date of Patent: *Feb. 25, 2014

(54) MICROFABRICATED CROSSFLOW DEVICES AND METHODS

(75) Inventors: Stephen R. Quake, Stanford, CA (US); Todd Thorsen, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/475,868

(22) Filed: May 18, 2012

(65) Prior Publication Data

US 2012/0276543 A1 Nov. 1, 2012

Related U.S. Application Data

(63) Continuation of application No. 11/868,942, filed on Oct. 8, 2007, now Pat. No. 8,252,539, which is a continuation of application No. 09/953,103, filed on Sep. 14, 2001, now Pat. No. 7,294,503.

(60) Provisional application No. 60/246,793, filed on Nov. 8, 2000, provisional application No. 60/233,037, filed on Sep. 15, 2000.

(51) Int. Cl.
*C12Q 1/68* (2006.01)
*C12M 1/34* (2006.01)
*G01N 35/08* (2006.01)
*B01F 3/08* (2006.01)

(52) U.S. Cl.
USPC .................. 435/6.12; 435/288.5; 435/288.7; 435/293.1; 436/53; 436/63; 422/82; 422/502; 516/9; 516/20

(58) Field of Classification Search
USPC ....................................... 435/288.5
See application file for complete search history.

(56) References Cited

U.S. PATENT DOCUMENTS

| 2,656,508 A | 8/1949 | Coulter |
| 3,492,399 A | 1/1970 | Prigal |
| 3,570,515 A | 3/1971 | Kinner |
| 3,747,628 A | 7/1973 | Holster et al. |

(Continued)

FOREIGN PATENT DOCUMENTS

| EP | 0 592 094 A2 | 4/1994 |
| EP | 620432 A1 * | 10/1994 |

(Continued)

OTHER PUBLICATIONS

"Biochips," Nature Biotechnology, vol. 18, Supplement 2000, pp. IT43-IT44, 2000.

(Continued)

*Primary Examiner* — William H Beisner
(74) *Attorney, Agent, or Firm* — Kilpatrick Townsend & Stockton LLP

(57) ABSTRACT

A microfluidic device is provided for analyzing or sorting biological materials, such as polynucleotides, polypeptides, proteins, enzymes, viruses and cells. The invention can be used for high throughput or combinatorial screening. The device comprises a main channel and an inlet channel that communicate at a droplet extrusion region so that droplets of solution are deposited into an immiscible solvent in the main channel. Droplets can thereafter be sorted according to biological material detected in each droplet.

27 Claims, 23 Drawing Sheets

(56) References Cited

U.S. PATENT DOCUMENTS

| | | |
|---|---|---|
| 4,046,159 A | 9/1977 | Pegourie |
| 4,119,368 A | 10/1978 | Yamakazi |
| 4,153,855 A | 5/1979 | Feingold |
| 4,245,673 A | 1/1981 | Bouteille et al. |
| 4,373,527 A | 2/1983 | Fischell |
| 4,434,704 A | 3/1984 | Surjaatmadja |
| 4,575,681 A | 3/1986 | Grosso et al. |
| 4,585,209 A | 4/1986 | Aine et al. |
| 4,662,710 A | 5/1987 | ten Berge |
| 4,898,582 A | 2/1990 | Faste |
| 4,959,301 A | 9/1990 | Weaver et al. |
| 4,992,312 A | 2/1991 | Frisch |
| 5,085,562 A | 2/1992 | Van Lintel |
| 5,088,515 A | 2/1992 | Kamen |
| 5,096,388 A | 3/1992 | Weinberg |
| 5,126,115 A | 6/1992 | Fujita et al. |
| 5,164,558 A | 11/1992 | Huff et al. |
| 5,171,132 A | 12/1992 | Miyazaki |
| 5,224,843 A | 7/1993 | Van Lintel |
| 5,259,737 A | 11/1993 | Kamisuki et al. |
| 5,265,327 A | 11/1993 | Faris et al. |
| 5,290,240 A | 3/1994 | Horres, Jr. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom |
| 5,400,741 A | 3/1995 | DeTitta et al. |
| 5,417,235 A | 5/1995 | Wise et al. |
| 5,423,287 A | 6/1995 | Usami et al. |
| 5,452,878 A | 9/1995 | Gravesen et al. |
| 5,454,472 A | 10/1995 | Benecke et al. |
| 5,529,465 A | 6/1996 | Zengerle et al. |
| 5,574,893 A | 11/1996 | Southgate et al. |
| 5,593,130 A | 1/1997 | Hansson et al. |
| 5,642,015 A | 6/1997 | Whitehead et al. |
| 5,656,155 A | 8/1997 | Norcross et al. |
| 5,659,171 A | 8/1997 | Young et al. |
| 5,660,370 A | 8/1997 | Webster |
| 5,661,222 A | 8/1997 | Hare |
| 5,665,070 A | 9/1997 | McPhee |
| 5,681,024 A | 10/1997 | Lisec et al. |
| 5,705,018 A | 1/1998 | Hartley |
| 5,759,014 A | 6/1998 | Van Lintel |
| 5,775,371 A | 7/1998 | Pan et al. |
| 5,788,468 A | 8/1998 | Dewa et al. |
| 5,830,663 A | 11/1998 | Embleton et al. |
| 5,836,750 A | 11/1998 | Cabuz |
| 5,842,787 A | 12/1998 | Kopf-Sill et al. |
| 5,854,684 A | 12/1998 | Stabile et al. |
| 5,875,817 A | 3/1999 | Carter |
| 5,876,187 A | 3/1999 | Afromowitz |
| 5,932,799 A | 8/1999 | Moles |
| 5,942,443 A | 8/1999 | Parce et al. |
| 5,958,203 A | 9/1999 | Parce et al. |
| 5,997,961 A | 12/1999 | Feng et al. |
| 6,007,309 A | 12/1999 | Hartley |
| 6,043,080 A | 3/2000 | Lipshutz et al. |
| 6,123,769 A | 9/2000 | Sanjoh |
| 6,155,282 A | 12/2000 | Zachary et al. |
| 6,174,365 B1 | 1/2001 | Sanjoh |
| 6,221,654 B1 | 4/2001 | Quake et al. |
| 6,246,330 B1 | 6/2001 | Nielsen |
| 6,258,858 B1 | 7/2001 | Nakajima et al. |
| 6,296,673 B1 | 10/2001 | Santarsiero et al. |
| 6,329,209 B1 | 12/2001 | Wagner et al. |
| 6,345,502 B1 | 2/2002 | Tai et al. |
| 6,358,387 B1 | 3/2002 | Kopf-Sill et al. |
| 6,375,871 B1 | 4/2002 | Bentsen et al. |
| 6,376,971 B1 | 4/2002 | Petrine et al. |
| 6,409,832 B2 | 6/2002 | Weigl et al. |
| 6,488,832 B2 | 12/2002 | Heller |
| 6,488,872 B1 | 12/2002 | Beebe et al. |
| 6,520,936 B1 | 2/2003 | Mann |
| 6,540,895 B1 | 4/2003 | Spence et al. |
| 6,541,071 B1 | 4/2003 | Bookbinder et al. |
| 6,667,124 B2 | 12/2003 | Suenaga et al. |
| 6,689,473 B2 | 2/2004 | Guire et al. |
| 6,713,327 B2 | 3/2004 | Leedy |
| 6,716,378 B2 | 4/2004 | Yang et al. |
| 6,765,279 B2 | 7/2004 | Leedy |
| 6,767,706 B2 | 7/2004 | Quake et al. |
| 6,829,753 B2 | 12/2004 | Lee et al. |
| 6,847,153 B1 | 1/2005 | Balizer |
| 6,866,785 B2 | 3/2005 | Zare et al. |
| 6,884,346 B2 | 4/2005 | Zare et al. |
| 6,885,982 B2 | 4/2005 | Harris et al. |
| 6,951,632 B2 | 10/2005 | Unger et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Dam et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 * | 11/2007 | Quake et al. ............... 435/288.5 |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 4,565,026 A1 | 8/2010 | Hansen et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 8,252,539 B2 * | 8/2012 | Quake et al. ............... 435/6.12 |
| 2001/0027745 A1 | 10/2001 | Weigl et al. |
| 2001/0048637 A1 | 12/2001 | Weigl et al. |
| 2002/0014673 A1 | 2/2002 | Leedy |
| 2002/0037499 A1 | 3/2002 | Quake et al. |
| 2002/0045297 A1 | 4/2002 | Leedy |
| 2002/0108096 A1 | 8/2002 | Lee et al. |
| 2003/0080442 A1 | 5/2003 | Unger |
| 2004/0180377 A1 | 9/2004 | Manger et al. |
| 2004/0248167 A1 | 12/2004 | Quake et al. |
| 2005/0053952 A1 | 3/2005 | Hong et al. |
| 2005/0065735 A1 | 3/2005 | Lee et al. |
| 2006/0172408 A1 | 8/2006 | Quake et al. |
| 2006/0281183 A1 | 12/2006 | Sun et al. |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde |
| 2009/0035838 A1 | 2/2009 | Quake et al. |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0239308 A1 | 9/2009 | Dube et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |

(56) References Cited

U.S. PATENT DOCUMENTS

| | | |
|---|---|---|
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |

FOREIGN PATENT DOCUMENTS

| | | |
|---|---|---|
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| EP | 1 065 378 A2 | 1/2001 |
| GB | 2 097 692 A | 11/1982 |
| GB | 2 155 152 A | 9/1985 |
| GB | 2 308 460 A | 6/1997 |
| WO | WO 84/02000 A1 | 5/1984 |
| WO | WO 98/07069 A1 | 2/1998 |
| WO | WO 98/52691 A1 | 11/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 99/61888 A2 | 10/1999 |
| WO | WO 00/00678 A1 | 1/2000 |
| WO | WO 00/43748 A1 | 7/2000 |
| WO | WO 00/60345 A1 | 10/2000 |
| WO | WO 01/06529 A1 | 1/2001 |
| WO | WO 01/06575 A1 | 1/2001 |
| WO | WO 01/09595 A2 | 2/2001 |
| WO | WO 01/09595 A3 | 2/2001 |
| WO | 01/67369 A2 | 9/2001 |
| WO | WO 02/082047 A2 | 10/2002 |
| WO | 2007/033385 A2 | 3/2007 |
| WO | 2007/044091 A2 | 4/2007 |
| WO | 2008/043046 A2 | 4/2008 |
| WO | 2009/100449 A1 | 8/2009 |
| WO | 2010/011852 A1 | 1/2010 |
| WO | 2010/017210 A1 | 2/2010 |
| WO | 2010/077618 A1 | 7/2010 |

OTHER PUBLICATIONS

"Chapter 9: Microfluidic Devices," Micromachined Transducers Sourcebook, pp. 779-882, 1998.

"Last Chance for Micromachines," The Economist Technology Quarterly, 8 pages, Dec. 7, 2000.

Ahn, Chong H. et al., "Fluid Micropumps Based on Rotary Magnetic Actuators," Proceedings of 1995 IEEE Micro Electro Mechanical Systems Workshop (MEMS '95), Amsterdam, Netherlands, pp. 408-412, Jan. 29-Feb. 2, 1995.

Anderson, Janelle R. et al., "Fabrication of Topologically Complex Three-Dimensional Microfluidic Systems in PDMS by Rapid Prototyping," Analytical Chemistry, vol. 72, No. 14, pp. 3158-3164, Jul. 15, 2000.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits by PDMS Elastomer Micromachining," IEEE Int. Conf. Micro Electro Mech. Syst. Tech. Digest, vol. 12, pp. 222-227, 1999.

Ballantyne, J. P. et al., "Selective Area Metallization by Electron-Beam Controlled Direct Metallic Deposition," J. Vac. Sci. Technol., vol. 10, No. 6, pp. 1094-1097, Nov. 1973.

Ashkin, A. et al., "Optical Trapping and Manipulation of Single Cells Using Infrared Laser Beams," Nature, vol. 330, No. 24, pp. 769-771, Dec. 31, 1987.

Ashkin, A. et al., "Optical Trapping and Manipulation of Viruses and Bacteria," Science, vol. 235, pp. 1517-1520, Mar. 20, 1987.

Beebe et al., "Physics and Applications of Microfluidics in Biology," Ann. Rev. Biomed. Eng., 4:261-286 (2002).

Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.

Bloomstein, T. M. et al., "Laser-Chemical Three-Dimensional Writing for Microelectromechanics and Application to Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Brechtel, R. et al., "Control of the Electroosmotic Flow by Metal-Salt-Containing Buffers," Journal of Chromatography A, vol. 716, pp. 97-105, 1995.

Bryzek, Janusz et al., "Micromachines on the March", IEEE Spectrum, vol. 31, No. 5, pp. 20-31, May 1994.

Buchaillot, Lionel et al., "Silicon Nitride Thin Films Young's Modulus Determination by an Optical Non Destructive Method," Jpn. J. Appl. Phys., vol. 36, Part 2, No. 6B, pp. L794-L797, Jun. 15, 1997.

Buican, Tudor N. et al., "Automated Single-Cell Manipulation and Sorting by Light Trapping," Applied Optics, vol. 26, No. 24, pp. 5311-5316, Dec. 15, 1987.

Calkins, Kathryn, "Mycometrix: Rubber Chips," BioCentury, 2 pages, Oct. 16, 2000.

Chan, Jason H. et al., "Microfabricated Polymer Devices for Automated Sample Delivery of Peptides for Analysis by Electrospray Ionization Tandem Mass Spectrometry," Analytical Chemistry, vol. 71, No. 20, pp. 4437-4444, Oct. 15, 1999.

Chiang, Yuh-Min et al., "Characterizing the Process of Cast Molding Microfluidic Systems," SPIE, vol. 3877, pp. 303-311, Sep. 1999.

Chiu, Daniel T. et al., "Patterned Deposition of Cells and Proteins Onto Surfaces by Using Three-Dimensional Microfluidic Systems," PNAS, vol. 97, No. 6, pp. 2408-2413, Mar. 14, 2000.

Chou et al. "A microfabricated device for sizing and sorting DNA molecules", Applied Physical Sciences, Biophysics, Proc. Natl. Acad. Sci, 1999, pp. 11-13, vol. 96, U.S.A.

Chou, Hou-Pu et al., "A Microfabricated Rotary Pump," Biomedical Microdevices, vol. 3, No. 4, pp. 323-330, 2001.

Chou, Hou-Pu et al., "Integrated Elastomer Fluidic Lab-On-A-Chip-Surface Patterning and DNA Diagnostics," Proceedings of the Solid State Actuator and Sensor Workshop, Hilton Head, South Carolina, 4 pages, 2000.

Chou, Hou-Pu et al., "Multiple Disease Diagnostics on a Single Chip," Biophysics Lab, Caltech, pp. 1-4, Mar. 1, 2000.

Crosland-Taylor, P. J., "A Device for Counting Small Particles Suspended in a Fluid Through a Tube," Nature, vol. 171, pp. 37-38, Jan. 3, 1953.

Delamarche, Emmanuel et al., "Patterned Delivery of Immunoglobulins to Surfaces Using Microfluidic Networks," Science, vol. 276, pp. 779-781, May 2, 1997.

Dharmatilleke, Saman et al., "Three-Dimensional Silicone Device Fabrication and Interconnection Scheme for Microfluidic Applications Using Sacrificial Wax Layers," Micro-Electro-Mechanical Systems (MEMS), vol. 2, pp. 413-418, 2000.

Duffy, David C. et al., "Patterning Electroluminescent Materials With Feature Sizes as Small as 5 μm Using Elastomeric Membranes As Masks for Dry Lift-Off," Advanced Materials, vol. 11, No. 7, pp. 546-552, 1999.

Duffy, David C. et al., "Rapid Prototyping of Microfluidic Switches in Poly(dimethyl siloxane) and Their Actuation by Electro-Osmotic Flow," J. Micromech. Microeng., vol. 9, pp. 211-217, 1999.

(56) References Cited

OTHER PUBLICATIONS

Duffy, David C. et al., "Rapid Prototyping of Microfluidic Systems in Poly(dimethylsiloxane)," Analytical Chemistry, vol. 70, No. 23, pp. 4974-4984, Dec. 1, 1998.
Effenhauser, Carlo S. et al., "Integrated Capillary Electrophoresis on Flexible Silicone Microdevices: Analysis of DNA Restriction Fragments and Detection of Single DNA Molecules on Microchips," Analytical Chemistry, vol. 69, No. 17, pp. 3451-3457, Sep. 1, 1997.
Effenhauser, Carlo S. et al., "Integrated Chip-Based Capillary Electrophoresis," Electrophoresis, vol. 18, pp. 2203-2213, 1997.
Ericson, Christer et al., "Electroosmosis- and Pressure-Driven Chromatography in Chips Using Continuous Beds," Analytical Chemistry, vol. 72, No. 1, pp. 81-87, Jan. 1, 2000.
Fahrenberg, J. et al., "A Microvalve System Fabricated by Thermoplastic Molding," J. Micromech. Microeng., vol. 5, pp. 169-171, 1995.
Fettinger, J. C. et al., "Stacked Modules for Micro Flow Systems in Chemical Analysis: Concept and Studies Using an Enlarged Model," Sensors and Actuators B, vol. 17, pp. 19-25, 1993.
Fiedler, Stefan et al., "Dielectrophoretic Sorting of Particles and Cells in a Microsystem," Analytical Chemistry, vol. 70, No. 9, pp. 1909-1915, May 1, 1998.
Figeys, Daniel et al., "An Integrated Microfluidics-Tandem Mass Spectrometry System for Automated Protein Analysis," Analytical Chemistry, vol. 70, No. 18, pp. 3728-3734, Sep. 15, 1998.
Figeys, Daniel et al., "Nanoflow Solvent Gradient Delivery From a Microfabricated Device for Protein Identifications by Electrospray Ionization Mass Spectrometry," Analytical Chemistry, vol. 70, No. 18, pp. 3721-3727, Sep. 15, 1998.
Folch, A. et al., "Molding of Deep Polydimethylsiloxane Microstructures for Microfluidics and Biological Applications," Journal of Biomechanical Engineering, vol. 121, pp. 28-34, Feb. 1999.
Fu, Anne Y. et al., "A Microfabricated Fluorescence-Activated Cell-Sorter," Nature Biotechnology, vol. 17, pp. 1109-1111, Nov. 1999.
Fulwyler, M. J., "Electronic Separation of Biological Cells by Volume," Science, pp. 910-911, Nov. 1, 1965.
Galambos, Paul et al., "Electrical and Fluidic Packaging of Surface Micromachined Electro-Microfluidic Devices," 8 pages.
Gao, Jun et al., "Integrated Microfluidic System Enabling Protein Digestion, Peptide Separation, and Protein Identification," Analytical Chemistry, vol. 73, No. 11, pp. 2648-2655, Jun. 1, 2001.
Gass, V. et al., "Integrated Flow-Regulated Silicon Micropump," Sensors and Actuators A, vol. 43, pp. 335-338, 1994.
Gerlach, Torsten, "Pumping Gases by a Silicon Micro Pump With Dynamic Passive Valves," Transducers '97, 1997 International Conference on Solid-State Sensors and Actuators, Chicago, Illinois, pp. 357-360, Jun. 16-19, 1997.
Goll, C. et al., "Microvalves With Bistable Buckled Polymer Diaphragms," J. Micromech. Microeng., vol. 6, pp. 77-79, 1996.
Gravesen, Peter et al., "Microfluidics-A Review," J. Micromech. Microeng., vol. 3, pp. 168-192, 1993.
Greene, Chana, "Characterizing the Properties of PDMS," pp. 1-11, Summer 2000.
Guérin, L. J. et al., "Simple and Low Cost Fabrication of Embedded Micro-Channels by Using a New Thick-Film Photoplastic," Transducers '97, 1997 International Conference on Solid-State Sensors and Actuators, Chicago, Illinois, pp. 1419-1422, Jun. 18-19, 1997.
Harrison et al., "Micromachining a miniaturized capillary electrophoresis-based chemical analysis system on a chip," Science, (Aug. 13, 1993) vol. 261, PD. 895-897.
Henion, Jack et al., "Capillary Electrophoresis/Mass Spectrometry: From One Meter Capillaries to Chip-Based Devices," 2 pages, 1999.
Hicks, Jennifer, "Genetics and Drug Discovery Dominate Microarray Research," R&D Magazine, pp. 28-33, Feb. 1999.
Hofmann, Oliver et al., "Modular Approach to Fabrication of Three-Dimensional Microchannel Systems in PDMS—Application to Sheath Flow Microchips," Lab on a Chip, vol. 1, pp. 108-114, 2001.
Hopfgartner, Gerard et al., "Exact Mass Measurement of Product Ions for the Structural Elucidation of Drug Metabolites With a Tandem Quadrupole Orthogonal-Acceleration Time-Of-Flight Mass Spectrometer," Journal of the American Society for Mass Spectrometry, vol. 10, pp. cover, 1305-1314, Dec. 1999.
Horn, Howard, "Lab Chips Sector: Microtechnologies Are Changing Healthcare and More," Life Sciences, pp. 19-21, Mar. 20, 2001.
Hornbeck, Larry J. et al., "Bistable Deformable Mirror Device," Spatial Light Modulators and Applications 1988 Technical Digest Series, vol. 8, Postconference Edition, pp. cover, 107-110, Jun. 15-17, 1988.
Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.
Hosokawa, Kazuo et al., "Handling of Picoliter Liquid Samples in a Poly(dimethylsiloxane)-Based Microfluidic Device," Analytical Chemistry, vol. 71, No. 20, pp. 4781-4785, Oct. 15, 1999.
Ikuta, Koji et al., "Three Dimensional Micro Integrated Fluid Systems (MIFS) Fabricated by Stereo Lithography," IEEE, pp. 1-6, 1994.
Jacobson, Stephen C. et al., "High-Speed Separations on a Microchip," Analytical Chemistry, vol. 66, No. 7, pp. 1114-1118, Apr. 1, 1994.
Jacobson, Stephen C. et al., "Microfluidic Devices for Electrokinetically Driven Parallel and Serial Mixing," Analytical Chemistry, vol. 71, No. 20, pp. 4455-4459, Oct. 15, 1999.
Jerman, Hal, "Electrically-Activated, Normally-Closed Diaphragm Valves," Transducers '91, 1991 International Conference on Solid-State Sensors and Actuators, pp. cover, 1045-1048, 1991.
Jo, Byung-Ho et al., "Fabrication of Three-Dimensional Microfluidic Systems by Stacking Molded Polydimethylsiloxane (PDMS) Layers" SPIE, vol. 3877, pp. 222-229, Sep. 1999.
Jo, Byung-Ho et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.
Jung, D. R. et al., "Chemical and Physical Interactions At Metal/Self-Assembled Organic Monolayer Interfaces," pp. 1-54, 1994.
Kagan, C. R., "Organic-Inorganic Hybrid Materials As Semiconducting Channels in Thin-Film Field-Effect Transistors," Science, vol. 286, pp. 945-947, Oct. 29, 1999.
Kapur, Ravi et al., "Fabrication and Selective Surface Modification of 3-Dimensionally Textured Biomedical Polymers From Etched Silicon Substrates," Journal of Biomedical Materials Research, vol. 33, pp. 205-216, 1996.
Kawano, Yasushi et al., "Rapid Isolation and Identification of *Staphylococcal* Exoproteins by Reverse Phase Capillary High Performance Liquid Chromatography-Electrospray Ionization Mass Spectrometry," FEMS Microbiology Letters, vol. 189, pp. 103-108, 2000.
Kamentsky, Louis A. et al., "Spectrophotometer: New Instrument for Ultrarapid Cell Analuysis," Science, vol. 150, pp. 630-631, Oct. 29, 1965.
Kenis, Paul J. A. et al., "Microfabrication Inside Capillaries Using Multiphase Laminar Flow Patterning," Science, vol. 285, pp. 83-85, Jul. 2, 1999.
Khoo, Melvin et al., "A Novel Micromachined Magnetic Membrane Microfluid Pump," pp. 1-4.
Kim, Enoch et al., "Micromolding in Capillaries: Applications in Materials Science," J. Am. Chem. Soc., vol. 118, No. 24, pp. 5722-5731, 1996.
Kim, Enoch et al., "Polymer Microstructures Formed by Moulding in Capillaries," Nature, vol. 376, pp. 581-584, Aug. 17, 1995.
Kirk-Othmer, "Concise Encyclopedia of Chemical Technology," John Wiley & Sons, 5 pages.
Kopp et al. "Chemical Amplification: Continuous-Flow PCR on a Chip", Science, 1998,280:1046-1048.
Kuhn, Lawrence et al., "Silicon Charge Electrode Array for Ink Jet Printing," IEEE Transactions on Electron Devices, vol. ED-25, No. 10, pp. 1257-1260, Oct. 1978.
Kumar, Amit et al., "Features of Gold Having Micrometer to Centimeter Dimensions Can Be Formed Through a Combination of Stamping With an Elastomeric Stamp and an Alkanethiol 'Ink' Followed by Chemical Etching," Appl. Phys. Lett., vol. 63, No. 14, pp. 2002-2004, Oct. 4, 1993.

(56) References Cited

OTHER PUBLICATIONS

Kumar, Amit et al., "Patterning Self-Assembled Monolayers: Applications in Materials Science," Langmuir, vol. 10, pp. 1498-1511, 1994.
Lagally, Eric T. et al., "Fully Integrated PCR-Capillary Electrophoresis Microsystem for DNA Analysis," Lab on a Chip, vol. 1, pp. 102-107, 2001.
Lagally, Eric T. et al., "Monolithic Integrated Microfluidic DNA Amplification and Capillary Electrophoresis Analysis System," Sensors and Actuators B, vol. 63, pp. 138-146, 2000.
Lagally, E. T. et al., "Single-Molecule DNA Amplification and Analysis in an Integrated Microfluidic Device," Analytical Chemistry, vol. 73, No. 3, pp. 565-570, Feb. 1, 2001.
Lammerink, T. S. J. et al., "Modular Concept for Fluid Handling Systems," IEEE, pp. 389-394, 1996.
Lazar, Iulia M. et al., "Novel Microfabricated Device for Electrokinetically Induced Pressure Flow and Electrospray Ionization Mass Spectrometry," Journal of Chromatography A, vol. 892, pp. 195-201, 2000.
Li, Jianjun et al., "Integration of Microfabricated Devices to Capillary Electrophoresis-Electrospray Mass Spectrometry Using a Low Dead Volume Connection: Application to Rapid Analyses of Proteolytic Digests," Analytical Chemistry, vol. 71, No. 15, pp. 3036-3045, Aug. 1, 1999.
Li, Paul C. H. et al., "Transport, Manipulation, and Reaction of Biological Cells On-Chip Using Electrokinetic Effects," Analytical Chemistry, vol. 69, No. 8, pp. 1564-1568, Apr. 15, 1997.
Licklider, Larry et al., "A Micromachined Chip-Based Electrospray Source for Mass Spectrometry," Analytical Chemistry, vol. 72, No. 2, pp. 367-375, Jan. 15, 2000.
Lin, L. Y. et al., "Free-Space Micromachined Optical Switches for Optical Networking," IEEE Journal of Selected Topics in Quantum Electronics, vol. 5, No. 1, pp. 4-9, Jan. 1999.
Lin, Yuehe et al., "Laser Micromachined Isoelectric Focusing Device on Polymer Substrate for Electrospray Mass Spectrometry," SPIE, vol. 3877, pp. 28-35, Sep. 1999.
Liu, Hanghui et al., "Development of Multichannel Devices With an Array of Electrospray Tips for High-Throughput Mass Spectrometry," Analytical Chemistry, vol. 72, No. 14, pp. 3303-3310, Jul. 15, 2000.
Lötters, J C et al., "The Mechanical Properties of the Rubber Elastic Polymer Polydimethylsiloxane for Sensor Applications," J. Micromech. Microeng., vol. 7, pp. 145-147, 1997.
Lucy, Charles A. et al., "Characterization of the Cationic Surfactant Induced Reversal of Electroosmotic Flow in Capillary Electrophoresis," Anal. Chem., vol. 68, pp. 300-305, 1996.
Maluf, N., "An Introduction to Microelectromechanical Systems Engineering," Artech House Publishers, Boston London, pp. 42-45, Dec. 1999.
Manz, A. et al., "Micromachining of Monocrystalline Silicon and Glass for Chemical Analysis Systems," Trends in Analytical Chemistry, vol. 10, No. 5, pp. 144-149, 1991.
Marshall, Sid, "Fundamental Changes Ahead for Lab Instrumentation," R&D Magazine, 5 pages, Feb. 1999.
Marsili, Ray, "Lab-On-A-Chip Poised to Revolutionize Sample Prep," R&D Magazine, 5 pages, Feb. 1999.
Mason et al., "Shear Rupturing of Droplets in Complex Fluids," Langmuir, 13, 4600-4613 (1997).
McDonald, J. Cooper et al., "Fabrication of Microfluidic Systems in Poly(dimethylsiloxane)," Electrophoresis, vol. 21, pp. 27-40, 2000.
Moldavan, Andrew, "Scientific Apparatus and Laboratory Methods: Photo-Electric Technique for the Counting of Microscopical Cells," Science, vol. 80, No. 2069, pp. 188-189, Aug. 24, 1934.
Muller, Richard S. et al., "Surface-Micromachined Microoptical Elements and Systems," Proceedings of the IEEE, vol. 86, No. 8, pp. 1705-1720, Aug. 1998.
New Objective, Inc., "What Is Electrospray," www.newobjective.com/electrospray/electrospray.html, 4 pages, 1999.
Oleschuk, Richard D. et al., "Analytical Microdevices for Mass Spectrometry," Trends in Analytical Chemistry, vol. 19, No. 6., pp. 379-388, 2000.
Olsson, Anders et al., "Simulation Studies of Diffuser and Nozzle Elements for Valve-Less Micropumps," Transducers '97, 1997 International Conference on Solid-State Sensors and Actuators, Chicago, Illinois, pp. 1039-1042, Jun. 16-19, 1997.
Pethig, Ronald et al., "Applications of Dielectrophoresis in Biotechnology," Tibtech, vol. 15, pp. 426-432, Oct. 1997.
Protana website, "NanoES Products," www.protana.com/products/default.asp, 3 pages, Sep. 19, 2000.
Qin, Dong et al., "Elastomeric Light Valves," Adv. Mater., vol. 9, No. 5, pp. 407-410, 1997.
Qin, Dong et al., "Photolithography With Transparent Reflective Photomasks," J. Vac. Sci. Technol. B, vol. 16, No. 1, pp. 98-103, Jan. 1998.
Quake, Stephen R. et al., "From Micro- to Nanofabrication With Soft Materials," Science, vol. 290, pp. 1536-1540, Nov. 24, 2000.
Rapp, R. et al., "LIGA Micropump for Gases and Liquids," Sensors and Actuators A, vol. 40, pp. 57-61, Jan. 1994.
Roylance, Lynn Michelle et al., "A Batch-Fabricated Silicon Accelerometer," IEEE Transactions on Electron Devices, vol. ED-26, No. 12, pp. 1911-1917, Dec. 1979.
Sandia National Laboratories, "Electro Microfluidic Dual In-Line Package (EMDIP)," 2 pages.
Sanjoh, Akira et al., "Spatiotemporal Protein Crystal Growth Studies Using Microfluidic Silicon Devices," Journal of Crystal Growth, vol. 196, pp. 691-702, 1999.
Schasfoort, Richard B. M. et al., "Field-Effect Flow Control for Microfabricated Fluidic Networks," Science, vol. 286, pp. 942-945, Oct. 29, 1999.
Schomburg, W. K. et al., "Fabrication of Polymer Microcomponents With the AMANDA-Process," New Materials and Directions, Eurosensors XII, pp. 711-714, Sep. 13-16, 1998.
Schueller, Olivier J. A. et al., "Fabrication of Glassy Carbon Microstructures by Soft Lithography," Sensors and Actuators A, vol. 72, pp. 126-139, 1999.
Shevchenko, Andrej et al., "Rapid 'de Novo' Peptide Sequencing by a Combination of Nanoelectospray, Isotopic Labeling and a Quadrupole/Time-Of-Flight Mass Spectometer," Rapid Communications in Mass Spectrometry, vol. 11, pp. 1015-1024, 1997.
Shinohara, Jun et al., "A High Pressure-Resistance Micropump Using Active and Normally-Closed Valves," IEEE, pp. 86-91, 2000.
Shoji, Shuichi, "Fluids for Sensor Systems," Topics in Current Chemistry, vol. 194, pp. 163-188, 1998.
Shoji, Shuichi et al., "Smallest Dead Volume Microvalves for Integrated Chemical Analyzing Systems," Transducers '91, 1991 International Conference on Solid-State Sensors and Actuators, San Francisco, California, pp. cover, 1052-1055, 1991.
Smits, J.G., "Piezoelectric Micropump With Three Valves Working Peristaltically," Sensors and Actuators, vol. A21-A23, pp. 203-206, 1990.
Sohn, L. L. et al., "Capacitance Cytometry: Measuring Biological Cells One by One," PNAS, vol. 97, No. 20, pp. 10687-10690, Sep. 26, 2000.
Squires et al., "Microfluidics: Fluid physics at the nanoliter scale," Reviews of Modern Physics, 77(3):977-1026 (2005).
Stone et al., "Engineering Flows in Small Devices: Microfluidics Toward a Lab-on-a-Chip," Ann. Rev. Fluid Mech., 36:381-411 and C1-C4 (2004).
Sugiura et al., "Preparation of Monodispersed Solid Lipid Microspheres Using a Microchannel Emulsification Technique," J. Colloid Interface Science, 227:95-103 (2000).
Sugiura et al., "Interfacial Tension Driven Monodispersed Droplet Formation from Microfabricated Channel Array," Langmuir, 17:5562-5566 (2001).
Tawfik, Dan S. et al., "Man-Made Cell-Like Compartments for Molecular Evolution," Nature Biotechnology, vol. 16, pp. 652-656, Jul. 1998.
Thompson, L. F. et al., "Introduction to Microlithography," 185th Meeting of the American Chemical Society, Seattle, WA, pp. 2 cover pp. 1-13, Mar. 20-25, 1983.

(56) References Cited

OTHER PUBLICATIONS

Thorsen, Todd et al., "Dynamic Pattern Formation in a Vesicle-Generating Microfluidic Device," Physical Review Letters, vol. 86, No. 18, pp. 4163-4166, Apr. 30, 2001.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Industrial Chemistry, Sections 6 to 6.3, Topic: Carbon Black, Sixth Edition, 7 pages, 1999.

Umdanhowar et al., "Monodisperse Emulsion Generation via Drop Break Off in a Coflowing Stream," Langmuir, 16, 347-351.

Unger, Marc A. et al., "Monolithic Microfabricated Valves and Pumps by Multilayer Soft Lithography," Science, vol. 288, pp. 113-116, Apr. 7, 2000.

Van De Pol, F.C.M. et al., "A Thermo-Pneumatic Actuation Principle for a Microminiature Pump and Other Micromechanical Devices," Sensors and Actuators, vol. 17, Nos. 1-2, pp. 139-143, May 3, 1989.

Van De Pol, F.C.M. et al., "Micro Liquid Handling Devices—A Review," Micro Systems Technologies, vol. 90, pp. 799-805, 1990.

Van Den Berg, A. et al., "Micro Total Analysis Systems," Proceedings of the μTAS '94 Workshop, University of Twente, The Netherlands, 17 pages, Nov. 21-22, 1994.

Van Dilla, M. A. et al., "Cell Microfluorometry: A Method for Rapid Fluorescence Measurement," Science, vol. 163, pp. 1213-1214, Mar. 14, 1969.

Verpoorte, Elisabeth M. J. et al., "Three-Dimensional Micro Flow Manifolds for Miniaturized Chemical Analysis Systems," J. Micromech. Microeng., vol. 7, pp. 246-256, 1994.

Vieider, Christian et al., "A Pneumatically Actuated Micro Valve With a Silicon Rubber Membrane for Integration With Fluid Handling Systems," Transducers '95, 8th International Conference on Solid-State Sensors and Actuators and Eurosensors IX, Stockholm, Sweden, pp. 284-286, Jun. 25-29, 1995.

Washizu, Masao et al., "Molecular Dielectrophoresis of Biopolymers," IEEE Transactions on Industry Applications, vol. 30, No. 4, pp. 835-843, Jul. 1994.

Weigl, Bernhard H., "Microfluidics-Based Lab-On-A-Chip Systems," IVD Technology Magazine, 8 pages, Nov./Dec. 2000.

Whitesides, George M. et al., "Flexible Methods for Microfluidics," Physics Today, pp. 42-48, Jun. 2001.

Wilbur, James L. et al., "Lithographic Molding: A Convenient Route to Structures With Sub-Micrometer Dimensions," Adv. Mater., vol. 7, No. 7, pp. 649-652, 1995.

Whitesides, George M. et al., "Soft Lithography," Angewandte Chemie International Edition 37, 551-575, 1998.

Wilm, Matthias et al., "Femtomole Sequencing of Proteins From Polyacrylamide Gels by Nano-Electrospray Mass Spectrometry," Nature, vol. 379, pp. 466-469, Feb. 1, 1996.

Xia, Younan et al., "Complex Optical Surfaces Formed by Replica Molding Against Elastomeric Masters," Science, vol. 273, pp. 347-349, Jul. 19, 1996.

Xia, Younan et al., "Micromolding of Polymers in Capillaries: Applications in Microfabrication," Chem. Mater., vol. 8, No. 7, pp. 1559-1566, 1996.

Xia, Younan et al., "Reduction in the Size of Features of Patterned SAMs Generated by Microcontact Printing With Mechanical Compression of the Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures by Soft Lithography," Adv. Mater., vol. 11, No. 14, pp. 1186-1189, 1999.

Xu, Jingdong et al., "Room-Temperature Imprinting Method for Plastic Microchannel Fabrication," Analytical Chemistry, vol. 72, No. 8, pp. 1930-1933, Apr. 15, 2000.

Xue, Qifeng et al., "Integrated Multichannel Microchip Electrospray Ionization Mass Spectrometry: Analysis of Peptides From On-Chip Tryptic Digestion of Melittin," Rapid Communications in Mass Spectrometry, vol. 11, 1253-1256, 1997.

Xue, Qifeng et al., "Multichannel Microchip Electrospray Mass Spectrometry," Analytical Chemistry, vol. 69, No. 3, pp. 426-430, Feb. 1, 1997.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Young, A. M. et al., "Contoured Elastic-Membrane Microvalves for Microfluidic Network Integration," Journal of Biomechanical Engineering, vol. 121, pp. 2-6, Feb. 1999.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation of Microminiaturized Membrane Pumps," 7th International Conference on Solid-State Sensors and Actuators, Yokohama, Japan, pp. 2 cover pp. 106-109, Jun. 7-10, 1993.

Zhang, B. et al., "Microfabricated Devices for Capillary Electrophoresis-Electrospray Mass Spectrometry," Analytical Chemistry, vol. 71, No. 15, pp. 3258-3264, Aug. 1, 1999.

* cited by examiner

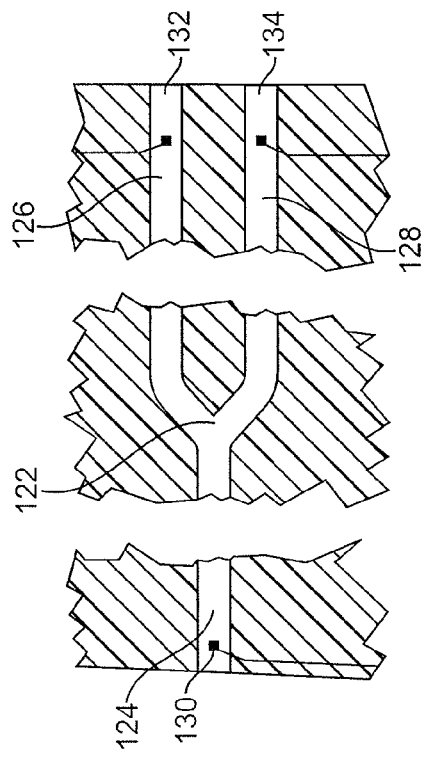
FIG. 4A
FIG. 4B
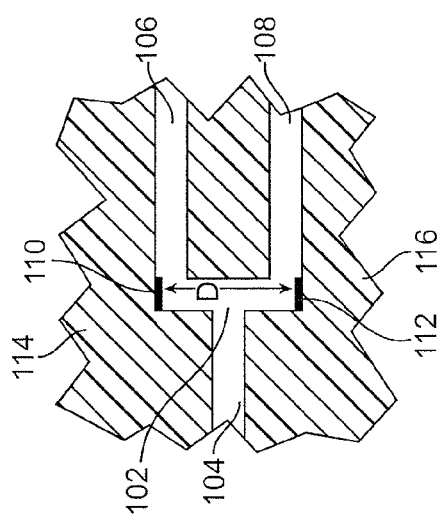
FIG. 4C
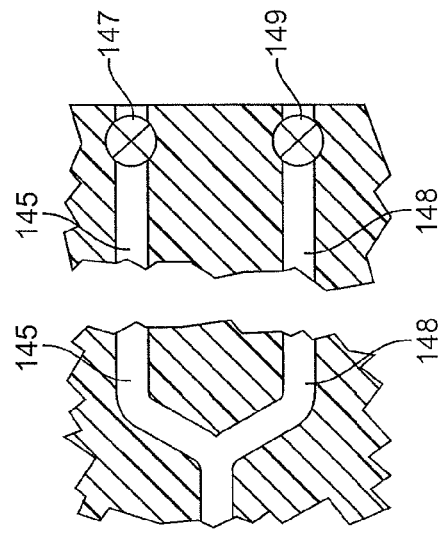
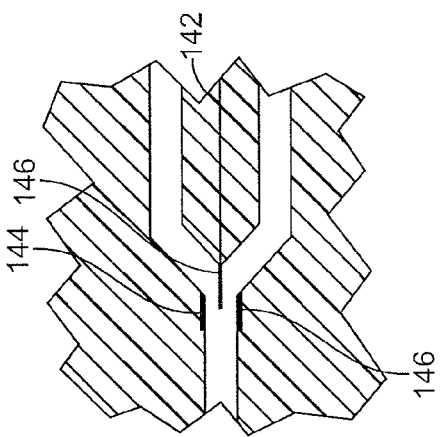
FIG. 4D (Line drawing of photograph)

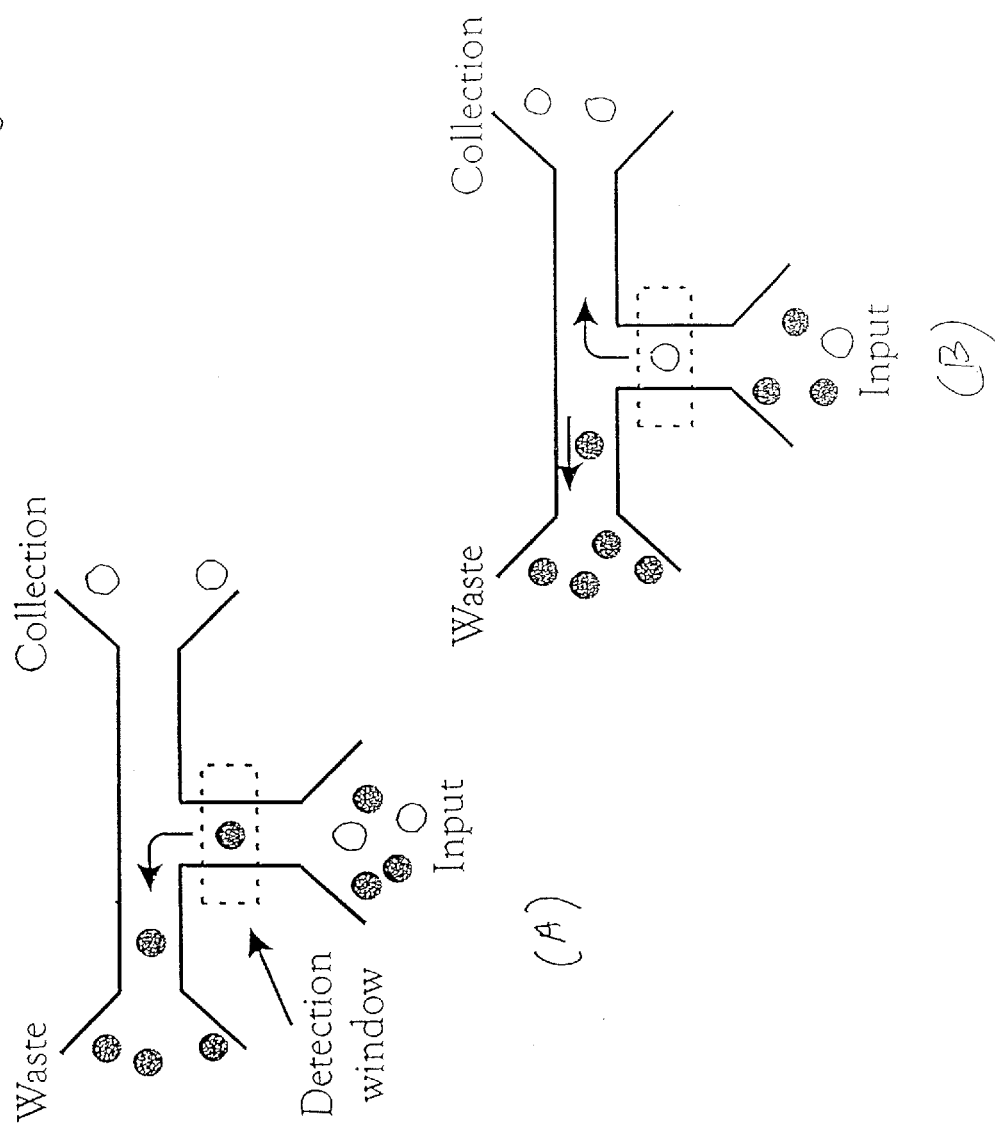

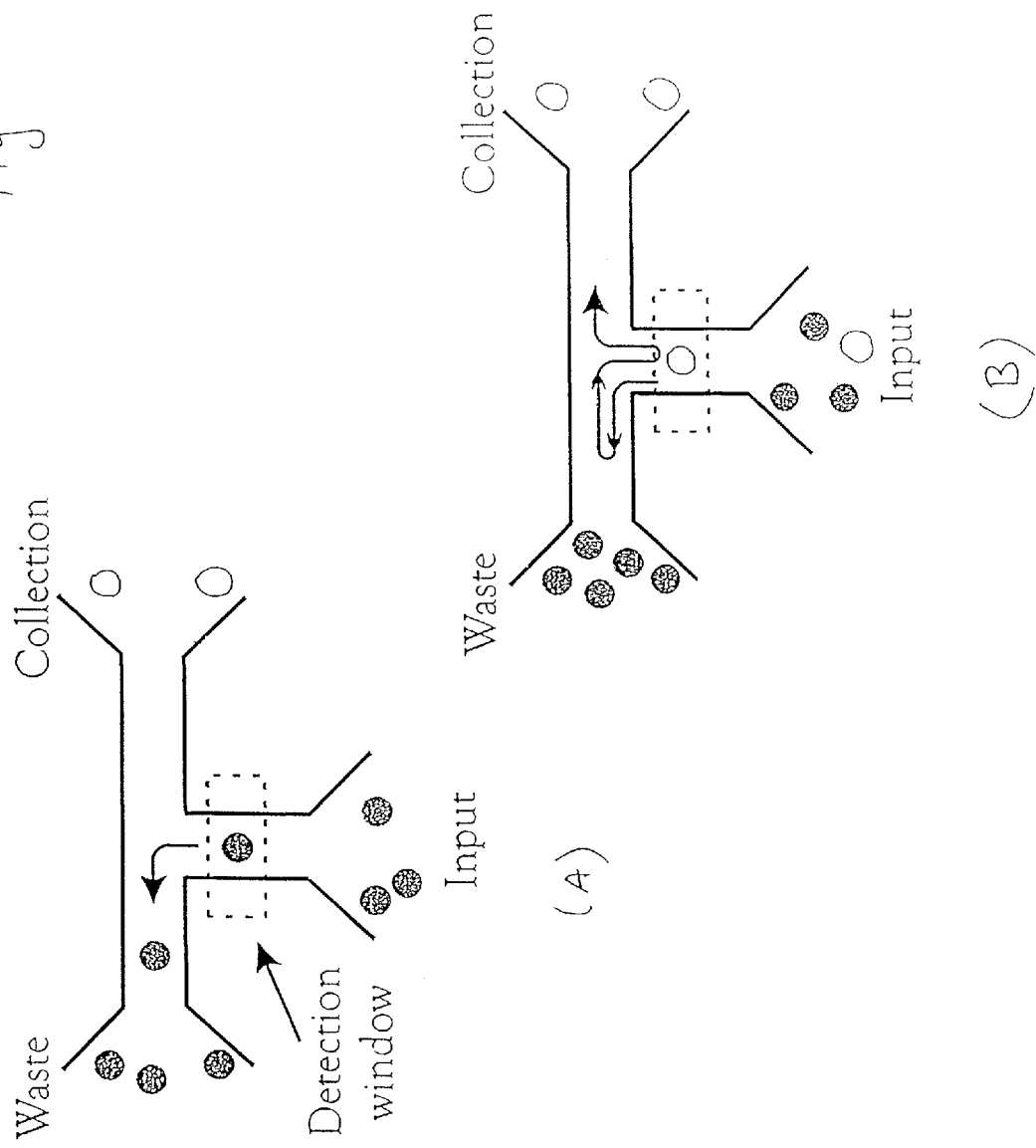

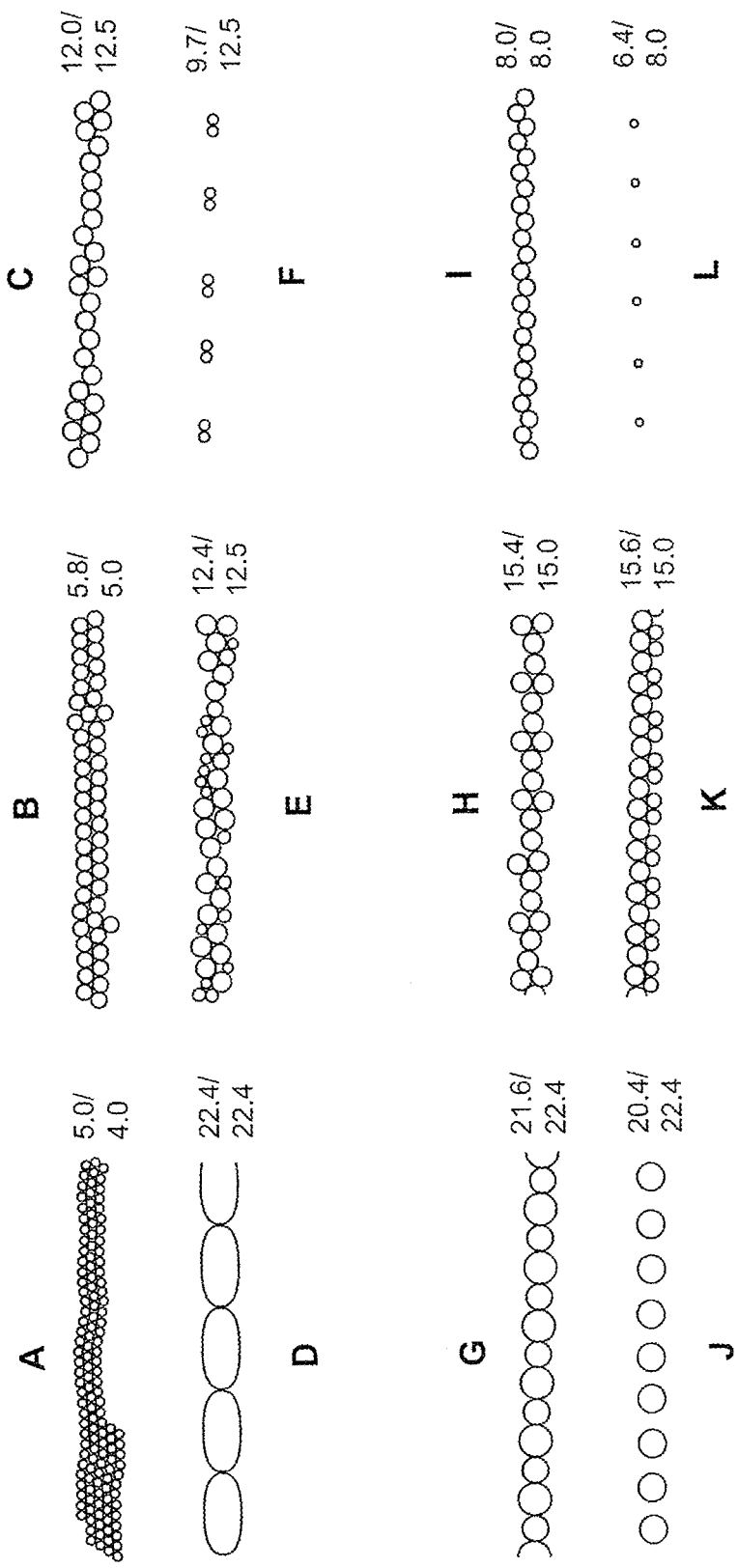
FIG. 19 (Line drawings of photomicrographs)

MICROFABRICATED CROSSFLOW DEVICES AND METHODS

This application is a continuation of U.S. patent application Ser. No. 11/868,942 (issued as U.S. Pat. No. 8,252,539), filed Oct. 8, 2007; which is a continuation of U.S. patent application Ser. No. 09/953,103, filed Sep. 14, 2001 (issued as U.S. Pat. No. 7,294,503); and claims the benefit of U.S. Provisional Application Ser. No. 60/246,793, filed Nov. 8, 2000; and U.S. Provisional Application Ser. No. 60/233,037, filed Sep. 15, 2000.

The above listed applications are hereby incorporated herein in their entirety for all purposes.

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

STATEMENT AS TO RIGHTS TO INVENTIONS MADE UNDER FEDERALLY SPONSORED RESEARCH OR DEVELOPMENT

This invention was made with government support under Grant No. PHY-9722417 awarded by the National Science Foundation. The government has certain rights in the invention.

FIELD OF THE INVENTION

This invention relates to microfluidic devices and methods, including microfabricated, multi-layered elastomeric devices with active pumps and valves. More particularly, the devices and methods of the invention are designed to compartmentalize small droplets of aqueous solution within microfluidic channels filled with oil. The devices and methods of the invention comprise a main channel, through which a pressurized stream of oil is passed, and at least one sample inlet channel, through which a pressurized stream of aqueous solution is passed. A junction or "droplet extrusion region" joins the sample inlet channel to the main channel such that the aqueous solution can be introduced to the main channel, e.g., at an angle that is perpendicular to the stream of oil. By adjusting the pressure of the oil and/or the aqueous solution, a pressure difference can be established between the two channels such that the stream of aqueous solution is sheared off at a regular frequency as it enters the oil stream, thereby forming droplets. In preferred embodiments, the droplets of aqueous solution have a volume of approximately 0.1 to 100 picoliters (pl).

The droplets of aqueous solution, as well as materials contained therein, can be evaluated and/or sorted, e.g., using various channels and valves that can also be incorporated into the microfluidic devices and methods of the invention. The materials sorted by the devices and methods of the invention are preferably particles, preferably small particles (e.g., particles smaller than about 120 µm in diameter) and more preferably particles that are smaller than can ordinarily be detected by conventional methods of flow cytometry (e.g., below about 150 nm in diameter). In a preferred embodiment, the devices and methods of the invention are used to sort or evaluate virions or virus particles. Other preferred embodiments are used to sort or evaluate molecules, such as nucleic acids or proteins, or cells, such as bacteria or pathogens.

BACKGROUND OF THE INVENTION

Viruses are aetiological agents in a range of diseases in humans and animals, including influenza, mumps, infectious mononucleosis, the common cold, poliomyelitis, measles, german measles, herpes (oral and genital), chickenpox, hepatitis, rabies, warts, cancer and acquired immunodeficiency syndrome (AIDS), to name a few. Viruses range in size from approximately 20-25 nm diameter or less (parvoviridae, picornoviridae) to approximately 200-450 nm maximum dimension (poxyiridae), although filamentous viruses may reach lengths of 2000 nm (closterviruses) and can therefore be larger than some bacteria. Viruses lack metabolic machinery of their own and are dependent on their host cells for replication. Therefore, they cannot be grown in synthetic culture media like many other pathogens. Accordingly, specialized approaches are necessary for laboratory diagnosis of viral disease. For example, viruses may be grown in animals, embryonated eggs, or in cell cultures where animal host cells are grown in a synthetic medium and the viruses are then grown in these cells.

Laboratory diagnosis of viral infection is based generally on three approaches: (a) virus isolation, followed by identification (e.g., tissue culture techniques); (b) direct detection of viral components in infected tissues (e.g., by electron microscopy); and (c) demonstration of a significant increase in virus-specific antibodies (e.g., serological techniques). Molecular techniques such as DNA probes or the polymerase chain reaction (PCR) are used for the detection of viruses where cell culture or serological methods are difficult, expensive or unavailable. PCR is also generally the method of choice to detect viral DNA or RNA directly in clinical specimens. The advantage of PCR for viral diagnostics is its high sensitivity; PCR can detect very low numbers of viruses in a small clinical specimen. However, this sensitivity of detection can also cause significant problems in routine viral diagnostics. The significant risk of cross-contamination from sample to sample can outweigh the benefits of detecting small quantities of a target viral nucleic acid. Cross-contamination can also result in false positives, making interpretation of epidemiological data impossible.

Flow sorting devices have been used to analyze and separate larger biological materials, such as biological cells. Conventional flow sorters, such as FACS have numerous problems that render them impractical for analyzing and sorting viruses and other similarly sized particles. FACS and other conventional flow sorters are designed to have a flow chamber with a nozzle and use the principle of hydrodynamic focusing with sheath flow to separate or sort material such as biological cells (1-6). In addition, most sorting instruments combine the technology of ink-jet writing and the effect of gravity to achieve a high sorting rate of droplet generation and electrical charging (7-9).

Despite these advances, many failures of these instruments are due to problems in the flow chamber. For example, orifice clogging, particle absorption and contamination in the tubing may cause turbulent flow in the jet stream. These problems contribute to the great variation in illumination and detection in conventional FACS devices. Another major problem, known as sample carryover, occurs when remnants of previous specimens left in the channel back-flush into the new sample stream during consecutive runs. A potentially more serious problem occurs when dyes remain on the tubing and the chamber, which may give false signals to the fluorescence detection or light scattering apparatus. Although such systems can be sterilized between runs, the procedure is costly, time consuming, inefficient and results in hours of machine down time.

In addition, each cell, as it passes through the orifice, may generate a different perturbation in response to droplet formation. Larger cells can possibly change the droplet size, non-spherical cells tend to align with the long axis parallel to the flow axis, and deformable cells may elongate in the direction of the flow (8, 9). This can result in some variation in the time from the analysis to the actual sorting event. Furthermore, a number of technical problems make it difficult to generate identically charged droplets, which increases deflection error. A charged droplet may cause the next droplet of the opposite polarity to have a reduced charge. On the other hand, if consecutive droplets are charged identically, then the first droplet might have a lower potential than the second droplet, and so on. However, charged droplets will have a defined trajectory only if they are charged identically. In addition, increasing droplet charges may cause mutual electrostatic repulsion between adjacent droplets, which also increases deflection error. Other factors, such as the very high cost for even modest conventional FACS equipment, the high cost of maintenance, and the requirement for trained personnel to operate and maintain the equipment further hinder the widespread accessibility and use of this technology.

Flow cytometry has also been used to separate biological cells. For example, Harrison et al. (38) disclose a microfluidic device that manipulates and stops the flow of fluid through a microfabricated chip so that a cell can be observed after it interacts with a chemical agent. The cells and the chemical agent are loaded into the device via two different inlet channels, which intersect with a main flow path. The flow of the fluid is controlled by a pressure pump or by electric fields (electrophoretic or electro-osmotic) and can be stopped so that the cells can be observed after they mix and interact with the reagent. The cells then pass through the main flow pathway, which terminates through a common waste chamber. Harrison et al. do not, however, provide a device or methods for sorting cells or other biological materials, nor do they suggest or motivate one having ordinary skill in the art to make and use any such device.

For reasons of sensitivity, flow cytometry has by and large been limited to the analysis of cells. Although it is marginally possible to observe light scatter directly from large viruses, this strains the detection limit for conventional flow cytometry. The practical limit of detection for these traditional methods is a spherical particle no smaller than 150 nm, which excludes many viruses (8). The development of flow cytometric techniques for the sorting of viruses is also plagued by other problems related to the size of virus particles. Their small size results in a high diffusion constant making them difficult to control by sheath flow. Containment of the viruses is also important during any flow cytometry sorting process because extruding droplets containing viruses presents a potential biohazard.

SUMMARY OF THE INVENTION

The invention addresses the above-discussed and other problems in the art and provides new devices and methods for sorting viruses and other particles by flow cytometry. The invention provides microfabricated devices having channels that form the boundary for a fluid instead of using a sheath flow employed by conventional FACS. The channels of the device carry a mixture of incompatible or immiscible fluids, such an oil-water mixture. Droplets of aqueous solution containing viral or other particles are dispersed within the oil or other incompatible solvent. Preferably, each droplet of this multi-phase mixture encapsulates a single particle. The droplets are trapped and their boundaries are defined by channel walls, and therefore they do not diffuse and/or mix. Thus, individual particles or molecules can be separately compartmentalized inside individual droplets. These droplets can be analyzed, combined with other droplets (e.g. to react droplet contents) and/or sorted, as desired.

The invention also provides methods for analyzing and/or sorting viruses by flow cytometry using these devices. The methods include reversible sorting schemes and algorithms.

The microfabricated device and methods of the invention offer several advantages over traditional flow cytometry devices and methods. Since the channels present in the device can be made with micron dimensions, the volume of the detection region is precisely controlled and there is no need for hydrodynamic focusing. The planar geometry of the device allows the use of high numerical aperture optics, thereby increasing the sensitivity of the system. Fluid flows continuously through the system and there is no need for charged droplets, so that many difficult technical issues associated with traditional, e.g., FACS devices are avoided. Because the system is entirely self-contained, there is no aerosol formation, allowing for much safer sorting of biohazardous materials such as viruses and other pathogens. Also, the sorting devices of the invention are inexpensive and disposable, which obviates the need for cleaning and sterilization and prevents cross-contamination. The distance between the detection region and the sorting or discrimination region of the device can be short (on the order of a few microns). Materials sorted in the device are compartmentalized within individual droplets of an aqueous solution traveling in a flow of a second, incompatible or immiscible solution. Thus, there is no problem with the material diffusing or exchanging positions, even when sorting or analyzing extremely small particles such as viruses. In a preferred embodiment, water droplets are extruded into a flow of oil, but any fluid phase may be used as a droplet phase and any other incompatible or immiscible fluid or phase may be used as a barrier phase.

A microfluidic device provided by the invention comprises a main channel and at least one inlet region which is in communication with the main channel at a droplet extrusion region. A first fluid flows through the main channel, and a second fluid, which is incompatible or immiscible with the second fluid, passes through the inlet region so that droplets of the second fluid are sheared into the main channel. For example, the first phase or fluid which flows through the main channel can be a non-polar solvent, such as decane (e.g., tetradecane or hexadecane) or another oil (for example, mineral oil). The second phase or fluid which passes through the inlet region can be an aqueous solution, for example ultra pure water, TE buffer, phosphate buffer saline and acetate buffer. The second fluid may also contain a biological sample (e.g., molecules of an enzyme or a substrate, or one or more cells, or one or more viral particles) for analysis or sorting in the device. In preferred embodiments the second fluid includes a biological sample that comprises one or more molecules, cells, virions or particles. In exemplary embodiments for detecting and sorting droplet contents, the droplets of the second fluid each contains, on average, no more than one particle. For example, in preferred embodiments where the biological material comprises viral particles, each droplet preferably contains, on average, no more than one viral particle. Thus, probabilistically, and depending on the concentration of sample in the second fluid, many droplets may have no virions. In other embodiments, droplets may contain more than one particle, and if desired, droplets can be sorted and/or enriched according to their contents. In preferred embodiments, the droplet extrusion region comprises a T-shaped junction between the inlet region and the main channel, so that the second fluid enters the main channel at an angle perpendicular to the flow of the first fluid, and is sheared off into the flow of the first fluid in the main channel.

The device of the invention may also comprise a detection region which is within or coincident with at least a portion of the main channel at or downstream of the droplet extrusion region. The device may also have a detector, preferably an optical detector such as a microscope, associated with the detection region.

In sorter embodiments, the device of the invention may also comprise a discrimination region, which is downstream from the detection region, and a flow control system that is responsive to the detector and adapted to direct droplets through the discrimination region and into a branch channel. The main channel of the device preferably resides in a layer of elastomeric material, which may be adjacent to a substrate layer.

In another preferred embodiment, the device of the invention comprises at least two inlet regions, each connecting to the main channel at a droplet extrusion region. In particular, the device may comprise a first inlet region in communication with the main channel at a first droplet extrusion region, and a second inlet region in communication with the main channel at a second droplet extrusion region. A fluid containing a first biological material may pass through the first inlet region so that droplets of the fluid containing the first biological material are sheared into the main channel. A fluid containing a second biological material may pass through the second inlet region so that droplets of the fluid containing the second biological material are sheared into the main channel. In various aspects, the droplets of the first material may mix or combine with the droplets of the second biological material, and the first and second biological materials may interact with each other upon mixing. For example, the first biological material may be an enzyme and the second biological material may be a substrate for the enzyme. The interaction of the first and second biological materials may produce a signal that can be detected, e.g., as the droplet passes through a detection region associated with the device.

The invention also provides a device for sorting biological material comprising: a microfabricated substrate; a detection region; and a flow control region. In more detail, the microfabricated substrate has at least one main channel, an inlet which meets the main channel at a droplet extrusion region, and at least two branch channels meeting at a junction downstream from the droplet extrusion region. The detection region of the device is within or coincident with at least a portion of the main channel, and is also associated with a detector. The flow control system of the device is responsive to the detector and is adapted to direct biological material into a branch channel.

In preferred embodiments, a first fluid, which may be referred to as an "extrusion" or "barrier" fluid, passes (i.e., flows) through the main channel of the device and a second fluid, referred to as a "sample" or "droplet" fluid, passes or flows through the inlet region. The sample fluid is, specifically, a fluid which is incompatible with the extrusion fluid and contains the biological material or sample. Thus, droplets of the sample fluid containing the biological material for analysis, reaction or sorting are sheared at the droplet extrusion region into the flow of the extrusion fluid in the main channel. Preferably the droplets of the sample fluid each contain, on average, no more than one particle of the biological material. For example, in preferred embodiments wherein the biological material comprises viral particles, each droplet preferably contains, on average, no more than one viral particle. The flow control of the device may be adapted to direct the droplets into a branch channel of the device, e.g., according to a predetermined characteristic of the droplet (or of the biological material within the droplet) that is detected by a detector as the droplet passes through a detection region of the device. In preferred embodiments, the extrusion fluid is a non-polar solvent, such a decane (e.g., tetradecane or hexadecane) or another oil (for example, mineral oil), and the sample fluid is an aqueous solution, such as ultra pure water, a solution of TE buffer, a solution of phosphate buffer saline or a solution of an acetate buffer. In preferred embodiments, the extrusion fluid may also contain one or more additives. For example, in preferred embodiments the extrusion fluid is a non-polar solvent or oil (e.g., decane, tetradecane or hexadecane) and contains at least one surfactant.

The invention also provides a method for sorting biological material. In various embodiments of the method, the biological material may be, e.g., molecules (for example, polynucleotides, polypeptides, enzymes, substrates or mixtures thereof), cells or viral particles, or mixtures thereof. In preferred embodiments, the biological material comprises viral particles.

The method, which is preferably implemented using a microfabricated device of the invention, comprises steps of: (a) providing droplets of a sample fluid containing the biological material to the main channel of a microfabricated substrate; (b) interrogating each droplet (or the biological material within each droplet) for a predetermined characteristic as it passes through a detection region associated with the main channel; and (c) directing the flow of each droplet into a selected branch channel according to the results of the interrogation. An extrusion fluid, which is incompatible with the sample fluid, flows through the main channel so that the droplets of the sample fluid are within the flow of the extrusion fluid in the main channel. In preferred embodiments, the droplets are droplets of an aqueous solution; for example, a solution of ultra pure water, TE buffer, phosphate buffer saline or acetate buffer. The fluid which flows through the main channel (i.e., the extrusion fluid) is preferably a non-polar solvent, such as decane (e.g., tetradecane or hexadecane) or another oil. The extrusion fluid may also contain one or more additives, such as surfactants, as described above. Preferably, the droplets of the sample fluid each contain, on average, no more than one particle of the biological material. For example, in preferred embodiments wherein the biological material comprises viral particles, each droplet preferably contains, on average, no more than one viral particle.

Sorting of biological material, although frequently desired, is not necessary in order to use the devices or practice the methods of the present invention. In particular, the devices and methods of the invention also include embodiments wherein the biological material is analyzed and/or identified, but is not sorted.

BRIEF DESCRIPTION OF THE DRAWINGS

FIG. 4A shows one embodiment of a discrimination region and associated channels used in a sorting device, having electrodes disposed within the channels for electrophoretic discrimination; FIG. 4B shows another embodiment having electrodes disposed for electro-osmotic discrimination; FIGS. 4C and 4D show two additional embodiments having valves disposed for pressure electrophoretic separation, where the valves are within the branch point, as shown in FIG. 4C, or within the branch channels, as shown in FIG. 4D.

FIGS. 14A and B show a sorting scheme according to the invention, in diagrammatic form.

FIGS. 15A and B show a reversible sorting scheme according to the invention.

FIGS. 17A and B show an S-shaped and U-shaped channel, respectively. FIG. 17C shows a T-shaped junction.

FIG. 19 provides photomicrographs (Frames A-L) showing droplets of aqueous solution in a flow of oil (hexadecane with 2% Span 80 surfactant) in a microfluidic device with rounded channels. The relative water/oil pressures are provided to the right of each photomicrograph.

DETAILED DESCRIPTION OF THE INVENTION

Definitions

Figures 1A, 1B:
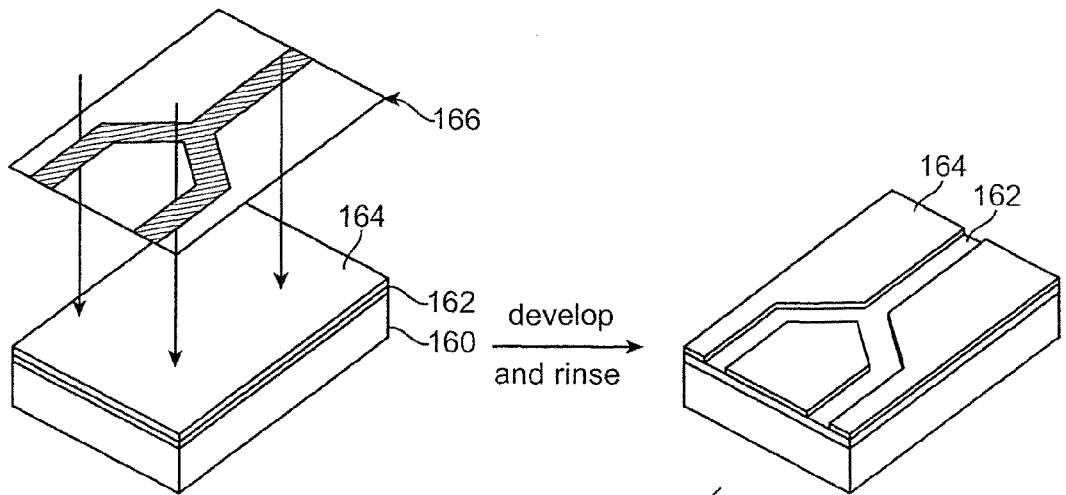
FIGS. 1A through 1D show steps in photolithographic microfabrication of a sorting device from a silicon wafer, using photolithography and several stages of etching.
Figures 1C, 1D:
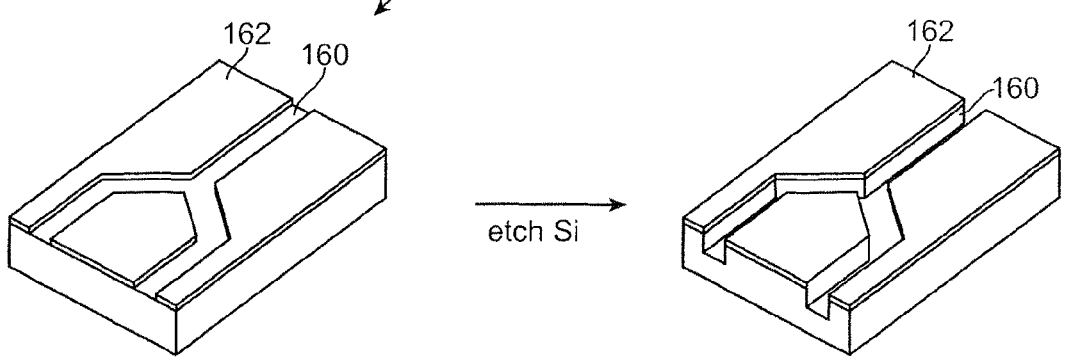

The terms used in this specification generally have their ordinary meanings in the art, within the context of this invention and in the specific context where each term is used. Certain terms are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can typically be described in more than one way. Consequently, alternative language and synonyms may be used for any one or more of the terms discussed herein. Synonyms for certain terms are provided. However, a recital of one or more synonyms does not exclude the use of other synonyms, nor is any special significance to be placed upon whether or not a term is elaborated or discussed herein.

The invention is also described by means of particular examples. However, the use of such examples anywhere in the specification, including examples of any terms discussed herein, is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

As used herein, "about" or "approximately" shall generally mean within 20 percent, preferably within 10 percent, and more preferably within 5 percent of a given value or range.

The term "molecule" means any distinct or distinguishable structural unit of matter comprising one or more atoms, and includes for example polypeptides and polynucleotides.

The term "polymer" means any substance or compound that is composed of two or more building blocks ('mers') that are repetitively linked to each other. For example, a "dimer" is a compound in which two building blocks have been joined together.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

Thus, a "polynucleotide" or "nucleotide sequence" is a series of nucleotide bases (also called "nucleotides") generally in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polypeptide" (one or more peptides) is a chain of chemical building blocks called amino acids that are linked together by chemical bonds called peptide bonds. A "protein" is a polypeptide produced by a living organism. A protein or polypeptide may be "native" or "wild-type", meaning that it occurs in nature; or it may be a "mutant", "variant" or "modified", meaning that it has been made, altered, derived, or is in some way different or changed from a native protein, or from another mutant.

An "enzyme" is a polypeptide molecule, usually a protein produced by a living organism, that catalyzes chemical reactions of other substances. The enzyme is not itself altered or destroyed upon completion of the reaction, and can therefore be used repeatedly to catalyze reactions. A "substrate" refers to any substance upon which an enzyme acts.

As used herein, "particles" means any substance that may be encapsulated within a droplet for analysis, reaction, sorting, or any operation according to the invention. Particles are not only objects such as microscopic beads (e.g., chromatographic and fluorescent beads), latex, glass, silica or paramagnetic beads, but also includes other encapsulating porous and/or biomaterials such as liposomes, vesicles and other emulsions. Beads ranging in size from 0.1 micron to 1 mm can be used in the devices and methods of the invention and are therefore encompassed with the term "particle" as used herein. The term particle also encompasses biological cells, as well as beads and other microscopic objects of similar size (e.g., from about 0.1 to 120 microns, and typically from about 1 to 50 microns) or smaller (e.g., from about 0.1 to 150 nm). For example, the term "particle" further encompasses virions and objects of similar size (e.g., from 0.1 to 500 nm, and typically from about 0.1 to 150 nm). The devices and methods of the invention are also directed to sorting and/or analyzing molecules of any kind, including polynucleotides, polypeptides and proteins (including enzymes) and their substrates. Thus, the term particle further encompasses these materials.

In preferred embodiments, particles (including, e.g., cells, virions and molecules) are sorted and/or analyzed by encapsulating the particles into individual droplets (e.g., droplets of aqueous solution in oil), and these droplets are then sorted, combined and/or analyzed in a microfabricated device. Accordingly, the term "droplet" generally includes anything that is or can be contained within a droplet.

As used herein, "cell" means any cell or cells, as well as viruses or any other particles having a microscopic size, e.g. a size that is similar to or smaller than that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. Since the microfabricated device of the invention is directed to sorting materials having a size similar to a biological cell (e.g. about 0.1 to 120 microns) or smaller (e.g., about 0.1 to 150 nm) any material having a size similar to or smaller than a biological cell can be characterized and sorted using the microfabricated device of the invention. Thus, the term cell shall further include microscopic beads (such as chromatographic and fluorescent beads), liposomes, emulsions, or any other encapsulating biomaterials and porous materials. Non-limiting examples include latex, glass, or paramagnetic beads; and vesicles such as emulsions and liposomes, and other porous materials such as silica beads. Beads ranging in size from 0.1 micron to 1 mm can also be used, for example in sorting a library of compounds produced by combinatorial chemistry. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). The term cell further encompasses "virions", whether or not virions are expressly mentioned.

A "virion", "virus particle" is the complete particle of a virus. Viruses typically comprise a nucleic acid core (comprising DNA or RNA) and, in certain viruses, a protein coat or "capsid". Certain viruses may have an outer protein covering called an "envelope". A virion may be either living (i.e., "viable") or dead (i.e., "non-viable"). A living or "viable" virus is one capable of infecting a living cell. Viruses are generally smaller than biological cells and typically range in size from about 20-25 nm diameter or less (parvoviridae, picornoviridae) to approximately 200-450 nm (poxyiridae). However, some filamentous viruses may reach lengths of 2000 nm (closterviruses) and are therefore larger than some bacterial cells. Since the microfabricated device of the invention is particularly suited for sorting materials having a size similar to a virus (i.e., about 0.1 to 150 nm), any material having a size similar to a virion can be characterized and sorted using the microfabricated device of the invention. Non-limiting examples include latex, glass or paramagnetic beads; vesicles such as emulsions and liposomes; and other porous materials such as silica beads. Beads ranging in size from 0.1 to 150 nm can also be used, for example, in sorting a library of compounds produced by combinatorial chemistry. As used herein, a virion may be charged or uncharged. For example, charged beads may be used to facilitate flow or detection, or as a reporter. Biological viruses, whether viable or non-viable, may be charged, for example, by using a surfactant, such as SDS.

A "reporter" is any molecule, or a portion thereof, that is detectable, or measurable, for example, by optical detection. In addition, the reporter associates with a molecule, cell or virion or with a particular marker or characteristic of the molecule, cell or virion, or is itself detectable to permit identification of the molecule, cell or virion, or the presence or absence of a characteristic of the molecule, cell or virion. In the case of molecules such as polynucleotides such characteristics include size, molecular weight, the presence or absence of particular constituents or moieties (such as particular nucleotide sequences or restrictions sites). In the case of cells, characteristics which may be marked by a reporter includes antibodies, proteins and sugar moieties, receptors, polynucleotides, and fragments thereof. The term "label" can be used interchangeably with "reporter". The reporter is typically a dye, fluorescent, ultraviolet, or chemiluminescent agent, chromophore, or radio-label, any of which may be detected with or without some kind of stimulatory event, e.g., fluoresce with or without a reagent. In one embodiment, the reporter is a protein that is optically detectable without a device, e.g. a laser, to stimulate the reporter, such as horseradish peroxidase (HRP). A protein reporter can be expressed in the cell that is to be detected, and such expression may be indicative of the presence of the protein or it can indicate the presence of another protein that may or may not be coexpressed with the reporter. A reporter may also include any substance on or in a cell that causes a detectable reaction, for example by acting as a starting material, reactant or a catalyst for a reaction which produces a detectable product. Cells may be sorted, for example, based on the presence of the substance, or on the ability of the cell to produce the detectable product when the reporter substance is provided.

A "marker" is a characteristic of a molecule, cell or virion that is detectable or is made detectable by a reporter, or which may be coexpressed with a reporter. For molecules, a marker can be particular constituents or moieties, such as restrictions sites or particular nucleic acid sequences in the case of polynucleotides. For cells and virions, characteristics may include a protein, including enzyme, receptor and ligand proteins, saccharrides, polynucleotides, and combinations thereof, or any biological material associated with a cell or virion. The product of an enzymatic reaction may also be used as a marker. The marker may be directly or indirectly associated with the reporter or can itself be a reporter. Thus, a marker is generally a distinguishing feature of a molecule, cell or virion, and a reporter is generally an agent which directly or indirectly identifies or permits measurement of a marker. These terms may, however, be used interchangeably.

The term "flow" means any movement of liquid or solid through a device or in a method of the invention, and encompasses without limitation any fluid stream, and any material moving with, within or against the stream, whether or not the material is carried by the stream. For example, the movement of molecules, cells or virions through a device or in a method of the invention, e.g. through channels of a microfluidic chip of the invention, comprises a flow. This is so, according to the invention, whether or not the molecules, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the invention.

An "inlet region" is an area of a microfabricated chip that receives molecules, cells or virions for detection measurement or sorting. The inlet region may contain an inlet channel, a well or reservoir, an opening, and other features which facilitate the entry of molecules, cells or virions into the device. A chip may contain more than one inlet region if desired. The inlet region is in fluid communication with the main channel and is upstream therefrom.

An "outlet region" is an area of a microfabricated chip that collects or dispenses molecules, cells or virions after detection, measurement or sorting. An outlet region is downstream from a discrimination region, and may contain branch channels or outlet channels. A chip may contain more than one outlet region if desired.

An "analysis unit" is a microfabricated substrate, e.g., a microfabricated chip, having at least one inlet region, at least one main channel, at least one detection region and at least one outlet region. Sorting embodiments of the analysis unit include a discrimination region and/or a branch point, e.g. downstream of the detection region, that forms at least two branch channels and two outlet regions. A device according to the invention may comprise a plurality of analysis units.

A "main channel" is a channel of the chip of the invention which permits the flow of molecules, cells or virions past a detection region for detection (identification), measurement, or sorting. In a chip designed for sorting, the main channel also comprises a discrimination region. The detection and discrimination regions can be placed or fabricated into the main channel. The main channel is typically in fluid communication with an inlet channel or inlet region, which permits the flow of molecules, cells or virions into the main channel. The main channel is also typically in fluid communication with an outlet region and optionally with branch channels, each of which may have an outlet channel or waste channel. These channels permit the flow of cells out of the main channel.

A "detection region" is a location within the chip, typically within the main channel where molecules, cells or virions to be identified, measured or sorted on the basis of a predetermined characteristic. In a preferred embodiment, molecules, cells or virions are examined one at a time, and the characteristic is detected or measured optically, for example, by testing for the presence or amount of a reporter. For example, the detection region is in communication with one or more microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at the discrimination region. In sorting embodiments the detection region is in fluid communication with a discrimination region and is at, proximate to, or upstream of the discrimination region.

An "extrusion region" or "droplet extrusion region" is a junction between an inlet region and the main channel of a chip of the invention, which permits the introduction of a pressurized fluid to the main channel at an angle perpendicular to the flow of fluid in the main channel. Preferably, the fluid introduced to the main channel through the extrusion region is "incompatible" (i.e., immiscible) with the fluid in the main channel so that droplets of the fluid introduced through the extrusion region are sheared off into the stream of fluid in the main channel.

A "discrimination region" or "branch point" is a junction of a channel where the flow of molecules, cells or virions can change direction to enter one or more other channels, e.g., a branch channel, depending on a signal received in connection with an examination in the detection region. Typically, a discrimination region is monitored and/or under the control of a detection region, and therefore a discrimination region may "correspond" to such detection region. The discrimination region is in communication with and is influenced by one or more sorting techniques or flow control systems, e.g., electric, electro-osmotic, (micro-) valve, etc. A flow control system can employ a variety of sorting techniques to change or direct the flow of molecules, cells or virions into a predetermined branch channel.

A "branch channel" is a channel which is in communication with a discrimination region and a main channel. Typically, a branch channel receives molecules, cells or virions depending on the molecule, cell or virion characteristic of interest as detected by the detection region and sorted at the discrimination region. A branch channel may be in communication with other channels to permit additional sorting. Alternatively, a branch channel may also have an outlet region and/or terminate with a well or reservoir to allow collection or disposal of the molecules, cells or virions.

The term "forward sorting" or flow describes a one-direction flow of molecules, cells or virions, typically from an inlet region (upstream) to an outlet region (downstream), and preferably without a change in direction, e.g., opposing the "forward" flow. Preferably, molecules, cells or virions travel forward in a linear fashion, i.e., in single file. A preferred "forward" sorting algorithm consists of running molecules, cells or virions from the input channel to the waste channel, until a molecule, cell or virion is identified to have an optically detectable signal (e.g. fluorescence) that is above a pre-set threshold, at which point voltages are temporarily changed to electro-osmotically divert the molecule or to the collection channel.

The term "reversible sorting" or flow describes a movement or flow that can change, i.e., reverse direction, for example, from a forward direction to an opposing backwards direction. Stated another way, reversible sorting permits a change in the direction of flow from a downstream to an upstream direction. This may be useful for more accurate sorting, for example, by allowing for confirmation of a sorting decision, selection of particular branch channel, or to correct an improperly selected channel.

Different "sorting algorithms" for sorting in the microfluidic device can be implemented by different programs, for example under the control of a personal computer. As an example, consider a pressure-switched scheme instead of electro-osmotic flow. Electro-osmotic switching is virtually instantaneous and throughput is limited by the highest voltage that can be applied to the sorter (which also affects the run time through ion depletion effects). A pressure switched-scheme does not require high voltages and is more robust for longer runs. However, mechanical compliance in the system is likely to cause the fluid switching speed to become rate-limiting with the "forward" sorting program. Since the fluid is at low Reynolds number and is completely reversible, when trying to separate rare molecules, cells or virions, one can implement a sorting algorithm that is not limited by the intrinsic switching speed of the device. The molecules, cells or virions flow at the highest possible static (non-switching) speed from the input to the waste. When an interesting molecule, cell or virion is detected, the flow is stopped. By the time the flow stops, the molecule, cell or virion may be past the junction and part way down the waste channel. The system is then run backwards at a slow (switchable) speed from waste to input, and the molecule, cell or virion is switched to the collection channel when it passes through the detection region. At that point, the molecule, cell or virion is "saved" and the device can be run at high speed in the forward direction again. Similarly, a device of the invention that is used for analysis, without sorting, can be run in reverse to re-read or verify the detection or analysis made for one or more molecules, cells or virions in the detection region. This "reversible" analysis or sorting method is not possible with standard gel electrophoresis technologies (for molecules) nor with conventional FACS machines (for cells). Reversible algorithms are particularly useful for collecting rare molecules, cells or virions or making multiple time course measurements of a molecule or single cell.

The term "emulsion" refers to a preparation of one liquid distributed in small globules (also referred to herein as drops or droplets) in the body of a second liquid. The first liquid, which is dispersed in globules, is referred to as the discontinuous phase, whereas the second liquid is referred to as the continuous phase or the dispersion medium. In one preferred embodiment, the continuous phase is an aqueous solution and the discontinuous phase is a hydrophobic fluid, such as an oil (e.g., decane, tetradecane, or hexadecane). Such an emulsion is referred to here as an oil in water emulsion. In another embodiment, an emulsion may be a water in oil emulsion. In such an embodiment, the discontinuous phase is an aqueous solution and the continuous phase is a hydrophobic fluid such as an oil. The droplets or globules of oil in an oil in water emulsion are also referred to herein as "micelles", whereas globules of water in a water in oil emulsion may be referred to as "reverse micelles".

Device Architecture and Method

An analyzer or sorter device according to the invention comprises at least one analysis unit having an inlet region in communication with a main channel at a droplet extrusion region (e.g., for introducing droplets of a sample into the main channel), a detection region within or coincident with all or a portion of the main channel or droplet extrusion region, and a detector associated with the detection region. In certain embodiments the device may have two or more droplet extrusion regions. For example, embodiments are provided in which the analysis unit has a first inlet region in communication with the main channel at a first droplet extrusion region, a second inlet region in communication with the main channel at a second droplet extrusion region (preferably downstream from the first droplet extrusion region), and so forth.

Sorter embodiments of the device also have a discrimination region or branch point in communication with the main channel and with branch channels, and a flow control responsive to the detector. There may be a plurality of detection regions and detectors, working independently or together, e.g., to analyze one or more properties of a sample. The branch channels may each lead to an outlet region and to a well or reservoir. There may also be a plurality of inlet regions, each of which introduces droplets of a different sample (e.g., of cells, of virions or of molecules such as molecules of an enzyme or a substrate) into the main channel. Each of the one or more inlet regions may also communicate with a well or reservoir.

As each droplet passes into the detection region, it is examined for a predetermined characteristic (i.e., using the detector) and a corresponding signal is produced, for example indicating that "yes" the characteristic is present, or "no" it is not. The signal may correspond to a characteristic qualitatively or quantitatively. That is, the amount of the signal can be measured and can correspond to the degree to which a characteristic is present. For example, the strength of the signal may indicate the size of a molecule, or the potency or amount of an enzyme expressed by a cell, or a positive or negative reaction such as binding or hybridization of one molecule to another, or a chemical reaction of a substrate catalyzed by an enzyme. In response to the signal, data can be collected and/or a flow control can be activated to divert a droplet into one branch channel or another. Thus, molecules or cells (including virions) within a droplet at a discrimination region can be sorted into an appropriate branch channel according to a signal produced by the corresponding examination at a detection region. Optical detection of molecular, cellular or viral characteristics is preferred, for example directly or by use of a reporter associated with a characteristic chosen for sorting. However, other detection techniques may also be employed.

A variety of channels for sample flow and mixing can be microfabricated on a single chip and can be positioned at any location on the chip as the detection and discrimination or sorting points, e.g., for kinetic studies (10, 11). A plurality of analysis units of the invention may be combined in one device. Microfabrication applied according to the invention eliminates the dead time occurring in conventional gel electrophoresis or flow cytometric kinetic studies, and achieves a better time-resolution. Furthermore, linear arrays of channels on a single chip, i.e., a multiplex system, can simultaneously detect and sort a sample by using an array of photo multiplier tubes (PMT) for parallel analysis of different channels (12). This arrangement can be used to improve throughput or for successive sample enrichment, and can be adapted to provide a very high throughput to the microfluidic devices that exceeds the capacity permitted by conventional flow sorters. Circulation systems can be used in cooperation with these and other features of the invention. Microfluidic pumps and valves are a preferred way of controlling fluid and sample flow. See, for example, U.S. patent application Ser. No. 60/186,856.

Microfabrication permits other technologies to be integrated or combined with flow cytometry on a single chip, such as PCR (13), moving cells using optical tweezer/cell trapping (14-16), transformation of cells by electroporation (17), μTAS (18), and DNA hybridization (5). Detectors and/or light filters that are used to detect viral (or cell) characteristics of the reporters can also be fabricated directly on the chip.

A device of the invention can be microfabricated with a sample solution reservoir or well at the inlet region, which is typically in fluid communication with an inlet channel. A reservoir may facilitate introduction of molecules or cells into the device and into the sample inlet channel of each analysis unit. An inlet region may have an opening such as in the floor of the microfabricated chip, to permit entry of the sample into the device. The inlet region may also contain a connector adapted to receive a suitable piece of tubing, such as liquid chromatography or HPLC tubing, through which a sample may be supplied. Such an arrangement facilitates introducing the sample solution under positive pressure in order to achieve a desired pressure at the droplet extrusion region.

A device of the invention may have an additional inlet region, in direct communication with the main channel at a location upstream of the droplet extrusion region, through which a pressurized stream or "flow" of a fluid is introduced into the main channel. Preferably, this fluid is one which is not miscible with the solvent or fluid of the sample. For example, most preferably the fluid is a non-polar solvent, such as decane (e.g., tetradecane or hexadecane), and the sample (e.g., of cells, virions or molecules) is dissolved or suspended in an aqueous solution so that aqueous droplets of the sample are introduced into the pressurized stream of non-polar solvent at the droplet extrusion region.

Substrate and Flow Channels

A typical analysis unit of the invention comprises a main inlet that is part of and feeds or communicates directly with a main channel, along with one or more sample inlets in communication with the main channel at a droplet extrusion region situated downstream from the main inlet (each different sample inlet preferably communicates with the main channel at a different droplet extrusion region). The droplet extrusion region generally comprises a junction between the sample inlet and the main channel such that a pressurized solution of a sample (i.e., a fluid containing a sample such as cells, virions or molecules) is introduced to the main channel in droplets. Preferably, the sample inlet intersects the main channel such that the pressurized sample solution is introduced into the main channel at an angle perpendicular to a stream of fluid passing through the main channel. For example, in preferred embodiments, the sample inlet and main channel intercept at a T-shaped junction; i.e., such that the sample inlet is perpendicular (90 degrees) to the main channel. However, the sample inlet may intercept the main channel at any angle, and need not introduce the sample fluid to the main channel at an angle that is perpendicular to that flow. In exemplary embodiments the angle between intersecting channels is in the range of from about 60 to about 120 degrees. Particular exemplary angles are 45, 60, 90, and 120 degrees.

The main channel in turn communicates with two or more branch channels at another junction or "branch point", forming, for example, a T-shape or a Y-shape. Other shapes and channel geometries may be used as desired. In sorting embodiments, the region at or surrounding the junction can also be referred to as a discrimination region. Precise boundaries for the discrimination region are not required, but are preferred.

A detection region is within, communicating or coincident with a portion of the main channel at or downstream of the droplet extrusion region and, in sorting embodiments, at or upstream of the discrimination region or branch point. Precise boundaries for the detection region are not required, but are preferred. The discrimination region may be located immediately downstream of the detection region or it may be separated by a suitable distance consistent with the size of the molecules, the channel dimensions and the detection system. It will be appreciated that the channels may have any suitable shape or cross-section (for example, tubular or grooved), and can be arranged in any suitable manner so long as flow can be directed from inlet to outlet and from one channel into another.

The channels of the invention are microfabricated, for example by etching a silicon chip using conventional photolithography techniques, or using a micromachining technology called "soft lithography", developed in the late 1990's (19). These and other microfabrication methods may be used to provide inexpensive miniaturized devices, and in the case of soft lithography, can provide robust devices having beneficial properties such as improved flexibility, stability, and mechanical strength. When optical detection is employed, the invention also provides minimal light scatter from molecule or cell (including virion) suspension and chamber material. Devices according to the invention are relatively inexpensive and easy to set up. They can also be disposable, which greatly relieves many of the concerns of gel electrophoresis (for molecules), and of sterilization and permanent adsorption of particles into the flow chambers and channels of conventional FACS machines (for cells, virions and other particle suspensions). Using these kinds of techniques, microfabricated fluidic devices can replace the conventional fluidic flow chambers of the prior art.

A microfabricated device of the invention is preferably fabricated from a silicon microchip or silicon elastomer. The dimensions of the chip are those of typical microchips, ranging between about 0.5 cm to about 5 cm per side and about 1 micron to about 1 cm in thickness. The device contains at least one analysis unit having a main channel with a droplet extrusion region and a coincident detection region. Preferably, the device also contains at least one inlet region (which may contain an inlet channel) and one or more outlet regions (which may have fluid communication with a branch channel in each region). In a sorting embodiment, at least one detection region cooperates with at least one discrimination region to divert flow via a detector-originated signal. It shall be appreciated that the "regions" and "channels" are in fluid communication with each other and therefore may overlap; i.e., there may be no clear boundary where a region or channel begins or ends. A microfabricated device can be transparent and can be covered with a material having transparent properties, such as a glass coverslip, to permit detection of a reporter, for example, by an optical device such as an optical microscope.

The dimensions of the detection region are influenced by the nature of the sample under study and, in particular, by the size of the molecules or cells (including virions) under study. For example, viruses can have a diameter from about 20 nm to about 500 nm, although some extremely large viruses may reach lengths of about 2000 nm (i.e., as large or larger than some bacterial cells). By contrast, biological cells are typically many times larger. For example, mammalian cells can have a diameter of about 1 to 50 microns, more typically 10 to 30 microns, although some mammalian cells (e.g., fat cells) can be larger than 120 microns. Plant cells are generally 10 to 100 microns.

Detection regions used for detecting molecules and cells (including virions) have a cross-sectional area large enough to allow a desired molecule to pass through without being substantially slowed down relative to the flow carrying it. To avoid "bottlenecks" and/or turbulence, and promote single-file flow, the channel dimensions, particularly in the detection region, should generally be at least about twice, preferably at least about five times as large per side or in diameter as the diameter of the largest molecule, cell or droplet that will be passing through it.

For particles (e.g., cells, including virions) or molecules that are in droplets (i.e., deposited by the droplet extrusion region) within the flow of the main channel, the channels of the device are preferably rounded, with a diameter between about 2 and 100 microns, preferably about 60 microns, and more preferably about 30 microns at the crossflow area or droplet extrusion region. This geometry facilitates an orderly flow of droplets in the channels. See e.g. FIG. 16B. Similarly, the volume of the detection region in an analysis device is typically in the range of between about 10 femtoliters (fl) and 5000 fl, preferably about 40 or 50 fl to about 1000 or 2000 fl, most preferably on the order of about 200 fl. In preferred embodiments, the channels of the device, and particularly the channels of the inlet connecting to a droplet extrusion region, are between about 2 and 50 microns, most preferably about 30 microns.

In one preferred embodiment, droplets at these dimensions tend to conform to the size and shape of the channels, while maintaining their respective volumes. Thus, as droplets move from a wider channel to a narrower channel they become longer and thinner, and vice versa. In preferred embodiments, droplets are at least about four times as long as they are wide. This droplet configuration, which can be envisioned as a lozenge shape, flows smoothly and well through the channels. Longer droplets, produced in narrower channels, provides a higher shear, meaning that droplets can more easily be sheared or broken off from a flow, i.e. using less force. Droplets may also tend to adhere to channel surfaces, which can slow or block the flow, or produce turbulence. Droplet adherence is overcome when the droplet is massive enough in relation to the channel size to break free. Thus, droplets of varying size, if present, may combine to form uniform droplets having a so-called critical mass or volume that results in smooth or laminar droplet flow. Droplets that are longer than they are wide, preferably about four times longer than they are wide, generally have the ability to overcome channel adherence and move freely through the microfluidic device. Thus, in an exemplary embodiment with 60 micron channels, a typical free-flowing droplet is about 60 microns wide and 240 microns long. Droplet dimensions and flow characteristics can be influenced as desired, in part by changing the channel dimensions, e.g. the channel width.

More preferably, however, the microfabricated devices of this invention generate round, monodisperse droplets (such as those illustrated in Frames J and L of FIG. 19). Preferably, the droplets have a diameter that is smaller than the diameter of the microchannel; i.e., preferably less than 60 μm. Monodisperse droplets may be particularly preferably, e.g., in high throughput devices and other embodiments where it is desirable to generate droplets at high frequency.

To prevent material (e.g., cells, virions and other particles or molecules) from adhering to the sides of the channels, the channels (and coverslip, if used) may have a coating which minimizes adhesion. Such a coating may be intrinsic to the material from which the device is manufactured, or it may be applied after the structural aspects of the channels have been microfabricated. "TEFLON" is an example of a coating that has suitable surface properties. Alternatively, the channels may be coated with a surfactant.

Preferred surfactants that may be used include, but are not limited to, surfactants such as sorbitan-based carboxylic acid esters (e.g., the "Span" surfactants, Fluka Chemika), including sorbitan monolaurate (Span20), sorbitan monopalmitate (Span 40), sorbitan monostearate (Span60) and sorbitan monooleate (Span80). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as microreactors for chemical reactions (including biochemical reactions) or are used to analyze and/or sort biomaterials, a water soluble surfactant such as SDS may denature or inactivate the contents of the droplet.

In one particularly preferred embodiment, the extrusion fluid is an oil (e.g., decane, tetradecane or hexadecane) that contains a surfactant. (e.g., a non-ionic surfactant such as a Span surfactant) as an additive (preferably between about 0.2 and 5% by volume, more preferably about 2%). In such an embodiment, a user preferably causes the extrusion fluid to flow through channels of the microfluidic device so that the surfactant in the extrusion fluid coats the channel walls.

A silicon substrate containing the microfabricated flow channels and other components is preferably covered and sealed, most preferably with a transparent cover, e.g., thin glass or quartz, although other clear or opaque cover materials may be used. When external radiation sources or detectors are employed, the detection region is covered with a clear cover material to allow optical access to the cells. For example, anodic bonding to a "PYREX" cover slip can be accomplished by washing both components in an aqueous $H_2SO_4/H_2O_2$ bath, rinsing in water, and then, for example, heating to about 350° C. while applying a voltage of 450V.

Switching and Flow Control

Preferred embodiments of the invention use pressure drive flow control, e.g., utilizing valves and pumps, to manipulate the flow of cells virions, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis (7, 10-11, 20). In certain embodiments of the invention, the flow moves in one "forward" direction, e.g. from the main inlet region through the main and branch channels to an outlet region. In other embodiments the direction of flow is reversible. Application of these techniques according to the invention provides more rapid and accurate devices and methods for analysis or sorting, for example, because the sorting occurs at or in a discrimination region that can be placed at or immediately after a detection region. This provides a shorter distance for molecules or cells to travel, they can move more rapidly and with less turbulence, and can more readily be moved, examined, and sorted in single file, i.e., one at a time. In a reversible embodiment, potential sorting errors can be avoided, for example by reversing and slowing the flow to re-read or resort a molecule, cell or virion (or pluralities thereof) before irretrievably committing the cell or cells to a particular branch channel.

Without being bound by any theory, electro-osmosis is believed to produce motion in a stream containing ions, e.g. a liquid such as a buffer, by application of a voltage differential or charge gradient between two or more electrodes. Neutral (uncharged) molecules or cells (including virions) can be carried by the stream. Electro-osmosis is particularly suitable for rapidly changing the course, direction or speed of flow. Electrophoresis is believed to produce movement of charged objects in a fluid toward one or more electrodes of opposite charge, and away from one on or more electrodes of like charge. In embodiments of the invention where an aqueous phase is combined with an oil phase, aqueous droplets are encapsulated or separated from each other by oil. Typically, the oil phase is not an electrical conductor and may insulate the droplets from the electro-osmotic field. In these embodiment, electro-osmosis may be used to drive the flow of droplets if the oil is modified to carry or react to an electrical field, or if the oil is substituted for another phase that is immiscible in water but which does not insulate the water phase from electrical fields.

Dielectrophoresis is believed to produce movement of dielectric objects, which have no net charge, but have regions that are positively or negatively charged in relation to each other. Alternating, non-homogeneous electric fields in the presence of droplets and/or particles, such as cells or virions, cause the droplets and/or particles to become electrically polarized and thus to experience dielectrophoretic forces. Depending on the dielectric polarizability of the particles and the suspending medium, dielectric particles will move either toward the regions of high field strength or low field strength. For example, the polarizability of living cells and virions depends on their composition, morphology, and phenotype and is highly dependent on the frequency of the applied electrical field. Thus, cells and virions of different types and in different physiological states generally possess distinctly different dielectric properties, which may provide a basis for cell separation, e.g., by differential dielectrophoretic forces. Likewise, the polarizability of droplets also depends upon their size, shape and composition. For example, droplets that contain salts can be polarized. According to formulas provided in Fiedler et al. (11), individual manipulation of single droplets requires field differences (inhomogeneities) with dimensions close to the droplets.

Manipulation is also dependent on permittivity (a dielectric property) of the droplets and/or particles with the suspending medium. Thus, polymer particles, living cells and virions show negative dielectrophoresis at high-field frequencies in water. For example, dielectrophoretic forces experienced by a latex sphere in a 0.5 MV/m field (10V for a 20 micron electrode gap) in water are predicted to be about 0.2 piconewtons (pN) for a 3.4 micron latex sphere to 15 pN for a 15 micron latex sphere (11). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. See e.g. Benecke (21).

Radiation pressure can also be used in the invention to deflect and move objects, e.g. droplets and particles (molecules, cells, virions, etc.) contained therein, with focused beams of light such as lasers. Flow can also be obtained and controlled by providing a pressure differential or gradient between one or more channels of a device or in a method of the invention.

In preferred embodiments, molecules, cells or virions (or droplets containing molecules, cells or virions) can be moved by direct mechanical switching, e.g., with on-off valves or by squeezing the channels. Pressure control may also be used, for example, by raising or lowering an output well to change the pressure inside the channels on the chip. See, e.g., the devices and methods described in pending U.S. patent application Ser. No. 08/932,774, filed Sep. 25, 1997; No. 60/108, 894, filed Nov. 17, 1998; No. 60/086,394, filed May 22, 1998; and Ser. No. 09/325,667, filed May 21, 1999. These methods and devices can further be used in combination with the methods and devices described in pending U.S. patent application Ser. No. 60/141,503, filed Jun. 28, 1999; No. 60/147, 199, filed Aug. 3, 1999; and No. 186,856, filed Mar. 3, 2000 (entitled "Microfabricated Elastomeric Valve and Pump Systems"). Each of these references is hereby incorporated by reference in its entirety. The "pump and valve" drive systems are particularly preferred. They are rapid, efficient, economical, and relatively easy to fabricate and control. Additionally, they do not rely on electrical fields or electrical charges, which may be harder to control and in some cases may potentially affect the droplet contents. Different switching and flow control mechanisms can be combined on one chip or in one device and can work independently or together as desired.

Detection and Discrimination for Sorting

The detector can be any device or method for interrogating a molecule, a cell or a virion as it passes through the detection region. Typically, molecules, cells or virions (or droplets containing such particles) are to be analyzed or sorted according to a predetermined characteristic that is directly or indirectly detectable, and the detector is selected or adapted to detect that characteristic. A preferred detector is an optical detector, such as a microscope, which may be coupled with a computer and/or other image processing or enhancement devices to process images or information produced by the microscope using known techniques. For example, molecules can be analyzed and/or sorted by size or molecular weight. Enzymes can be analyzed and/or sorted by the extent to which they catalyze chemical reaction of a substrate (conversely, substrate can be analyzed and/or sorted by the level of chemical reactivity catalyzed by an enzyme). Cells and virions can be sorted according to whether they contain or produce a particular protein, by using an optical detector to examine each cell or virion for an optical indication of the presence or amount of that protein. The protein may itself be detectable, for example by a characteristic fluorescence, or it may be labeled or associated with a reporter that produces a detectable signal when the desired protein is present, or is present in at least a threshold amount. There is no limit to the kind or number of characteristics that can be identified or measured using the techniques of the invention, which include without limitation surface characteristics of the cell or virion and intracellular characteristics, provided only that the characteristic or characteristics of interest for sorting can be sufficiently identified and detected or measured to distinguish cells having the desired characteristic(s) from those which do not. For example, any label or reporter as described herein can be used as the basis for analyzing and/or sorting molecules or cells (including virions), i.e. detecting molecules or cells to be collected.

In a preferred embodiment, the molecules or cells or virions (or droplets containing them) are analyzed and/or separated based on the intensity of a signal from an optically-detectable reporter bound to or associated with them as they pass through a detection window or "detection region" in the device. Molecules or cells or virions having an amount or level of the reporter at a selected threshold or within a selected range are diverted into a predetermined outlet or branch channel of the device. The reporter signal may be collected by a microscope and measured by a photo multiplier tube (PMT). A computer digitizes the PMT signal and controls the flow via valve action or electro-osmotic potentials. Alternatively, the signal can be recorded or quantified as a measure of the reporter and/or its corresponding characteristic or marker, e.g., for the purpose of evaluation and without necessarily proceeding to sort the molecules or cells.

In one embodiment, the chip is mounted on an inverted optical microscope. Fluorescence produced by a reporter is excited using a laser beam focused on molecules (e.g., DNA, protein, enzyme or substrate) or cells passing through a detection region. Fluorescent reporters include, e.g., rhodamine, fluorescein, Texas red, Cy 3, Cy 5, phycobiliprotein, green fluorescent protein (GFP), YOYO-1 and PicoGreen, to name a few. In molecular fingerprinting applications, the reporter labels are preferably fluorescently labeled single nucleotides, such as fluorescein-dNTP, rhodamine-dNTP, Cy3-dNTP, etc.; where dNTP represents dATP, dTTP, dUTP or dCTP. The reporter can also be chemically-modified single nucleotides, such as biotin-dNTP. In other embodiments, the reporter can be fluorescently or chemically labeled amino acids or antibodies (which bind to a particular antigen, or fragment thereof, when expressed or displayed by a cell or virus).

Thus, in one aspect of the invention, the device can analyze and/or sort cells or virions based on the level of expression of selected cell markers, such as cell surface markers, which have a detectable reporter bound thereto, in a manner similar to that currently employed using fluorescence-activated cell sorting (FACS) machines. Proteins or other characteristics within a cell, and which do not necessarily appear on the cell surface, can also be identified and used as a basis for sorting. In another aspect of the invention, the device can determine the size or molecular weight of molecules such as polynucleotides or polypeptides (including enzymes and other proteins) or fragments thereof passing through the detection region. Alternatively, the device can determine the presence or degree of some other characteristic indicated by a reporter. If desired, the cells, virions or molecules can be sorted based on this analysis. The sorted cells, virions or molecules can be collected from the outlet channels and used as needed.

To detect a reporter or determine whether a molecule, cell or virion has a desired characteristic, the detection region may include an apparatus for stimulating a reporter for that characteristic to emit measurable light energy, e.g., a light source such as a laser, laser diode, high-intensity lamp, (e.g., mercury lamp), and the like. In embodiments where a lamp is used, the channels are preferably shielded from light in all regions except the detection region. In embodiments where a laser is used, the laser can be set to scan across a set of detection regions from different analysis units. In addition, laser diodes may be microfabricated into the same chip that contains the analysis units. Alternatively, laser diodes may be incorporated into a second chip (i.e., a laser diode chip) that is placed adjacent to the microfabricated analysis or sorter chip such that the laser light from the diodes shines on the detection region(s).

In preferred embodiments, an integrated semiconductor laser and/or an integrated photodiode detector are included on the silicon wafer in the vicinity of the detection region. This design provides the advantages of compactness and a shorter optical path for exciting and/or emitted radiation, thus minimizing distortion.

Sorting Schemes

According to the invention, molecules (such as DNA, protein, enzyme or substrate) or particles (i.e., cells, including virions) are sorted dynamically in a flow stream of microscopic dimensions based on the detection or measurement of a characteristic, marker or reporter that is associated with the molecules or particles. More specifically, droplets of a solution (preferably an aqueous solution or buffer), containing a sample of molecules, cells or virions, are introduced through a droplet extrusion region into a stream of fluid (preferably a non-polar fluid such as decane or other oil) in the main channel. The individual droplets are then analyzed and/or sorted in the flow stream, thereby sorting the molecules, cells or virions contained within the droplets.

The flow stream in the main channel is typically, but not necessarily continuous and may be stopped and started, reversed or changed in speed. Prior to sorting, a liquid that does not contain samples molecules, cells or virions can be introduced into a sample inlet region (such as an inlet well or channel) and directed through the droplet extrusion region, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet region.

The pressure at the droplet extrusion region can also be regulated by adjusting the pressure on the main and sample inlets, for example, with pressurized syringes feeding into those inlets. By controlling the pressure difference between the oil and water sources at the droplet extrusion region, the size and periodicity of the droplets generated may be regulated. Alternatively, a valve may be placed at or coincident to either the droplet extrusion region or the sample inlet connected thereto to control the flow of solution into the droplet extrusion region, thereby controlling the size and periodicity of the droplets. Periodicity and droplet volume may also depend on channel diameter, the viscosity of the fluids, and shear pressure.

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with the population of molecules, cells or virions to be analyzed and/or sorted can be used. The fluid passing through the main channel and in which the droplets are formed is preferably one that is not miscible with the droplet forming fluid. Preferably, the fluid passing through the main channel is a non-polar solvent, most preferably decane (e.g., tetradecane or hexadecane) or another oil.

The fluids used in the invention may contain additives, such as agents which reduce surface tensions (surfactants). Exemplary surfactants include Tween, Span, fluorinated oils, and other agents that are soluble in oil relative to water. Surfactants may aid in controlling or optimizing droplet size, flow and uniformity, for example by reducing the shear force needed to extrude or inject droplets into an intersecting channel. This may affect droplet volume and periodicity, or the rate or frequency at which droplets break off into an intersecting channel.

Channels of the invention may be formed from silicon elastomer (e.g. RTV), urethane compositions, of from silicon-urethane composites such as those available from Polymer Technology Group (Berkeley, Calif.), e.g. PurSil™ and CarboSil™. The channels may also be coated with additives or agents, such as surfactants, TEFLON, or fluorinated oils such as octadecafluoroctane (98%, Aldrich) or fluorononane. TEFLON is particularly suitable for silicon elastomer (RTV) channels, which are hydrophobic and advantageously do not absorb water, but they may tend to swell when exposed to an oil phase. Swelling may alter channel dimensions and shape, and may even close off channels, or may affect the integrity of the chip, for example by stressing the seal between the elastomer and a coverslip. Urethane substrates do not tend to swell in oil but are hydrophillic, they may undesirably absorb water, and tend to use higher operating pressures. Hydrophobic coatings may be used to reduce or eliminate water absorption. Absorption or swelling issues may also be addressed by altering or optimizing pressure or droplet frequency (e.g. increasing periodicity to reduce absorption). RTV-urethane hybrids may be used to combine the hydrophobic properties of silicon with the hydrophilic properties of urethane.

Embodiments of the invention are also provided in which there are two or more droplet extrusion regions introducing droplets of samples into the main channel. For example, a first droplet extrusion region may introduce droplets of a first sample into a flow of fluid (e.g., oil) in the main channel and a second droplet extrusion region may introduce droplets of a second sample into the flow of fluid in main channel, and so forth. Preferably, the second droplet extrusion region is downstream from the first droplet extrusion region (e.g., about 30 μm). In a preferred embodiment, the fluids introduced into the two or more different droplet extrusion regions comprise the same fluid or the same type of fluid (e.g., different aqueous solutions). For example, in one embodiment droplets of an aqueous solution containing an enzyme are introduced into the main channel at the first droplet extrusion region and droplets of aqueous solution containing a substrate for the enzyme are introduced into the main channel at the second droplet extrusion region. The introduction of droplets through the different extrusion regions may be controlled, e.g., so that the droplets combine (allowing, for example, the enzyme to catalyze a chemical reaction of the substrate). Alternatively, the droplets introduced at the different droplet extrusion regions may be droplets of different fluids which may be compatible or incompatible. For example, the different droplets may be different aqueous solutions, or droplets introduced at a first droplet extrusion region may be droplets of one fluid (e.g., an aqueous solution) whereas droplets introduced at a second droplet extrusion region may be another fluid (e.g., alcohol or oil).

The concentration (i.e., number) of molecules, cells or virions in a droplet can influence sorting efficiently and therefore is preferably optimized. In particular, the sample concentration should be dilute enough that most of the droplets contain no more than a single molecule, cell or virion, with only a small statistical chance that a droplet will contain two or more molecules, cells or virions. This is to ensure that for the large majority of measurements, the level of reporter measured in each droplet as it passes through the detection region corresponds to a single molecule, cell or virion and not to two or more molecules, cells or virions.

The parameters which govern this relationship are the volume of the droplets and the concentration of molecules, cells or virions in the sample solution. The probability that a droplet will contain two or more molecules cells or virions ($P_{\leq 2}$) can be expressed as $$P_{\leq 2}=1-\{1+[\text{virion}]\times V\}\times e^{-[\text{virion}]\times V}$$

where "[virion]" is the concentration of molecules, cells or virions in units of number of molecules, cells or virions per cubic micron ($\mu m^3$), and V is the volume of the droplet in units of $\mu m^3$.

It will be appreciated that $P_{\leq 2}$ can be minimized by decreasing the concentration of molecules, cells or virions in the sample solution. However, decreasing the concentration of molecules, cells or virions in the sample solution also results in an increased volume of solution processed through the device and can result in longer run times. Accordingly, it is desirable to minimize to presence of multiple molecules, cells or virions in the droplets (thereby increasing the accuracy of the sorting) and to reduce the volume of sample, thereby permitting a sorted sample in a reasonable time in a reasonable volume containing an acceptable concentration of molecules, cells or virions.

The maximum tolerable $P_{\leq 2}$ depends on the desired "purity" of the sorted sample. The "purity" in this case refers to the fraction of sorted molecules, cells or virions that posses a desired characteristic (e.g., display a particular antigen, are in a specified size range or are a particular type of molecule, cell or virion). The purity of the sorted sample is inversely proportional to $P_{\leq 2}$. For example, in applications where high purity is not needed or desired a relatively high $P_{\leq 2}$ (e.g., $P_{\leq 2}$=0.2) may be acceptable. For most applications, maintaining $P_{\leq 2}$ at or below about 0.1, preferably at or below about 0.01, provides satisfactory results.

A sample solution containing a mixture or population of molecule, cells or virions in a suitable carrier fluid (such as a liquid or buffer described above) is supplied to the sample inlet region, and droplets of the sample solution are introduced, at the droplet extrusion region, into the flow passing through the main channel. The force and direction of flow can be controlled by any desired method for controlling flow, for example, by a pressure differential, by valve action or by electro-osmotic flow (e.g., produced by electrodes at inlet and outlet channels). This permits the movement of the cells into one or more desired branch channels or outlet regions.

A "forward" sorting algorithm, according to the invention, includes embodiments where droplets from a droplet extrusion region flow through the device to a predetermined branch or outlet channel (which can be called a "waste channel"), until the level of measurable reporter of a molecule, cell or virion within a droplet is above a pre-set threshold. At that time, the flow is diverted to deliver the droplet (and the molecule, cell or virion contained therein) to another channel. For example, in an electro-osmotic embodiment, where switching is virtually instantaneous and throughput is limited by the highest voltage, the voltages are temporarily changed to divert the chosen droplet to another predetermined outlet channel (which can be called a "collection channel"). Sorting, including synchronizing detection of a reporter and diversion of the flow, can be controlled by various methods including computer or microprocessor control. Different algorithms for sorting in the microfluidic device can be implemented by different computer programs, such as programs used in conventional FACS devices. For example, a programmable card can be used to control switching, such as a Lab PC 1200 Card, available from National Instruments, Austin, Tex. Algorithms as sorting procedures can be programmed using C++, LAB VIEW, or any suitable software.

A "reversible" sorting algorithm can be used in place of a "forward" mode, for example in embodiments where switching speed may be limited. For example, a pressure-switched scheme can be used instead of electro-osmotic flow and does not require high voltages and may be more robust for longer runs. However, mechanical constraints may cause the fluid switching speed to become rate-limiting. In a pressure-switched scheme the flow is stopped when a molecule or cell or virion of interest is detected within a droplet. By the time the flow stops, the droplet containing the molecule, cell or virion may be past the junction or branch point and be part of the way down the waste channel. In this situation, a reversible embodiment can be used. The system can be run backwards at a slower (switchable) speed (e.g., from waste to inlet), and the droplet is then switched to a different branch or collection channel. At that point, a potentially mis-sorted droplet (and the molecule, cell or virion therein) is "saved", and the device can again be run at high speed in the forward direction. This "reversible" sorting method is not possible with standard FACS machines. FACS machines mostly sort aerosol droplets which cannot be reversed back to the chamber, in order to be redirected. The aerosol droplet sorters are virtually irreversible. Reversible sorting is particularly useful for identifying molecules, cells or virions that are rare (e.g., in molecular evolution and cancer cytological identification) or few in number, which may be misdirected due to a margin of error inherent to any fluidic device. The reversible nature of the device of the invention permits a reduction in this possible error.

In addition, a "reversible" sorting method permits multiple time course measurements of a molecule, cell or virion contained within a single droplet. This allows for observations or measurements of the same molecule, cell or virion at different times, because the flow reverses the cell back into the detection window again before redirecting the cell into a different channel. Thus, measurements can be compared or confirmed, and changes in properties over time can be examined, for example in kinetic studies.

When trying to separate molecules, cells or virions in a sample at a very low ratio to the total number of molecules, cells or virions, a sorting algorithm can be implemented that is not limited by the intrinsic switching speed of the device. Consequently, the droplets flow at the highest possible static (non-switching) speed from the inlet channel to the waste channel. Unwanted droplets (i.e., containing unwanted molecules, cells or virions) can be directed into the waste channel at the highest speed possible, and when a droplet containing a desired molecule, cell or virion is detected, the flow can be slowed down and then reversed, to direct the droplet back into the detection region, from where it can be redirected (i.e. to accomplish efficient switching). Hence the droplets (and the molecules, cells or virions contained therein) can flow at the highest possible static speed.

Preferably, both the fluid comprising the droplets and the fluid carrying the droplets (i.e., the aqueous and non-polar fluids) have a relatively low Reynolds Number, for example $10^{-2}$. The Reynolds Number represents an inverse relationship between the density and velocity of a fluid and its viscosity in a channel of given length. More viscous, less dense, slower moving fluids over a shorter distance will have a lower Reynolds Number, and are easier to divert, stop, start, or reverse without turbulence. Because of the small sizes and slow velocities, microfabricated fluid systems are often in a low Reynolds number regime (Re<<1). In this regime, inertial effects, which cause turbulence and secondary flows, are negligible; viscous effects dominate the dynamics. These conditions are advantageous for sorting, and are provided by microfabricated devices of the invention. Accordingly the microfabricated devices of the invention are preferably if not exclusively operated at a low or very low Reynold's number.

Exemplary sorting schemes are shown diagrammatically in FIGS. 14A and B and FIGS. 15A and B.

The invention is further described below, by way of the following examples. The examples include descriptions of particular, exemplary embodiments of the devices and methods of the present invention, including particular embodiments of channel architectures, valves, switching and flow control devices and methods which may be implemented as part of the devices and methods of the invention. The examples are provided for illustrative purposes only and are not limiting of the above-described invention in any way. For example, many of these specific embodiments are described and discussed primarily in terms of detecting and sorting cells suspended directly in the fluid that flows through a main channel of the device. Nevertheless, it will be appreciated by persons of ordinary skill in the art that these preferred embodiments are merely illustrative and that the invention may be practiced in a variety of embodiments that share the same inventive concept. In particular, the devices and methods described in this example (including the channel architectures, valves, switching and flow control devices and methods) may be readily adapted to a multi-phased device so that droplets which contain, e.g., molecules, cells or virions may be analyzed and/or sorted as desired by a user.

EXAMPLE 1

Microfabrication of a Silicon Device

Analytical devices having microscale flow channels, valves and other elements can be designed and fabricated from a solid substrate material. Silicon is a preferred substrate material due to well-developed technology permitting its precise and efficient fabrication, but other materials may be used, including polymers such as polytetrafluoroethylenes. Micromachining methods well known in the art include film deposition processes, such as spin coating and chemical vapor deposition, laser fabrication or photolithographic techniques, or etching methods, which may be performed by either wet chemical or plasma processes. See, e.g., (22) and (23).

FIGS. 1A-1D illustrate the initial steps in microfabricating the channels and discrimination region of a cell sorting device of the invention by photolithographic techniques. As shown, the structure includes a silicon substrate 160. The silicon wafer which forms the substrate is typically washed in a 4:1 $H_2SO_4/H_2O_2$ bath, rinsed in water, and spun dry. A layer 162 of silicon dioxide, preferably about 0.5 μm in thickness, is formed on the silicon, typically by heating the silicon wafer to 800 to 1200 degrees C. in an atmosphere of steam. The oxide layer is then coated with a photoresist layer 164, preferably about 1 μm in thickness. Suitable negative- or positive-resist materials are well known. Common negative-resist materials include two-component bisarylazide/rubber resists. Common positive-resist materials include polymethyl-methacrylate (PMMA) and two component diazoquinone/phenolic resin materials. See, e.g., (36).

The coated laminate is irradiated through a photomask 166 which has been imprinted with a pattern corresponding in size and layout to the desired pattern of the microchannels. Methods for forming photomasks having desired photomask patterns are well known. For example, the mask can be prepared by printing the desired layout on an overhead transparency using a high resolution (3000 dpi) printer. Exposure is carried out on standard equipment such as a Karl Suss contact lithography machine.

In the method illustrated in FIGS. 7A-7D, the photoresist is a negative resist. Thus, exposure of the resist to a selected wavelength, e.g., UV light, produces a chemical change that renders the exposed resist material resistant to the subsequent etching step. Treatment with a suitable etchant removes the unexposed areas of the resist, leaving a pattern of bare and resist-coated silicon oxide on the wafer surface, corresponding to the layout and dimensions of the desired microstructures. In this embodiment, since a negative resist is used, the bare areas correspond to the printed layout on the photomask. The wafer is next treated with a second etchant material, such as a reactive ion etch (RIE), which effectively dissolves the exposed areas of silicon dioxide. The remaining resist is removed, typically with hot aqueous $H_2SO_4$. The remaining pattern of silicon dioxide 162 now serves as a mask for the silicon 160. The channels are etched in the unmasked areas of the silicon substrate by treating with a KOH etching solution. Depth of etching is controlled by time of treatment. Additional microcomponents may also be formed within the channels by further photolithography and etching steps, as discussed below.

Depending on the method to be used for directing the flow of cells through the device, e.g., electro-osmotic or microvalve, electrodes and/or valves are fabricated into the flow channels. A number of different techniques are available for applying thin metal coatings to a substrate in a desired pattern. These are reviewed, for example, in (25). A convenient and common technique used in fabrication of microelectronic circuitry is vacuum deposition. For example, metal electrodes or contacts may be evaporated onto a substrate using vacuum deposition and a contact mask made from, for example, a "MYLAR" sheet. Various metals such as platinum, gold, silver or indium/tin oxide may be used for the electrodes.

Deposition techniques allowing precise control of the area of deposition are preferred when applying electrodes to the side walls of the channels in the device of the invention. Such techniques are described, for example, in (25) and the references cited therein. These techniques include plasma spraying, where a plasma gun accelerates molten metal particles in a carrier gas towards the substrate, and physical vapor deposition using an electron beam to deliver atoms on line-of-sight to the substrate from a virtual point source. In laser coating, a laser is focused onto the target point on the substrate, and a carrier gas projects powdered coating material into the beam, so that the molten particles are accelerated toward the substrate. Another technique allowing precise targeting uses an electron beam to induce selective decomposition of a previously deposited substance, such as a metal salt, to a metal. This technique has been used to produce submicron circuit paths, e.g., (26).

EXAMPLE 2

Photodiode Detectors

Figure 2A:
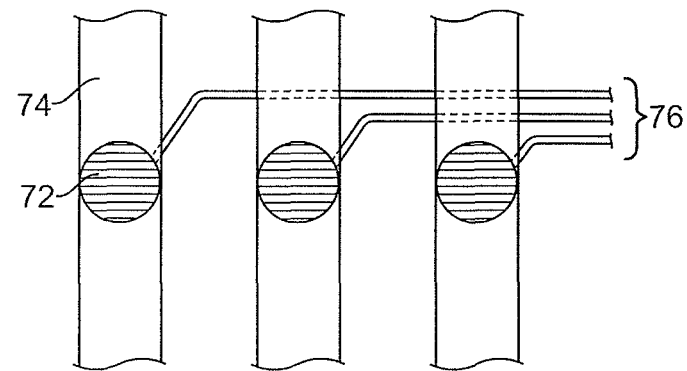
FIG. 2A shows one embodiment of a detection region used in a sorting device, having an integrated photodiode detector.

In one embodiment of the invention, shown in FIG. 2A, each detection region is formed from a portion of a channel 74 of an analysis unit and includes a photodiode 72 preferably located in the floor of the main channel. The detection region encompasses a receptive field of the photodiode in the channel, which receptive field has a circular shape. The volume of the detection region is the volume of a cylinder with a diameter equal to the receptive field of the photodiode and a height equal to the depth of the channel above the photodiode.

The signals from the photodiodes 72 can be carried to a processor via one or more lines 76, representing any form of electrical communication (including e.g. wires, conductive lines etched in the substrate, etc.). The processor acts on the signals, for example by processing them into values for comparison with a predetermined set of values for sorting the cells. In one embodiment, the values correspond to the amount of optically detectable signal emitted from a cell, which is indicative of a particular cell type or characteristic giving rise to the signal. The processor uses this information (i.e., the values) to control active elements in the discrimination region to determine how to sort the cells (e.g. electroosmotic switching or valve action).

When more than one detection region is used, the photodiodes in the laser diode chip are preferably spaced apart relative to the spacing of the detection regions in the analysis unit. That is, for more accurate detection, the photodiodes are placed apart at the same spacing as the spacing of the detection region.

The processor can be integrated into the same chip that contains the analysis unit(s), or it can be separate, e.g., an independent microchip connected to the analysis unit-containing chip via electronic leads that connect to the detection region(s) and/or to the discrimination region(s), such as by a photodiode. The processor can be a computer or microprocessor, and is typically connected to a data storage unit, such as computer memory, hard disk, or the like, and/or a data output unit, such as a display monitor, printer and/or plotter.

The types and numbers of cells, based on detection of a reporter associated with or bound to the cells passing through the detection region, can be calculated or determined, and the data obtained can be stored in the data storage unit. This information can then be further processed or routed to the data outlet unit for presentation, e.g. histograms, of the types of cells or levels of a protein, saccharide, or some other characteristic on the cell surface in the sample. The data can also be presented in real time as the sample is flowing through the device.

Figure 2B:
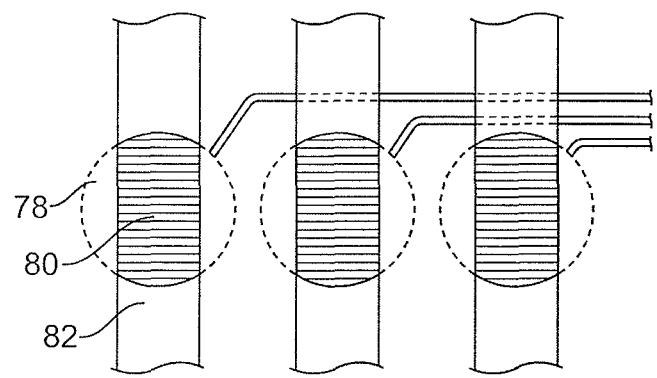
FIG. 2B shows another embodiment of a detection region, having an integrated photodiode detector, and providing a larger detection volume than the embodiment of FIG. 2A.

In the embodiment of FIG. 2B, the photodiode 78 is larger in diameter than the width of the channel 82, forming a detection region 80 that is longer (along the length of channel 82) than it is wide. The volume of such a detection region is approximately equal to the cross-sectional area of the channel above the diode multiplied by the diameter of the diode.

If desired, the device may contain a plurality of analysis units, i.e., more than one detection and discrimination region, and a plurality of branch channels which are in fluid communication with and branch out from the discrimination regions. It will be appreciated that the position and fate of the cells in the discrimination region can be monitored by additional detection regions installed, for example, immediately upstream of the discrimination region and/or within the branch channels immediately downstream of the branch point. The information obtained by the additional detection regions can be used by a processor to continuously revise estimates of the velocity of the cells in the channels and to confirm that cells having a selected characteristic enter the desired branch channel.

A group of manifolds (a region consisting of several channels which lead to or from a common channel) can be included to facilitate movement of the cell sample from the different analysis units, through the plurality of branch channels and to the appropriate solution outlet. Manifolds are preferably microfabricated into the chip at different levels of depth. Thus, devices of the invention having a plurality of analysis units can collect the solution from associated branch channels of each unit into a manifold, which routes the flow of solution to an outlet. The outlet can be adapted for receiving, for example, a segment of tubing or a sample tube, such as a standard 1.5 ml centrifuge tube. Collection can also be done using micropipettes.

EXAMPLE 3

Valve Structures

Figure 3A:
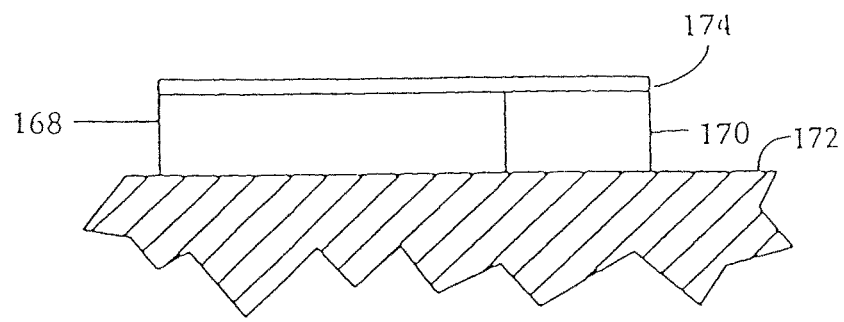
FIGS. 3A and 3B show one embodiment of a valve within a branch channel of a sorting device, and steps in fabrication of the valve.
Figure 3B:
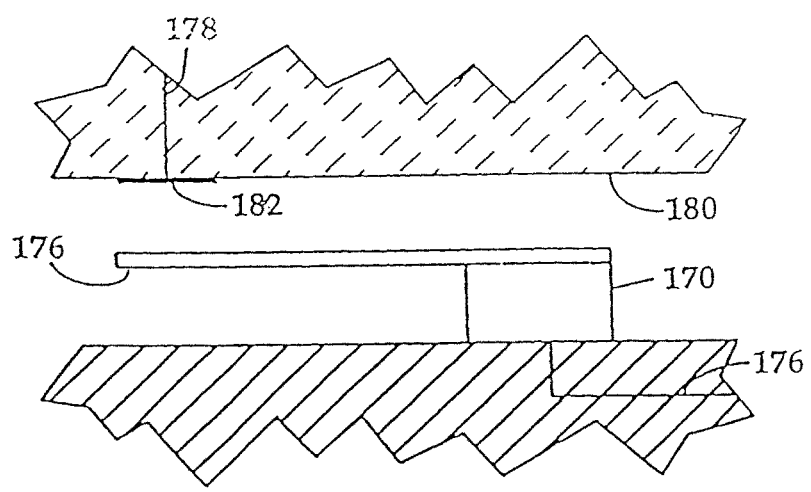

In an embodiment where pressure separation is used for discrimination of cells, valves can be used to block or unblock the pressurized flow of cells through selected channels. A thin cantilever, for example, may be included within a branch point, as shown in FIGS. 3A and 3B, such that it may be displaced towards one or the other wall of the main channel, typically by electrostatic attraction, thus closing off a selected branch channel. Electrodes are on the walls of the channel adjacent to the end of the cantilever. Suitable electrical contacts for applying a potential to the cantilever are also provided in a similar manner as the electrodes.

A valve within a channel may be microfabricated, if desired, in the form of an electrostatically operated cantilever or diaphragm. Techniques for forming such elements are well known in the art (e.g., 28, 40, 41, 24, 22). Typical processes include the use of selectively etched sacrificial layers in a multilayer structure or, for example, the undercutting of a layer of silicon dioxide via anisotropic etching. For example, to form a cantilever within a channel, as illustrated in FIGS. 3A and 3B, a sacrificial layer 168 may be formed adjacent to a small section of a non-etchable material 170, using known photolithography methods, on the floor of a channel, as shown in FIG. 3A. Both layers can then be coated with, for example, silicon dioxide or another non-etchable layer, as shown at 172. Etching of the sacrificial layer deposits the cantilever member 174 within the channel, as shown in FIG. 3B. Suitable materials for the sacrificial layer, non-etchable layers and etchant include undoped silicon, p-doped silicon and silicon dioxide, and the etchant EDP (ethylene diamine/pyrocatechol), respectively. Because the cantilever in FIG. 3B is parallel to the direction of etching, it may be formed of a thin layer of silicon by incorporating the element into the original photoresist pattern. The cantilever is preferably coated with a dielectric material such as silicon nitride, as described in (41) for example, to prevent short circuiting between the conductive surfaces.

It will be apparent to one of skill in the field that other types of valves or switches can be designed and fabricated, using well known photolithographic or other microfabrication techniques, for controlling flow within the channels of the device. Multiple layers of channels can also be prepared.

EXAMPLE 4

Sorting Techniques

As illustrated with respect to FIGS. 4A-4D, there are a number of ways in which cells can be routed or sorted into a selected branch channel.

FIG. 4A shows a discrimination region 102, which is suitable for electrophoretic discrimination as the sorting technique. The discrimination region is preceded by a main channel 104. A junction divides the main channel into two branch channels 106 and 108. The discrimination region 102 includes electrodes 110 and 112, positioned on outer side walls of the branch channels 106 and 108, and which connect to leads 114 and 116. The leads are connected to a voltage source (not shown) incorporated into or controlled by a processor (not shown), as described, infra. The distance (D) between the electrodes is preferably less than the average distance separating the cells during flow through the main channel. The dimensions of the electrodes are typically the same as the dimensions of the channels in which they are positioned, such that the electrodes are as high and wide as the channel.

The discrimination region shown in FIG. 4B is suitable for use in a device that employs electro-osmotic flow, to move the cells and bulk solution through the device. FIG. 4B shows a discrimination region 122 which is preceded by a main channel 124. The main channel contains a junction that divides the main channel into two branch channels 126 and 128. An electrode 130 is placed downstream of the junction of the main channel, for example near the sample inlet of main channel. Electrodes are also placed in each branch channel (electrodes 132 and 134). The electrode 130 can be negative and electrodes 132 and 134 can be positive (or vice versa) to establish bulk solution flow according to well-established principles of electro-osmotic flow (32).

After a cell passes the detection region (not shown) and enters the discrimination region 122 (e.g. between the main channel and the two branch channels) the voltage to one of the electrodes 132 or 134 can be shut off, leaving a single attractive force that acts on the solution and the cell to influence it into the selected branch channel. As above, the appropriate electrodes are activated after the cell has committed to the selected branch channel in order to continue bulk flow through both channels. In one embodiment, the electrodes are charged to divert the bulk flow of cells into one branch channel, for example channel 126, which can be called a waste channel. In response to a signal indicating that a cell has been identified or selected for collection, the charge on the electrodes can be changed to divert the selected sell into the other channel (channel 128), which can be called a collection channel.

In another embodiment of the invention, shown in FIG. 4C, the cells are directed into a predetermined branch channel via a valve 140 in the discrimination region. The valve 140 comprises a thin extension of material to which a charge can be applied via an electrode lead 142. The valve 140 is shown with both channels open, and can be deflected to close either branch channel by application of a voltage across electrodes 144 and 146. A cell is detected and chosen for sorting in the detection region (not shown), and can be directed to the appropriate channel by closing off the other channel, e.g. by applying, removing or changing a voltage applied to the electrodes. The valve can also be configured to close one channel in the presence of a voltage, and to close the other channel in the absence of a voltage.

FIG. 4D shows another embodiment of a discrimination region of the invention, which uses flow stoppage in one or more branch channels as the discrimination means. The sample solution moves through the device by application of positive pressure at an end where the solution inlet is located. Discrimination or routing of the cells is affected by simply blocking a branch channel 145 or 148 or a branch channel sample outlet using valves in a pressure-driven flow 147 or 149. Due to the small size scale of the channels and the incompressibility of liquids, blocking the solution flow creates an effective "plug" in the non-selected branch channel, thereby temporarily routing the cell together with the bulk solution flow into the selected channel. Valve structures can be incorporated downstream from the discrimination region, which are controlled by the detection region, as described herein.

Alternatively, the discrimination function represented in FIG. 4D may be controlled by changing the hydrostatic pressure at the sample outlets of one or both branch channels 145 or 148. If the branch channels in a particular analysis unit have the same resistance to fluid flow, and the pressure at the sample inlet of the main channel of an analysis unit is P, then the fluid flow out of any selected branch channel can be stopped by applying a pressure P/n at the sample outlet of the desired branch channel, where n is the number of branch channels in the analysis unit. Accordingly, in an analysis unit having two branch channels, the pressure applied at the outlet of the branch to be blocked is P/2.

As shown in FIG. 4D, a valve is situated within each branch channel, rather than at the branch point, to close off and terminate pressurized flow through selected channels. Because the valves are located at a point downstream from the discrimination region, the channels in this region may be formed having a greater width than in the discrimination region in order to simplify the formation of valves. The width of the cantilever or diaphragm should approximately equal the width of the channel, allowing for movement within the channel. If desired, the element may be coated with a more malleable material, such as a metal, to allow for a better seal. Such coating may also be employed to render a non-conductive material, such as silicon dioxide, conductive. As above, suitable electrical contacts are provided for displacing the cantilever or diaphragm towards the opposing surface of the channel. When the upper surface is a glass cover plate, electrodes and contacts may be deposited onto the glass.

Figure 5:
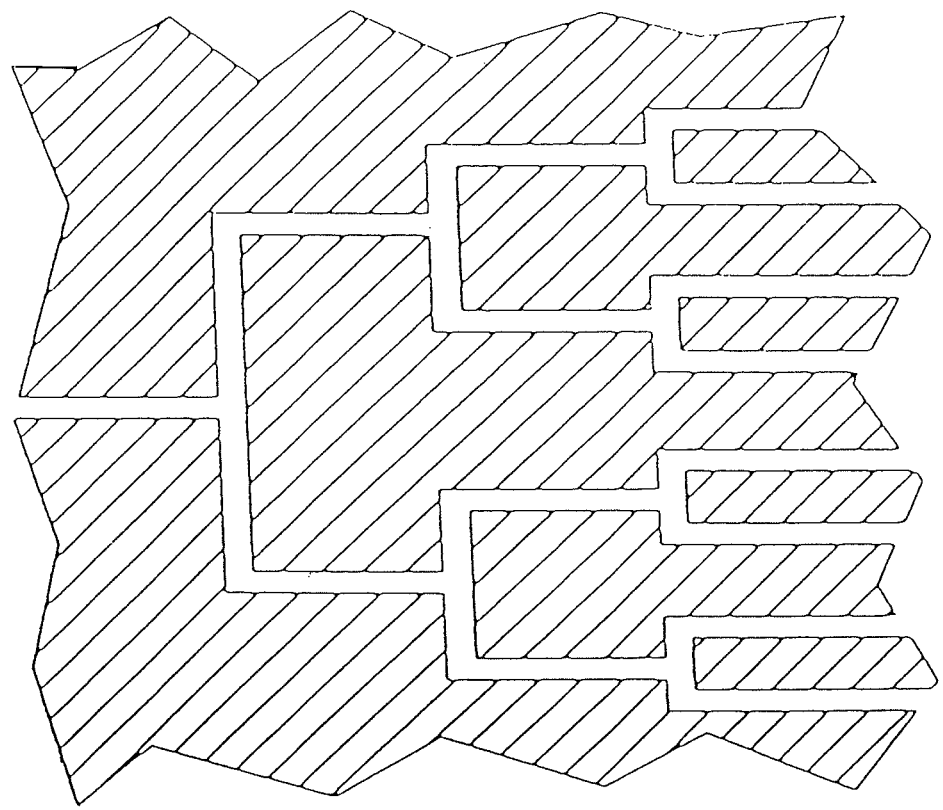
FIG. 5 shows a device with analysis units containing a cascade of detection and discrimination regions suitable for successive rounds of sorting.

FIG. 5 shows a device with analysis units containing a cascade of detection and discrimination regions suitable for successive rounds of cell sorting. For example, such a cascade configuration may be used to sequentially assay the cells for at least three different reporters, e.g., fluorescent dyes, corresponding to expression of at least three different cellular characteristics (markers). Samples collected at the outlet region of the different branch channels contain pools of cells expressing defined levels of each of the three markers. The number of reporters employed, and therefore the number of expressed markers of interest, can be varied to meet the needs of the practitioner.

EXAMPLE 5

Reporters and Labels for Cell Sorting

To sort cells of the invention, cells are labeled with an optically detectable reporter which is analyzed and interpreted to determine whether the cell having the reporter should be sorted. The reporter may function in a variety of ways to effectively emit or display a readable signal that can be detected by the detection region.

In one embodiment the signal is in the form of a marker that associates within or binds to a particular cell type. The signal therefore acts to identify the cell as having a particular characteristic, e.g., a protein (receptor) or saccharride, such that the reporter signal from a given cell is proportional to the amount of a particular characteristic. For example, the reporter may be an antibody, a receptor or a ligand to a receptor (which bind to a protein or sugar), or a fragment thereof, each having a detectable moiety, such as a dye that fluoresces. The reporter can bind to a structure on the surface or within the cell of interest, and since the antibody contains a detectable reporter, any cell to which the reporter is bound would be detectable by the detection region of the device as the cell flows past such region. It should be appreciated by those having ordinary skill in the art that the antibody, receptor, ligand, or other agent that can act as a marker, can be modified to meet the needs of the practitioner, e.g., such as using fragments or making chimerics.

Fluorescent dyes are examples of optically-detectable reporters. There are a number of known dyes which selectively bind to nucleic acids, proteins and sugars. For DNA and RNA studies, these include, but are not limited to, Hoechst 33258, Hoechst 33342, DAPI (4',6-diamidino-2-phenylindoleHCl), propidium iodide, dihydroethidium, acridine orange, ethidium bromide, ethidium homodimers (e.g., EthD-1, EthD-2), acridine-ethidium heterodimer (AEthD) and the thiazole orange derivatives PO-PRO, BOPRO, YO-PRO, To-PRO, as well as their dimeric analogs POPO, BOBO, YOYO, and TOTO. All of these compounds can be obtained from Molecular Probes (Eugene, Oreg.). Extensive information on their spectral properties, use, and the like is provided in Haugland (30). Each dye binds at a known or empirically determined maximum density. Thus, by measuring the fluorescence intensity of a reporter molecule, the presence, concentration or relative amount of the desired cell characteristic can be determined, for example by comparison with an empirically determined reference standard. For example, one molecule of YOYO-1 has been found to bind 4-5 base pairs of DNA, and this ratio can be used to evaluate the length of an unknown DNA sequence, or to sort DNA based on a range or window of dye signal corresponding to a desired sorting length.

Ultraviolet reporters may also be used. Examples include green fluorescent protein and cascade blue.

Two applications of the invention are for the quantitation of cell surface and intracellular antigens, and of nucleic acid contents in cells, for the study of cellular differentiation and function, e.g. in the field of immunology and cancer cytology. For cellular surface antigen studies, phycobiliproteins, phycoerythrin, Texas Red and allophycocyanin, can be used as fluorescent labels for monoclonal antibodies for identification of blood cells and cancer cells. For cellular DNA/RNA analysis, the dyes mentioned above can be used. For the study of cellular functions, chromogenic or fluorogenic substrates were first used in flow cytometry to detect and quantitate intracellular enzyme activities (e.g., 4-Nitrophenyl, 5-Bromo-5-chloro-3-indolyl, fluorescein digalactoside, fluorescein diglucuronide, fluorescein diphosphate, and creatine phosphate.) These reporters can be used in the invention.

Dyes and fluorescent substrates for detection of other cellular functions such as protein contents (dyes e.g., fluorescein isothoiocyanate, sulphorhodamine, sulfosuccinimidyl esters, fluorescein-5-maleimide), intracellular pH (such as carboxyfluorescein and its derivative esters, and fluorescein sulfonic acid and its derivative diacetate), for signal transduction (e.g., fluorescent bisindolylmaleimides, hypericin, hypocrellin, forskolin) cytoplasmic and mitochondrial membrane potentials developed for analysis of cellular activation processes can also be used. Other applications suitable for use in the invention include chromogenic or fluoregenic probes for analysis of other cellular or encapsulating environments, such as detection of organelles (e.g. the mitochondria, lysosomes), cell morphology, cell viability and proliferation, receptors and ion channels, and for measurements of certain ions (e.g. metal ions, $Ca^{2+}$, $Mg^{2+}$, $Zn^{2+}$) in the cells or in the environment. Probes of the kinds described here be obtained for example from Molecular Probes (Eugene, Oreg.).

In another embodiment, cells may produce a reporter in vivo (e.g. a fluorescent compound) through interaction with a reagent added to the fluid medium. For example, cells containing a gene for an oxygenase enzyme may catalyze a reaction on an aromatic substrate (e.g. benzene or naphthalene) with the net result that the fluorescence, or another detectable property of the substrate, will change. This change can be detected in the detection region, and cells having that change in fluorescence can be collected based on predetermined criteria. For example, cells that produce a desired monooxygenase enzyme (such as a P450 enzyme) can be detected in the presence of a suitable substrate (such as naphthalene), and can be collected according to the invention, based on the ability of the enzyme to catalyze a reaction in which a detectable (e.g. fluorescent) product is produced from the substrate. Sorting can also be done based on a threshold or window concentration of reaction product, which in turn can be correlated with the level of fluorescence. A second reagent or coupling enzyme can be used to enhance fluorescence. See, Affholter and Arnold (34) and Joo et al. (35). Any mechanism of this kind, including any reporter or combinations of substrate, enzyme and product can be used for detection and sorting in a like manner, so long as there is at least one way to detect or measure the presence or degree of the reaction of interest.

The invention may be used to sort any prokaryotic (e.g., bacteria) or eukaryotic cells (e.g., mammalian, including human blood cells, such as human peripheral blood mononuclear cells (PBMCs)) which has a detectable characteristic or marker, or which can be labeled with a detectable reporter, for example an optically-detectable label. For example, antibodies or fragments thereof that recognize a receptor or antigen of interest, and which are linked to a fluorescent dye can be used to label cells. Examples of antigens which can be labeled with antibodies for cell sorting include, without limitation, HLA DR, CD3, CD4, CD8, CD11a, CD11c, CD14, CD16, CD20, CD45, CD45RA, and CD62L. The antibodies can in turn be detected using an optically-detectable reporter (either via directly conjugated reporters or via labeled secondary antibodies) according to methods known in the art. Alternatively, a ligand that is bound with a fluorescent dye and has affinity for a particular antigen or receptor of interest can be used in the same manner.

It will be appreciated that the cell sorting device and method described above can be used simultaneously with multiple optically-detectable reporters having distinct optical properties. For example, the fluorescent dyes fluorescein (FITC), phycoerythrin (PE), and "CYCHROME" (Cy5-PE) can be used simultaneously due to their different excitation and emission spectra. The different dyes may be assayed, for example, at successive detection and discrimination regions. Such regions may be cascaded as shown in FIG. 5 to provide samples of cells having a selected amount of signal from each dye.

Optical reporters, such as fluorescent moieties, can be excited to emit light of characteristic wavelengths by an excitation light source. Fluorescent moieties have an advantage in that each molecule can emit a large number of photons to a distance of 10 feet in response to radiation stimulus. Other optically detectable reporter labels include chemiluminescent and radioactive moieties, which can be used without an excitation light source. In another embodiment, absorbance at a particular wavelength, or measuring the index refraction of a particle, such as a cell, can be used to detect a characteristic. For example, if using an index of refraction, different types of cells can be distinguished by comparing differences in their retractive properties as they pass a light source.

EXAMPLE 6

Operation of a Microfabricated Cell Sorting Device

In operation of the microfabricated device of the invention, it is advantageous and preferred, to "hydrate" the device (i.e., fill the channels of the device with a solvent, such as water or the buffer solution in which the cells will be suspended) prior to introducing the cell-containing solution. Hydration of the device can be achieved by supplying the solvent to the device reservoir and applying hydrostatic pressure to force the fluid through the analysis unit(s).

Following the hydration step, the cell-containing solution is introduced into the sample inlets of the analysis unit(s) of the device. The solution may be conveniently introduced in a variety of ways, including by an opening in the floor of the inlet channel, reservoir (well) or via a connector. As a stream of cells to be sorted for a detectable characteristic or reporter is moved through the detection region, a signal from each cell is detected or measured and is compared with a threshold or set range of values to determine whether the cell possesses the desired characteristic based on the amount of reporter detected. The cells preferably move in single file.

In the embodiment of this example, the level of reporter signal is measured at the detection region using an optical detector, which may include one or more of a photodiode (e.g., avalanche photodiode), a fiber-optic light guide leading, for example, to a photo multiplier tube, a microscope with a high numerical aperture objective and an intensified video camera, such as a CCD camera, or the like. The optical detector may be microfabricated or placed onto a cell analysis chip (e.g., a photodiode as illustrated in FIGS. 2A and 2B), or it may be a separate element, such as a microscope objective.

If the optical detector is used as a separate element, it is generally advantageous to restrict the collection of signal from the detection region of a single analysis unit at a given time. It may also be advantageous to provide an automated means of scanning the laser beam relative to the cell analysis chip, scanning the emitted light over the detector, or using a multichannel detector. For example, the cell analysis chip can be secured to a movable mount (e.g., a motorized/computer-controlled micromanipulator) and scanned under the objective. A fluorescence microscope, which has the advantage of a built-in excitation light source (epifluorescence), is preferably employed for detection of a fluorescent reporter.

The signal collected from the optical detector is routed, e.g., via electrical traces and pins on the chip, to a processor, which interprets the signals into values corresponding to the cell type characteristic giving rise to the signal. These values are then compared, by the processor, with pre-loaded instructions containing information about which branch channel the cells having the desired characteristic will be routed. In some embodiments there is a signal delay period (i.e., long enough to allow the reporter signal from the cell to reach the discrimination region), after which the processor sends a signal to actuate the active elements in the discrimination region to route the cell into the appropriate branch channel. In other embodiments there is little or no signal delay period, because the detection region is immediately adjacent to the branch point, and switching can be immediate. There may be a sorting delay period, which is the time needed to ensure that a selected cell is sorted into the correct branch channel, i.e. before switching back to normal (non-selected) flow. This period can be empirically determined.

Any needed or desired delay period can be readily determined according to the rate at which the cells move through the channel, i.e. their velocity, and the length of the channel between the detection region and the discrimination region. In addition, depending on the mechanism of flow, cell size may also affect the movement (velocity) through the device. In cases where the sample solution is moved through the device using hydrostatic pressure (e.g., as pressure at the inlet region and/or suction at the outlet region), the velocity is typically the flow rate of the solution. If the cells are directed through the device using some other force, such as electro-osmotic flow (e.g. using an electric field or gradient between the inlet region and the outlet region), then the delay period is a function of velocity and cell size, and can be determined empirically by running standards including different sizes or types of known cells. Thus, the device can be appropriately calibrated for the intended use.

The time required to isolate a desired quantity of cells depends on a number of factors, including the size of the cells, the rate at which each analysis unit can process the individual fragments, and the number of analysis units per chip. The time required can be calculated using known formulas. For example, a chip containing 1000 analysis units, each of which can sort 1,000 cells per second, could isolate about 100 µg of 3 µm cells in about 1 hour.

The concentration of cells in the sample solution can influence sorting efficiency, and can be optimized. The cell concentration should be dilute enough so that most of the cells pass through the detection region one by one (in single file), with only a small statistical chance that two or more cells pass through the region simultaneously. This is to insure that for the large majority of measurements, the level of reporter measured in the detection region corresponds to a single cell and not two or more cells.

The parameters which govern this relationship are the volume of the detection region and the concentration of cells in the sample solution. The probability that the detection region will contain two or more cells ($P_{\geq 2}$) can be expressed as $$P_{\geq 2} = 1 - \{1 + [\text{cell}] \times V\} \times e^{-[\text{cell}] \times V}$$

where [cell] is the concentration of cells in units of cells per $\mu m^3$ and V is the volume of the detection region in units of $\mu m^3$.

It will be appreciated that $P_{\geq 2}$ can be minimized by decreasing the concentration of cells in the sample solution. However, decreasing the concentration of cells in the sample solution also results in an increased volume of solution processed through the device and can result in longer run times. Accordingly, it is desirable to minimize the presence of multiple cells in the detection chamber (thereby increasing the accuracy of the sorting) and to reduce the volume of sample fluid thereby permitting a sorted sample in a reasonable time in a reasonable volume containing an acceptable concentration of cells.

The maximum tolerable $P_{\geq 2}$ depends on the desired "purity" of the sorted sample. The "purity" in this case refers to the fraction of sorted cells that are in a specified size range, and is inversely proportional to $P_{\geq 2}$. For example, in applications where high purity is not needed or desired a relatively high $P_{\geq 2}$ (e.g., $P_{\geq 2}=0.2$) may be acceptable. For most applications, maintaining $P_{\geq 2}$ at or below about 0.1, preferably at or below about 0.01, provides satisfactory results.

For example, where $P_{\geq 2}$ is 0.1, it is expected that in about 10% of measurements, the signal from the detection region is a result of the presence of two or more cells. If the total signal from these cells is in the range corresponding to a value set for a desired cell type, those cells will be sorted into the channel or tube predetermined for the desired cell type.

The cell concentration needed to achieve a particular $P_{\geq 2}$ value in a particular detection volume can be calculated from the above equation. For example, a detection region in the shape of a cube 10 microns per side has a volume of 1 pl. A concentration of cells which have a diameter of 1 micron, resulting on average in one cell per pl, is about 1.7 pM. Using a $P_{\geq 2}$ value of about 0.01, the cell concentration in a sample analyzed or processed using the 1 pl detection region volume is approximately 10 pM, or roughly one cell per 3 detection volumes ([cell]×V=~0.3). If the concentration of cells is such that [cell]×V is 0.1, then $P_{\geq 2}$ is less than 0.005; i.e., there is less than a one half of one percent (0.5%) chance that the detection region will, at any given time, contain two or more cells.

As discussed above, the sample mixture introduced into a device of the invention should be dilute enough such that there is a high likelihood that only a single cell will occupy the detection region at any given time. This will allow the cells to be in "single file", separated by stretches of cell-free solution as the solution flows through the device between the detection and discrimination regions. The length of the channel, discussed above, between the detection and discrimination region should therefore not be too long, such that random thermal diffusion does not substantially alter the spacing between the cells. In particular, the channel length should be short enough so that a cell can traverse it in short enough time, such that even the smallest cells being analyzed will typically be unable to diffuse and change position or order in the line of cells. The channel should also be long enough so that flow control can be switched in time to appropriately divert a selected cell in response to detection or measurement of a signal produced from examination of the cell as it passes through the detection region.

The diffusion constant of a 0.5 m sphere is approximately $5 \times 10^{-9}$ cm$^2$/sec. The diffusion equation gives the distance (x) that the sphere will diffuse in time (t) as: $<x^2>=Dt$, where D is the diffusion constant given by $D=k_B T/6\pi\eta R_0$. In this equation, $k_b$ is the Boltzmann's Constant, T is the temperature, $\eta$ is the viscosity of the fluid and $R_0$ is the diameter of the sphere. Using this relationship, it will be appreciated that a 0.5 µm cell takes about 50 seconds to diffuse 500 µm. The average spacing of cells in the channel is a function of the cross-sectional area of the channel and the cell concentration, the latter typically determined in view of acceptable values of $P_{\geq 2}$, discussed above. From these relationships, it is then easy to calculate the maximum channel length between the detection and discrimination region which would ensure that cells do not change order or position in the line of cells. In practice, the channel length between the detection and discrimination regions is between about fpm and about 100 µm.

Shear forces may affect the velocity at which the cells move through the microfluidic device, particularly when living cells are to be sorted and collected. Experiments have shown that high electric fields, in the range of 2-4 kV/cm for human erythrocytes and 5-10 kV/cm for yeast cells can be used to introduce DNA and other substances into cells using electroporation. At these voltages there was no cell lysis, although membrane permeation was possible. To avoid membrane permeation and cell lysis, it is preferred that the electric fields applied to move cells in any of the described flow techniques is less than about 600 V/cm and most preferably less than about 100 V/cm.

EXAMPLE 7

Elastomeric Microfabricated Device

This Example demonstrates the manufacture and operation of a disposable microfabricated FACS device, which can function as a stand-alone device or as a component of an integrated microanalytical chip, in sorting cells or biological materials. The device permits high sensitivity, no cross-contamination, lower cost to operate and manufacture than conventional FACS machines and multiple-hour run times. In this example, the microfabricated chip had a detection volume of approximately 250 fl and single channel throughput of about 20 cells/second. The device obtained substantial enrichment of micron-sized fluorescent bead populations of different colors. In addition, populations of E. coli cells expressing green fluorescent protein were separated, and enriched, from a background of non-fluorescent (wild type) E. coli cells. The bacteria were also found to be viable after extraction from the sorting device.

Preparation of the Microfabricated Device

A silicon wafer was etched and fabricated as described above and in (12). After standard contact photolithography techniques to pattern the oxide surface of the silicon wafer, a $C_2F_2$/CHF$_3$ gas mixture was used to etch the wafer by RIE. The silicon wafer was then subjected to further etch with KOH to expose the silicon underneath the oxide layer, thereby forming a mold for the silicone elastomer. The silicon mold forms a "T" arrangement of channels. The dimensions of the channels may range broadly, having approximately 5×4 µm dimension.

Figure 6:
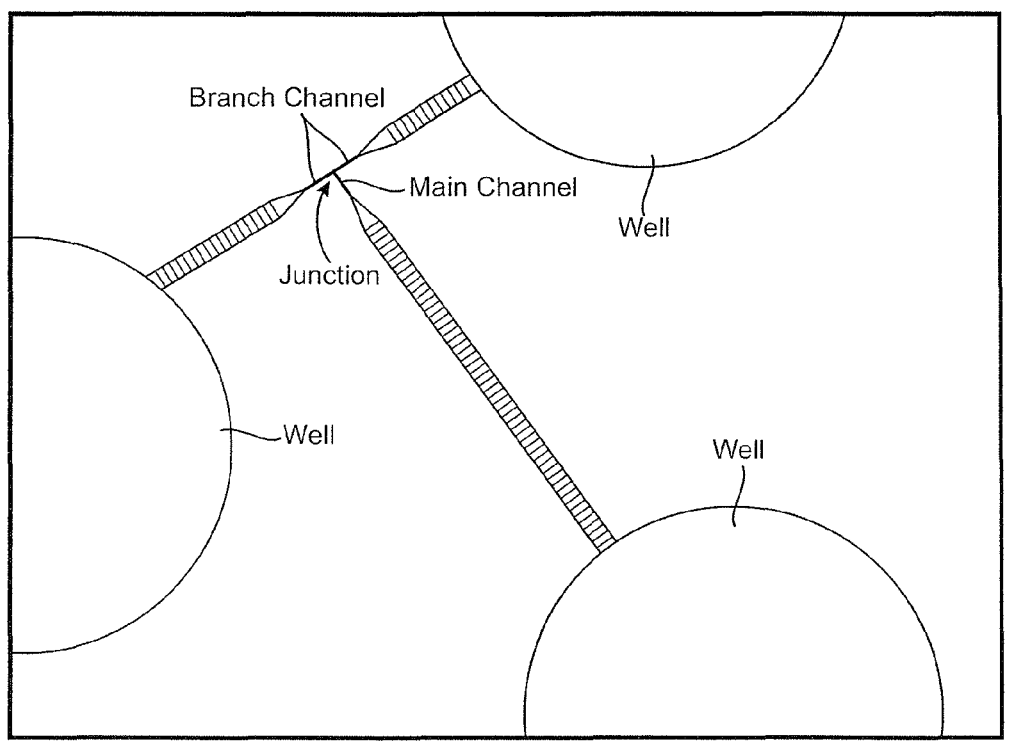
FIG. 6 is a photograph of an apparatus of the invention, showing a chip with an inlet channel and reservoir, a detection region, a branch point, and two outlet channels and reservoirs.

A representative device of the invention is shown in FIG. 6. The etching process is shown schematically in FIG. 7. Standard micromachining techniques were used to create a negative master mold out of a silicon wafer. The disposable silicone elastomer chip was made by mixing General Electric RTV 615 components (36) together and pouring onto the etched silicon wafer. After curing in an oven for two hours at 80° C., the elastomer was peeled from the wafer and bonded hermetically to a glass cover slip for sorting. To make the elastomer hydrophilic the elastomer chip was immersed in HCl (pH=2.7) at 60 degrees C. for 40 to 60 min. Alternatively, the surface could have been coated with polyurethane (3% w/v in 95% ethanol and diluted 10× in ethanol). It is noted that the master wafer can be reused indefinitely. The device shown has channels that are 100 µm wide at the wells, narrowing to 3 µm at the sorting junction (discrimination region). The channel depth is 4 µm, and the wells are 2 mm in diameter.

Figure 7:
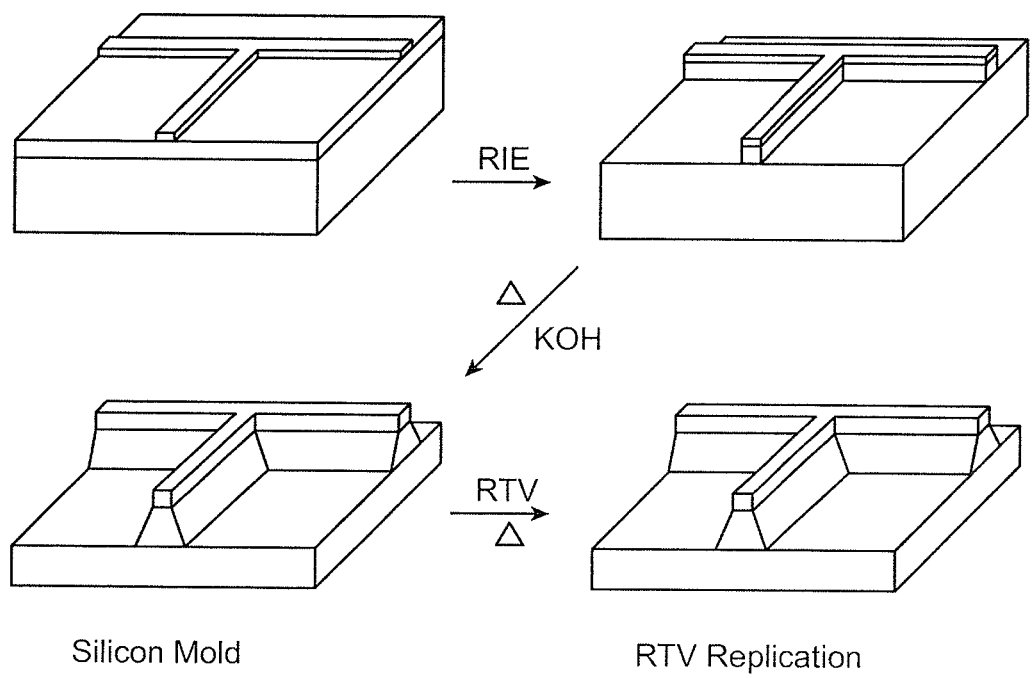
FIG. 7 shows a schematic representation of a process for obtaining a silicone elastomer impression of a silicon mold to provide a microfabricated chip according to the invention.
Figure 8:
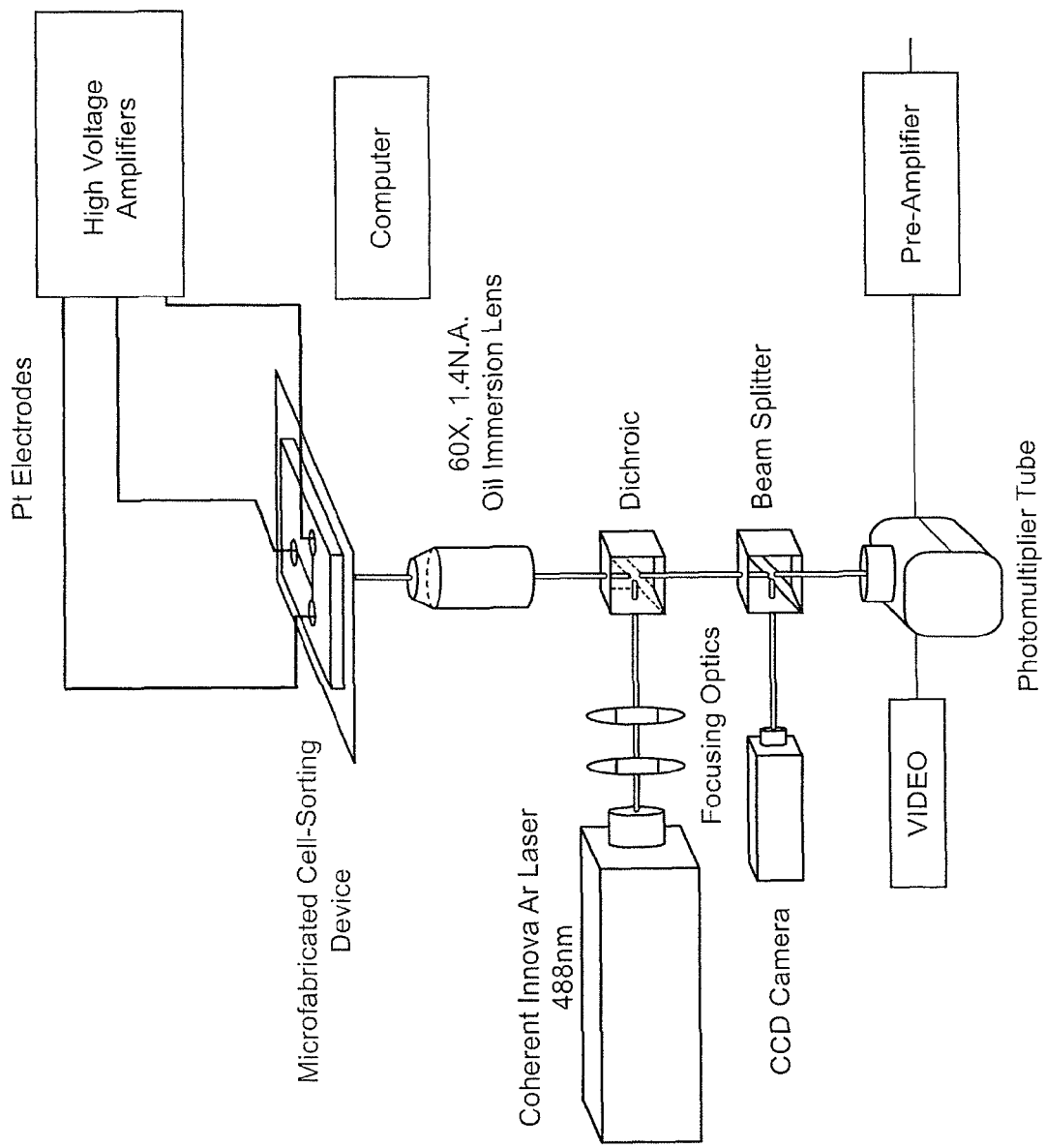
FIG. 8 shows a schematic representation of an apparatus of the invention, in which a silicone elastomer chip is mounted on an inverted microscope for optical detection of a laser-stimulated reporter. Electrodes are used to direct virions or cells in response to the microscope detection.

In this embodiment the cell-sorting device was mounted on an inverted optical microscope (Zeiss Axiovert 35) as shown in FIG. 8. In this system, the flow control can be provided by voltage electrodes for electro-osmotic control or by capillaries for pressure-driven control. The detection system can be photo multiplier tubes or photodiodes, depending upon the application. The inlet well and two collection wells were incorporated into the elastomer chip on three sides of the "T" forming three channels (FIGS. 6 and 7). The chip was adhered to a glass coverslip and mounted onto the microscope.

Three platinum electrodes were each inserted into separate wells. A water-cooled argon laser (for cells) or a 100 W mercury lamp (for beads) focused through an oil immersion objective (Olympus Plan Apo 60×1.4NA) was used to excite the fluorescence and a charge-coupled device (CCD) camera took the image. To select for red fluorescence emission a 630 nm±30 emission filter (Chroma) is used. The detection region was approximately 5 to 10 µm below the T-junction and has a window of approximately 15×5 µm dimension. The window is implemented with a Zeiss adjustable slit. Using one or two Hammatzu R928 photo multiplier tubes (bias −850V) with custom current-to-voltage amplifier, or using photodiodes, as detectors, and using different emission filters (depending on the fluorescence), photocurrent(s) from the detector(s) were converted to voltage by a Burr-Brown OP128 optical amplifier (10$^7$ V/A), digitized by National Instrument PC1200 board and processed into a computer. The voltages on the electrodes are provided by a pair of Apex PA42 HV op amps powered by Acopian power supplies. The third electrode was ground. Adjusting the voltage settings on the PC1200 board analog outlets and its amplification to the platinum electrodes can control the switching of the directions of the fluids. Thus, cells can be directed to either side of the "T" channels depending upon the voltage potential settings. Furthermore, different ways of sorting in the microfluidic device can be achieved by different computer programs, e.g., different computer-controlled procedures using known programming techniques.

Sorting Experiments

This embodiment of the microfabricated FACS system was used to sort fluorescent beads of different emission wavelengths in different ratios up to 33,000 beads per hour throughput (See FIGS. 9-12). Extra reservoir wells were incorporated into the outer side of the three wells of the chip in order to avoid ion-depletion, and platinum electrodes (with the ground electrode in the inlet well) were inserted into the reservoir wells. One micron diameter beads were suspended in PBS (137 mM NaCl, 2.7 mM KCl, 4.3 mM $Na_2HPO_4.7H_2O$, 1.4 mM $KH_2PO_4$) with 10% BSA (1 g/l) and 0.5% Tween 20 in various ratios and dilutions. Samples of the different colored fluorescent beads, having ratios as indicated below, were injected into the inlet well in 10 to 30 µl aliquots. The collection wells were filled with the same buffer.

To sort the beads the optical filter in front of the PMT passed only the color fluorescence corresponding to the color of the bead on interest, e.g., red fluorescent light to sort red beads. Voltages on the electrodes were set for switching purposes, either for sorting or reversible switching. The time duration of sorting can be as long as 3 hours, although the voltage settings may have to be readjusted from time to time. The coefficient of variation of bead intensity was measured as about 1 to 3% depending on the depth of the channel and the surface treatment of the elastomer. After sorting, enrichment of the beads was determined by the processor that recorded the data gathered by the detection region and was verified by counting.

In the following experiments, the channels of the microfabricated device were 3×4 with bead-sorting and 10×4 with cell-sorting.

A. Sorting Green Fluorescent Beads from Red Fluorescent Beads

As shown in FIG. 8, sorting of green fluorescent beads to red fluorescent beads in a ratio of 100:1 was performed. A mixture of 0.375% beads resuspended in 137 mM NaCl PBS with 10% BSA+0.5% Tw20 was put through the 3×4 µm silicone elastomer device of the invention for approximately 22 minutes. Using a mercury lamp as the light source, the R928Hammatzu PMT bias was −850 V with 630 nm±30 emission filter.

B. Sorting Red Fluorescent Beads from Blue Fluorescent in Forward and Reverse

Figure 9:
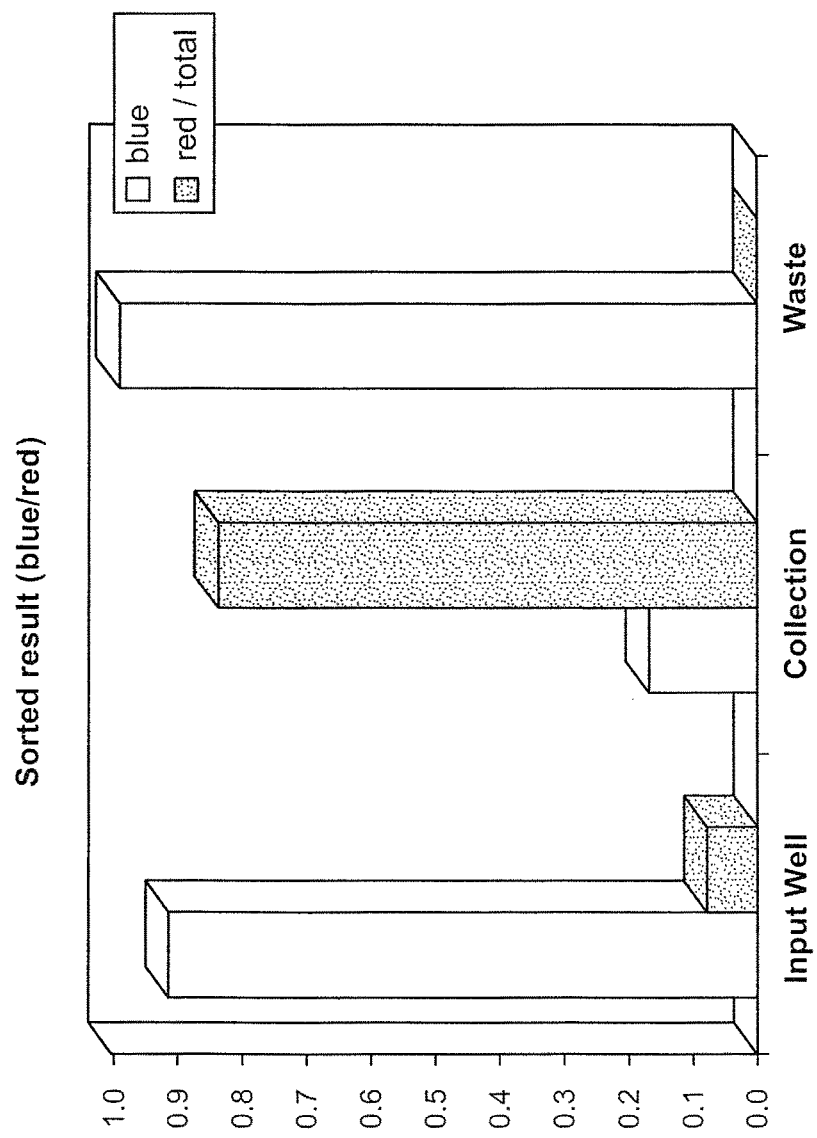
FIG. 9 shows the results of sorting blue and red fluorescent beads having an initial ratio of 10:1, respectively, using a forward mode. The darker bar represents the ratio of red beads over the total number of beads sorted and the lighter bar represents the ratio of blue beads over the total number of beads sorted.

FIG. 9 shows sorting of blue fluorescent beads to red fluorescent beads in a ratio of 10:1 using a forward mode. A mixture of 1.5% beads resuspended in 137 mM NaCl PBS with 10% BSA+0.5% Tw20 was sorted using a 3×4 µm device for about 24 minutes. Red beads were enriched 8.4 times. The darker and lighter bars represent the ratio of red or blue beads over the total number of beads sorted, respectively.

Figure 10:
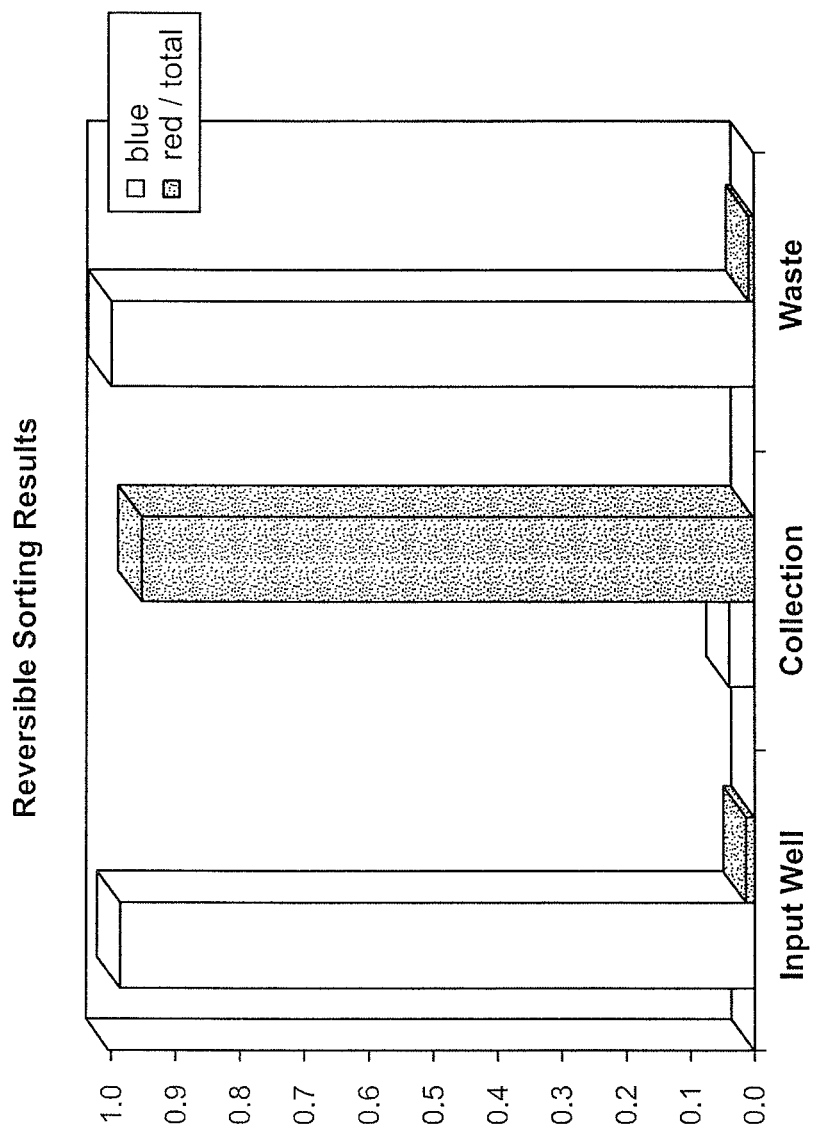
FIG. 10 shows the results of sorting blue and red fluorescent beads having an initial ratio of 100:1, respectively, using a reversible switching mode. The darker bar represents the ratio of red beads over the total number of beads sorted and the lighter bar represents the ratio of blue beads over the total number of beads sorted.

FIG. 10 shows the sorting of red fluorescent beads from blue fluorescent beads using a reversible mode. Beads were prepared in the buffer as described in a ratio of 100:1 (blue: red). After 6 min. the collection channel had a sample of red beads that had been enriched by 96 times. The darker and lighter bars represent the ratio of red or blue heads over the total number of beads sorted, respectively. The throughput was approximately 10 beads/s.

C. Sorting Green Fluorescent Beads from Red Fluorescent in Reversible Mode

Figure 11:
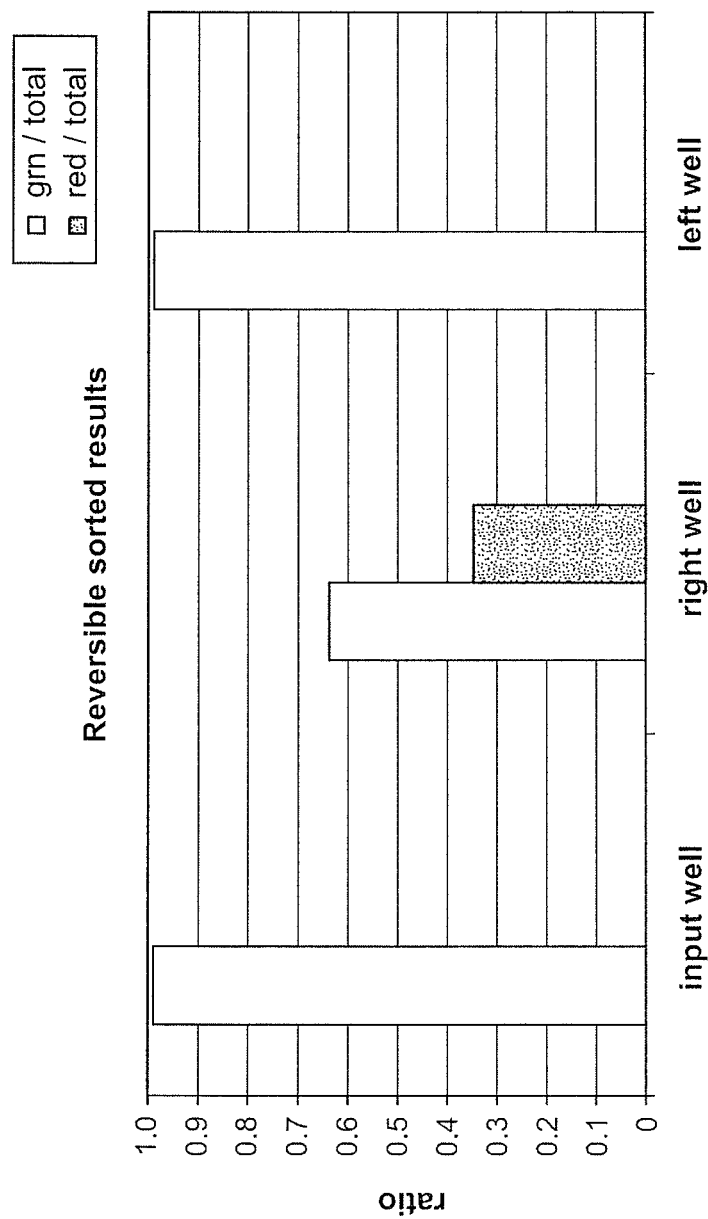
FIG. 11 shows the results of sorting green and red fluorescent beads having an initial ratio of 100:1, respectively, using a reversible switching mode. The darker bar represents the ratio of red beads over the total number of beads sorted and the lighter bar represents the ratio of green beads over the total number of beads sorted.

FIG. 11 shows the results of sorting, by reversible switching, green fluorescent beads to red fluorescent beads in a ratio of 100:1. A mixture of 0.375% beads resuspended in 137 mM NaCl PBS with 10% BSA+0.5% Tw20 was sorted using a 3×4 µm device for about 12 minutes. Reversible switching provides for a rapid and high throughput of undesired beads or cells, with a rapid reversal of fluid flow once a desired bead or cell is detected. This allows for a high throughput and reliable capture of rare cells or events, with rapid analysis of results. The data represented in FIG. 11 show that the red beads were enriched by about 36 times. The darker and lighter bars represent the ratio of red or green beads over the total number of beads sorted, respectively.

D. Sorting E. Coli Cells Expressing Green Fluorescent Protein from Wild Type Cells Sorting results using E. coli cells demonstrated the enrichment capability of microfabricated FACS on living cells. E. coli cells (HB101) expressing green fluorescent protein (GFP) were grown at 30 degrees C. for 12 hours in LB+amp (one colony inoculated into 3 ml medium). The preparation of GPF-expressing E. coli cells is described for example in Sambrook et al. (48). Wild type E. coli HB101 cells were also incubated for 12 hours in LB only medium. After incubation, HB101 and GFP HB101 E. coli cells were resuspended in PBS (I=0.021) three times and stored at 4 degrees C. for sorting.

Immediately before sorting, the cells were resuspended again into PB (4.3 mM $Na_2HPO_4.7H_2O$, 1.4 mM $KH_2PO_4$) containing $10^{-5}$ to $10^{-4}$ M SDS and diluted 10 to 100 fold depending on the absorbance (1 to 1.5) and concentration of the cells. The cells were filtered through a 5 mm syringe filter (Millipore) for elimination of any elongated cells. Fluorescence was excited using a 488 nm Coherent Innova 70 argon ion laser (30 to 50 mW light source, 6 mW out of the objective), the R928 Hammatzu PMT bias was −850V (Chroma) and the emitted fluorescence was filtered using a 535±20 filter.

Different ratios of wildtype E. coli to GFP expressing E. coli cells (described below) were mixed and introduced into the inlet well of the device (volume ranges from 10 to 30 µl of sample); the collection wells were also filled with 10 to 30 µl of PB with $10^{-5}$ to $10^{-4}$ M SDS. After inserting the three platinum electrodes into the wells (with the ground electrode in the inlet well), the voltages were set for forward or reversible sorting modes. The default voltages here were set to −80V and −56V for the waste and collection channels respectively. After sorting for a about two hours, cells were collected using a pipette and streaked onto antibiotic-containing plates (LB plates) and incubated overnight at 37 degrees C. for colony-counting.

Figure 12:
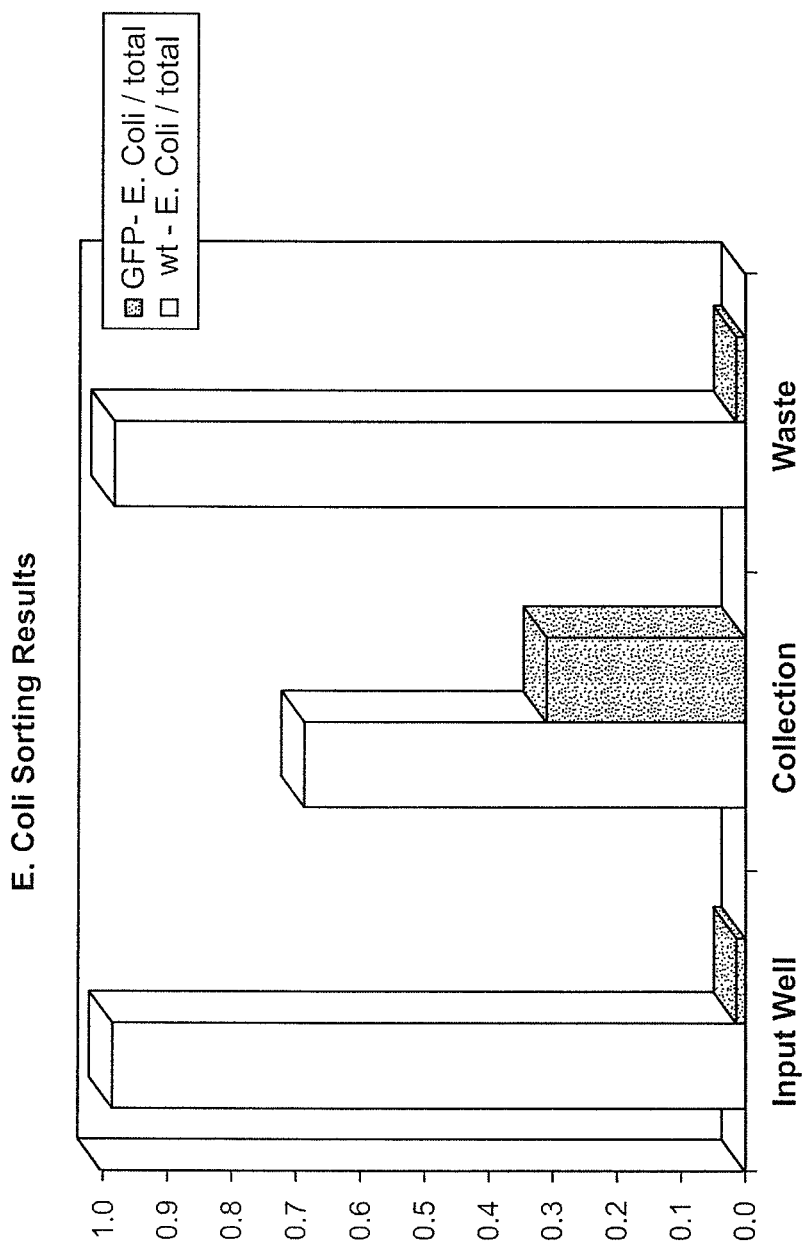
FIG. 12 shows the results of sorting wild-type (non-fluorescent) *E. coli* HB101 cells and *E. coli* HB101 cells expressing green fluorescent protein (GFP) having an initial ratio of 100:1, respectively, using a forward switching mode. The lighter bar represents the ratio of wildtype *E. coli* cells over the total number (approximately 120,000) of cells sorted and the darker bar represents the ratio of GFP-expressing *E. coli* cells over the total number of cells sorted.
Figure 13:
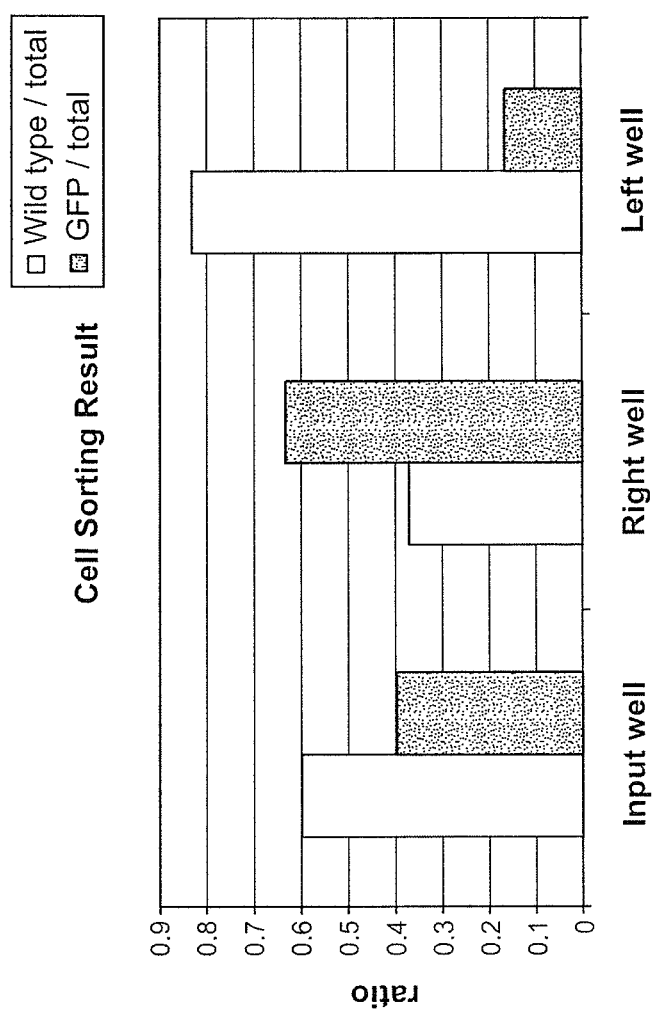
FIG. 13 shows the results of sorting wild-type (non-fluorescent) *E. coli* HB101 cells and *E. coli* HB101 cells expressing green fluorescent protein (GFP) having an initial ratio of 3:2, respectively, using a forward switching mode.

In a first experiment, the initial ratio of wild type to GFP-expressing E. coli cells was 100:1 (results in FIG. 12). After 2 hours of sorting the GFP E. coli cells recovered from the collection well were enriched 30 times, with yields of 20%. In FIG. 12, the dark and light bars represent the ratios of non-fluorescent wild type E. coli and GFP-expressing E. coli to the total number of cells sorted (approximately 120,000 cells), respectively. The sorted cells show relatively constant viability in electric fields up to about 100 V/cm, corresponding to velocities of about 1 to 3 mm/s. The throughput was about 20 cells/s, which can be improved, e.g., by adding a parallel device fabrication or pressure driven switching scheme. FIG. 13 shows the results from cell sorting wild type and GFP-expressing E. coli cells in an initial ratio of 3:2. The GFP-expressing E. coli were enriched by about 1.75 times.

EXAMPLE 8

Exemplary Embodiment and Additional Parameters

Microfluidic Chip Fabrication

In a preferred embodiment, the invention provides a "T" or "Y" shaped series of channels molded into optically transparent silicone rubber or PolyDiMethylSiloxane (PDMS), preferably PDMS. This is cast from a mold made by etching the negative image of these channels into the same type of crystalline silicon wafer used in semiconductor fabrication. As described above, the same techniques for patterning semiconductor features are used to form the pattern of the channels. The uncured liquid silicone rubber is poured onto these molds placed in the bottom of a Petri dish. To speed the curing, these poured molds are baked. After the PDMS has cured, it is removed from on top of the mold and trimmed. In a chip with one set of channels forming a "T", three holes are cut into the silicone rubber at the ends of the "T", for example using a hole cutter similar to that used for cutting holes in cork, and sometimes called cork borers. These holes form the sample, waste and collection wells in the completed device. In this example, the hole at the bottom end of the T is used to load the sample. The hole at one arm of the T is used for collecting the sorted sample while the opposite arm is treated as waste. Before use, the PDMS device is placed in a hot bath of HCl to make the surface hydrophilic. The device is then placed onto a No. 1 (150 μm thick) (25×25 mm) square microscope cover slip. The cover slip forms the floor (or the roof) for all three channels and wells. The chip has a detection region as described above.

Note that any of or all of these manufacturing and preparation steps can be done by hand, or they can be automated, as can the operation and use of the device.

The above assembly is placed on an inverted Zeiss microscope. A carrier holds the cover slip so that it can be manipulated by the microscope's x-y positioning mechanism. This carrier also has mounting surfaces which support three electrodes, which implement the electro-osmotic and/or electrophoretic manipulation of the cells or particles to be analyzed and sorted. The electrodes are lengths of platinum wire taped onto a small piece of glass cut from a microscope slide. The wire is bent into a hook shape, which allows it to reach into one of the wells from above. The cut glass acts as a support platform for each of the electrodes. They are attached to the custom carrier with double-sided tape. This allows flexible positioning of the electrodes. Platinum wire is preferred for its low rate of consumption (long life) in electrophoretic and electro-osmotic applications, although other metals such as gold wire may also be used.

Device Loading

To operate the device for sorting, one of the wells, e.g. the collection or waste well, is first filled with buffer. All three channels, starting with the channel connected to the filled well, wick in buffer via capillary action and gravity. Preferably, no other well is loaded until all the channels fill with buffer, to avoid the formation of air pockets. After the channels fill the remaining wells can be loaded with buffer, as needed, to fill or equilibrate the device. The input or sample well is typically loaded last so that the flow of liquid in the channels is initially directed towards it. Generally, equal volumes of buffer or sample are loaded into each well. This is done in order to prevent a net flow of liquid in any direction once all of the wells are loaded, including loading the sample well with sample. In this embodiment, it is preferred that the flow of material through the device (i.e. the flow of sample) be driven only by the electrodes, e.g. using electro-osmotic and/or electrophoretic forces. The electrodes may be in place during loading, or they can be placed into the wells after loading, to contact the buffer.

Electrodes

Two of the above electrodes are driven by high voltage operational amplifiers (op-amps) capable of supplying voltages of +−150 V. The third electrode is connected to the electrical ground (or zero volts) of the high voltage op-amp electronics. For sorting operation the driven electrodes are placed in the collection and waste wells. The ground electrode is placed in the sample well. The op-amps amplify, by a factor of 30, a control voltage generated by two digital to analog converters (DACs). The maximum voltage these DACs generate is +−5 V, which determines the amplification factor of 30. The 150 V limit is determined by the power supply to the amplifiers, which are rated for +−175 V. These DACs reside on a card (a Lab PC 1200 Card, available from National Instruments, Austin, Tex.) mounted in a personal computer. The card also contains multiple channels of analog to digital converters (ADC's) one of which is used for measuring the signal generated by photo multiplier tubes (PMTs). This card contains two DACs. A third DAC can be used to drive the third electrode with an additional high voltage op amp. This would provide a larger voltage gradient, if desired, and some additional operational flexibility.

Without being bound by any theory, it is believed that the electrodes drive the flow of sample through the device using electro-osmotic or electrophoretic forces, or both. To start the movement of cells or particles to be sorted, a voltage gradient is established in the channels. This is done by generating a voltage difference between electrodes.

In this example, the voltage of the two driven electrodes is raised or lowered with respect to the grounded electrode. The voltage polarity depends on the charge of the cells or particles to be sorted (if they are charged), on the ions in the buffer, and on the desired direction of flow. Because the electrode at the sample well in the examples is always at zero volts with respect to the other two electrodes, the voltage at the "T" intersection or branch point will be at a voltage above or below zero volts, whenever the voltage of the other two electrodes is raised or lowered. Typically, the voltage is set or optimized, usually empirically, to produce a flow from the sample well, toward a downstream junction or branch point where two or more channels meet. In this example, where two channels are used, one channel is typically a waste channel and terminates in a waste well; the other channel is a collection channel and terminates in a collection well.

To direct the particles or cells to a particular channel or arm of the "T" (e.g. collection or waste), the voltage at the electrode in one well (or multiple wells, in multi-channel embodiments) is made the same as the voltage at the junction or branch point, where the channels meet. The voltage of the electrode at one well of the two or more wells is raised or lowered, to produce a gradient between that well and the branch point. This causes the flow to move down the channel towards and into the well, in the direction produced by the gradient. Typically, the voltage of the electrode at the waste well is raised or lowered with respect to the voltage at the collecting well, to direct the flow into the waste channel and the waste well, until a particle or cell is identified for collection. The flow is diverted into the collection channel and collection well by adjusting the voltages at the electrodes to eliminate or reduce the gradient toward the waste well, and provide or increase the gradient toward the collection well. For example, in response to a signal indicating that a cell has been detected for sorting, by examination in a detection region upstream of the branch point, the voltage at the waste and collection points can be switched, to divert the flow from one channel and well to the other.

The voltage at the branch point (the intersection voltage) is determined by the voltage gradient desired (e.g. Volts/mm) times the distance from the sample well electrode to the branch point (gradient×distance), which in this example is placed where all of the channels of the "T" intersect. The gradient also determines the voltage at the waste or collection electrode (gradient×distance from sample well to collection well).

Conceptually, the channels and wells of the "T" can be treated as a network of three resistors. Each segment of the "T" behaves as a resistor whose resistance is determined by the conductivity of the buffer and the dimensions of the channel. A voltage difference is provided across two of the resistors, but not the third. If the electrodes in each of the three wells is equidistant from the branch point, then each channel will have the same resistance.

For example, assume that each section of the "T" has 100 K ohms of resistance. If 100 volts is applied across two of the resistors and the third resistor is left unconnected, the current at the junction of the two resistors would be 50 volts. If a voltage source of 50 volts is connected to the end of the third resistor, the voltage at the junction does not change. That is, a net of zero volts is established across the third resistor; there is no voltage gradient and a flow is not initiated or changed. If a different voltage is applied, a gradient can be established to initiate or direct the flow into one channel or another. For example, to change the direction of flow from one arm of the "T" to the other, the voltage values of the two driven electrodes are swapped. The junction voltage remains the same. If the electrode distances from the "T" intersection are not equal, then the voltages can be adjusted to accommodate the resulting differences in the effective channel resistance. The end result is still the same. The electrode in the well of the channel which is temporarily designated not to receive particles or cells is set at the voltage of the "T" intersection. The voltage at the other driven electrode is set to provide a gradient that directs cell or particle flow into that well. Thus, cells or particles can be sent down one channel or another, and ultimately into one well or another, by effectively opening one channel with a net or relative voltage gradient while keeping the other channel or channels closed by a net or relative voltage gradient of zero.

In a preferred embodiment for sorting according to the invention, a slight flow down the channel that is turned "off" is desired. This keeps the particles or cells moving away from the branch point (the "T" junction), particularly those which have already been directed to that channel. Thus, a small non-zero gradient is preferably established in the "off" or unselected channel. The selected channel is provided with a significantly higher gradient, to quickly and effectively divert the desired cells or particles into that channel.

The placement of the wells and their electrodes with respect to the branch point, and in particular their distance from the branch point, is an important factor in driving the flow of particles or cells as desired. As the wells and electrodes are brought closer to the branch point, it becomes more important to precisely place the electrodes, or precisely adjust the voltages.

Detection Optics

In this example, a Ziess Axiovert 35 inverted microscope is used for detection of cells or particles for sorting. The objective lens of this microscope faces up, and is directed at the detection region of the described microfluidic chip, through the coverslip which in this example is the floor of the device. This microscope contains all the components for epifluorescence microscopy. See, Inoue pp 67-70, 91-97 (37). In this embodiment a mercury arc lamp or argon ion laser is used as the light source. The mercury lamp provides a broad spectrum of light that can excite many different fluorophores. The argon ion laser has greater intensity, which improves the detection sensitivity but is generally restricted to fluorophores that excite at 488 or 514 nm. The mercury lamp is used, for example, to sort beads as described elsewhere herein. The laser is used for sorting GFP $E.\ coli$ bacterial cells as described elsewhere herein. The high power argon ion beam is expanded to fill the illumination port of the microscope, which matches the optical characteristics of the mercury arc lamp and provides a fairly uniform illumination of the entire image area in a manner similar to the mercury lamp. However, it is somewhat wasteful of the laser light. If a lower powered laser is used, the laser light is focused down to coincide with the detection region of the chip, to achieve the same or similar illumination intensity and uniformity with less power consumption.

The objective used in the example is an Olympus PlanApo 60×1.4 N.A. oil immersion lens. The optics are of the infinity corrected type. An oil immersion lens enables collecting a substantial percentage of the 180 degree hemisphere of emitted light from the sample. This enables some of the highest sensitivity possible in fluorescence detection. This microscope has 4 optical ports including the ocular view port. Each port, except the ocular, taps ~20% of the available light collected from the sample when switched into the optical path. Only the ocular port can view 100% of the light collected by the objective. In this embodiment, a color video camera is mounted on one port, another has a Zeiss adjustable slit whose total light output is measured with a photo multiplier tube (PMT). The fourth port is not used.

The microscope focuses the image of the sample onto the plane of the adjustable slit. An achromatic lens collimates the light from the slit image onto the active area of the PMT. Immediately in front of the PMT window an optical band pass filter is placed specific to the fluorescence to be detected. The PMT is a side on-type and does not have a highly uniform sensitivity across its active area. By relaying the image to the PMT with the achromatic lens, this non-uniformity is averaged and its effect on the measured signal is greatly minimized. This also enables near ideal performance of the bandpass filter. A 20% beam splitter has been placed in the light path between the achromat and filter. An ocular with a reticle re-images this portion of the collimated light. This enables viewing the adjustable slit directly, to insure that the detection area that the PMT measures is in focus and aligned. The adjustable slit allows windowing a specific area of the channel for detection. Its width, height, and x,y position are adjustable, and conceptually define a detection region on the chip. In this embodiment, the microscope is typically set to view a 5 µm (micron) length of the channel directly below the "T" intersection.

The PMT is a current output device. The current is proportional to the amount of light incident on the photocathode. A transimpedance amplifier converts this photo-current to a voltage that is digitized by the Lab PC 1200 card. This allows for interpreting the image to select cells or particles having an optical reporter for sorting, as they pass through the detection region, based for example on the amount of light or fluorescence measured as an indication of whether a cell or particle has a predetermined level of reporter and should be chosen for collection. Voltages at the electrodes of the chip can be adjusted or switched according to this determination, for example by signals initiated by or under the control of a personal computer acting in concert with the Lab PC 1200 card.

Absorbence Detection

In another embodiment for detecting cells or particles, absorbence detection is employed, which typically uses relatively longer wavelengths of light, e.g., ultraviolet (UV). Thus, for example, a UV light source can be employed. Additional objective lenses can be used to image a detection region, such that the lenses are preferably positioned from the top surface if the PDMS device is made reasonably thin. Measurement of the light transmitted, i.e., not absorbed by the particle or cell, using an adjustable slit, e.g., a Zeiss adjustable slit as described above, is similar to that used in fluorescence detection. A spectrophotometer may also be used. As particles or cells pass through the detection window they attenuate the light, permitting detection of particles or cells having a desired characteristic and particles or cells that lack it. This can improve the accuracy of the particle sorting, for example, when sorting based on an amount of a characteristic, rather than presence of the characteristic alone, or to confirm a signal.

It is noted that in some cases, detection by absorbence may be detrimental at certain wavelengths of light to some biological material, e.g., *E. coli* cells at shorter (UV) wavelengths. Therefore, biological material to be sorted in this manner should first be tested first under various wavelengths of light using routine methods in the art. Preferably, a longer wavelength can be selected which does not damage the biological material of interest, but is sufficiently absorbed for detection.

Radiation Pressure/Optical trapping

In another embodiment, an optical trap, or laser tweezers, may be used to sort or direct cells in a PDMS device of the invention. One exemplary method to accomplish this is to prepare an optical trap, methods for which are well known in the art, that is focused at the "T" intersection proximate to, and preferably downstream of, the detection region. Different pressure gradients are established in each branch. A larger gradient at one branch channel creates a dominant flow of particles or cells, which should be directed into the waste channel. A second, smaller gradient at another branch channel should be established to create a slower flow of fluid from the "T" intersection to another channel for collection. The optical trap remains in an "off" mode until a desired particle is detected at the detection region. After detection of a desired characteristic, the particle or cell is "trapped", and thereby directed or moved into the predetermined branch channel for collection. The particle or cell is released after it is committed to the collection channel by turning off the trap laser. The movement of the cell or particle is further controlled by the flow into the collection well. The optical trap retains its focus on the "T" intersection until the detection region detects the next cell or particle.

In the case of a water-in-oil micelle (or reverse micelle) the index of refraction of the water droplet is generally lower than the index of refraction of the surrounding oil phase. In that circumstance, optical tweezers do not form a stable trap for the water droplet, and in fact will tend to repel the droplet. This effect can be used to sort droplets, in that a focused optical beam can be used to deflect droplets, e.g. from a main channel into a waste or collection channel. Stated another way, a differential in the index of refraction between two phases of a droplet system, e.g. where droplets of one phase are separated or encapsulated by another phase, may be exploited to move or direct droplets in response to radiation pressure. This technique can also be applied to any objects, including without limitation cells, molecules, etc. that have a different refractive index than the surrounding medium. In particular, radiation pressure (e.g. an optical beam) can be used to advantageously sort objects (e.g. droplets) whose index of refraction is lower than that of the surrounding medium.

Flow control by optical trapping permits similar flexibility in buffer selection as a pressure driven system. In addition, the pressure gradients can be easily established by adjusting the volume of liquid added to the wells. However, it is noted that the flow rate will not be as fast when the pressure in one channel is above ambient pressure and pressure in another is below.

Forward Sorting

In an electrode-driven embodiment, prior to loading the wells with sample and buffer and placing the electrodes, the electrode voltages are set to zero. Once the sample is loaded and the electrodes placed, voltages for the driven electrodes are set, for example using computer control with software that prompts for the desired voltages, for example the voltage differential between the sample and waste electrodes. If the three wells are equidistant from the "T" intersection, one voltage will be slightly more than half the other. In a typical run, the voltages are set by the program to start with directing the particles or cells to the waste channel. The user is prompted for the threshold voltage of the PMT signal, to identify a cell for sorting, i.e. diversion to the collection channel and well. A delay time is also set. If the PMT voltage exceeds the set threshold, the driven electrode voltages are swapped and then, after the specified delay time, the voltages are swapped back. The delay allows the selected particle or cell enough time to travel down the collection channel so that it will not be redirected or lost when the voltages are switched back. As described above, a slight gradient is maintained in the waste channel, when the voltages are switched, to provide continuity in the flow. This is not strong enough to keep the particle or cell moving into the other or "off" channel it if is too close to or is still at the branch point.

The value of this delay depends primarily on the velocity of the particles or cells, which is usually linearly dependent on the voltage gradients. It is believed that momentum effects do not influence the delay time or the sorting process. The particles or cells change direction almost instantaneously with changes in the direction of the voltage gradients. Unexpectedly, experiments have so far failed to vary the voltages faster than the particles or cells can respond. Similarly, experiments have so far shown that the dimensions of the channels do not effect the delay, on the distance and time scales described, and using the described electronics. In addition the speed with which the cells change direction even at high voltage gradients is significantly less than needed to move them down the appropriate channel, when using a forward sorting algorithm.

Once the voltage and delay value are entered the program, it enters a sorting loop, in which the ADC of the Lab PC 1200 card is polled until the threshold value is exceeded. During that time, the flow of particles or cells is directed into one of the channels, typically a waste channel. Once the threshold is detected, the above voltage switching sequence is initiated. This directs a selected cell or particle (usually and most preferably one at a time) into the other channel, typically a collection channel. It will be appreciated that the cells or particles are being sorted and separated according to the threshold criteria, without regard for which channel or well is considered "waste" or "collection". Thus, cells can be removed from a sample for further use, or they can be discarded as impurities in the sample.

After the switching cycle is complete (i.e. after the delay), the program returns to the ADC polling loop. A counter has also been implemented in the switching sequence which keeps track of the number of times the switching sequence is executed during one run of the program. This should represent the number of cells or particles detected and sorted. However, there is a statistical chance that two cells or particles can pass through simultaneously and be counted as one. In this embodiment, the program continues in this polling loop indefinitely until the user exits the loop, e.g. by typing a key on the computer keyboard. This sets the DACs (and the electrodes) to zero volts, and the sorting process stops.

Reverse Sorting

The reverse sorting program is similar to the forward sorting program, and provides additional flexibility and an error correction resource. In the event of a significant delay in changing the direction of flow in response to a signal to divert a selected cell or particle, for example due to momentum effects, reversible sorting can change the overall direction of flow to recover and redirect a cell or particle that is initially diverted into the wrong channel. Experiments using the described electrode array show a delay problem and an error rate that are low enough (i.e. virtually non-existent), so that reversible sorting does not appear necessary. The algorithm and method may be beneficial, however, for other embodiments such as those using pressure driven flow, which though benefiting from an avoidance of high voltages, may be more susceptible to momentum effects.

If a cell is detected for separation from the flow, and switching is not fast enough, the cell will end up going down the waste channel with all of the other undistinguished cells. However, if the flow is stopped as soon as possible after detection, the cell will not go too far. A lower driving force can then be used to slowly drive the particle in the reverse direction back into the detection window. Once detected for a second time, the flow can be changed again, this time directing the cell to the collection channel. Having captured the desired cell, the higher speed flow can be resumed until the next cell is detected for sorting. This is achieved by altering the voltages at the electrodes, or altering the analogous pressure gradient, according to the principles described above.

To move cells at higher velocities, for faster and more efficient sorting, higher voltages may be needed, which could be damaging to cells, and can be fatal to living cells. Preliminary experiments indicate that there may be a limit to the trade-off of voltage and speed in an electrode driven system. Consequently, a pressure driven flow may be advantageous for certain embodiments and applications of the invention. Reversible sorting may be advantageous or preferred in a pressure driven system, as hydraulic flow switching may not be done as rapidly as voltage switching. However, if a main or waste flow can move fast enough, there may be a net gain in speed or efficiency over voltage switching even though the flow is temporarily reversed and slowed to provide accurate sorting. Pressure driven applications may also offer wider flexibility in the use of buffers or carriers for sample flow, for example because a response to electrodes is not needed.

EXAMPLE 9

Microfabrication of Pump and Valve Structures

The invention provides systems for fabricating and operating microfabricated structures such as on/off valves, switching valves and pumps made out of various layers of elastomer bonded together. These structures are suitable for controlling and fluid movement in the described devices, e.g. flow control in the fluid channels.

As described, the invention uses multilayer soft lithography to build integrated (i.e.: monolithic) microfabricated elastomeric structures. Layers of soft elastomeric materials are bound together, resulting in biocompatible devices that are reduced by more than two orders of magnitude in size, compared to conventional silicon-based devices. The preferred elastomeric material is a two-component addition cure material in which one layer (e.g. a bottom layer) has an excess of one component, while another adjacent layer has an excess of another component. In an exemplary embodiment, the elastomer used is silicone rubber. Two layers of elastomer are cured separately. Each layer is separately cured before the top layer is positioned on the bottom layer. The two layers are then re-cured to bond the layers together. Each layer preferably has an excess of one of the two components, such that reactive molecules remain at the interface between the layers. The top layer is assembled on top of the bottom layer and heated. The two layers bond irreversibly such that the strength of the interface approximates or equals the strength of the bulk elastomer. This creates a monolithic three-dimensional patterned structure composed entirely of two layers of bonded together elastomer. When the layers are composed of the same material, interlayer adhesion failures and thermal stress problems are avoided. Additional layers may be added by repeating the process, wherein new layers, each having a layer of opposite "polarity" are cured and bonded together.

Thus, in a preferred aspect, the various layers of elastomer are bound together in a heterogenous (A to B) bonding. Alternatively, a homogenous (A to A) bonding may be used in which all layers would be of the same chemistry. Thirdly, the respective elastomer layers may optionally be glued together by an adhesive instead.

Elastomeric layers may be created by spin coating an RTV mixture on a mold at 2000 rpms for 30 seconds yielding a thickness of approximately 40 microns. Layers may be separately baked or cured at about 80° C. for 1.5 hours. One elastomeric layer may be bonded onto another by baking at about 80° C. for about 1.5 hours. Micromachined molds may be patterned with a photoresist on silicon wafers. In an exemplary aspect, a Shipley SJR 5740 photoresist was spun at 2000 rpms patterned with a high resolution transparency film as a mask and then developed yielding an inverse channel of approximately 10 microns in height. When baked at 2000° C. for about 30 minutes, the photoresist reflows and the inverse channels become rounded. In preferred aspects, the molds may be treated with trimethylchlorosilane (TMCS) vapor for about a minute before each use in order to prevent adhesion of silicone rubber.

In another preferred aspect, a first photoresist layer is deposited on top of a first elastomeric layer. The first photoresist layer is then patterned to leave a line or pattern of lines of photoresist on the top surface of the first elastomeric layer. Another layer of elastomer is then added and cured, encapsulating the line or pattern of lines of photoresist. A second photoresist layer is added and patterned, and another layer of elastomer added and cured, leaving line and patterns of lines of photoresist encapsulated in a monolithic elastomer structure. Thereafter, the photoresist is removed leaving flow channel(s) and control line(s) in the spaces which had been occupied by the photoresist. Tetrabutylammonium is one photoresist etchant that is compatible with a preferred RTV 615 elastomer. An advantage of patterning moderate sized features (10 microns) using a photoresist method is that a high resolution transparency film can be used as a contact mask.

This allows a single researcher to design, print, pattern the mold, and create a new set of cast elastomer devices, typically all within 24 hours.

A preferred elastomeric material is GE RTV 615 elastomer or a silicone rubber that is transparent to visible light, making multilayer optical trains possible. This allows optical interrogation of various channels or chambers in the microfluidic device. In addition, GE RTV 615 elastomer is biocompatible. Being soft, closed valves form a good seal even if there are small particulates in the flow channel. Silicone rubber is also biocompatible and inexpensive, especially when compared with a crystal silicon.

The systems of the invention may be fabricated from a wide variety of elastomers, such as the described silicon rubber and RTV 615. However, other suitable elastomeric materials may also be used. GE RTV 615 (formulation) is a vinyl silane crosslinked (type) silicone elastomer (family). The invention is not limited to this formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves (A to A), or they may be of two different types, and are capable of bonding to each other (A to B). (Another possibility is to use an adhesive between layers.)

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability. There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones. See e.g., Ser. No. 60/186,856 filed Mar. 3, 2000.

In addition to the use of "simple" or "pure" polymers, crosslinking agents may be added. Some agents (like the monomers bearing pendant double bonds for vulcanization) are suitable for allowing homogeneous (A to A) multilayer soft lithography or photoresist encapsulation; complementary agents (i.e. one monomer bearing a pendant double bond, and another bearing a pendant Si—H group) are suitable for heterogeneous (A to B) multilayer soft lithography.

Materials such as chlorosilanes such as methyl-, ethyl-, and phenylsilanes, for example polydimethylsilooxane (PDMS) such as Dow Chemical Copr. Sylgard 1, 82, 184 or 186, or alipathic urethane diacrylates such as (but not limited to) Ebecryl 270 or In 245 from UBC Chemical may also be used. Elastomers may also be "doped" with uncrosslinkable polymer chains of the same class. For instance RTV 615 may be diluted with GE SF96-50 Silicone Fluid. This serves to reduce the viscosity of the uncured elastomer and reduces the Young's modulus of the cured elastomer. Essentially, the crosslink-capable polymer chains are spread further apart by the addition of "Inert" polymer chains, so this is called "dilution". RTV 615 cures at up to 90% dilution, with a dramatic reduction in Young's modulus.

The described monolithic elastomeric structures valves and pumps can be actuated at very high speeds. For example, the present inventors have achieved a response time for a valve with aqueous solution therein on the order of one millisecond, such that the valve opens and closes at speeds approaching 100 Hz. The small size of these pumps and valves makes them fast and their softness contributes to making them durable. Moreover, as they close linearly with differential applied pressure, this allows fluid metering and valve closing in spite of high back pressures.

In various aspects of the invention, a plurality of first flow channels pass through the elastomeric structure with a second flow channel, also referred to as an air channel or control line, extending across and above a first flow channel. In this aspect of the invention, a thin membrane of elastomer separates the first and second flow channels. Movement of this membrane (due to the second flow channel being pressurized) will cut off flow passing through the lower flow channel. Typically, this movement is downward from a the interface with top control layer into an closing an underlying first flow channel.

A plurality of individually addressable valves can be formed and connected together in an elastomeric structure, and are then activated in sequence such that peristaltic pumping is achieved. In other optional preferred aspects, magnetic or conductive materials can be added to make layers of the elastomer magnetic or electrically conducting, thus enabling the creation of elastomeric electromagnetic devices.

In preferred aspects, channels of the invention have width-to-depth ratios of about 10:1. In an exemplary aspect, fluid and/or air channels have widths of about 1 to 1000 microns, and more preferably 10-200 microns and most preferably 50-100 microns. Preferred depths are about 1 to 100 microns, and more preferably 2-10 microns, and most preferably 5 to 10 microns.

In preferred aspects, an elastomeric layer has a thickness of about 2 to 2000 microns, and more preferably 5 to 50 microns, and most preferably 40 microns. Elastomeric layers may be cast thick for mechanical stability. In an exemplary embodiment, one or more layers is 50 microns to several centimeters thick, and more preferably approximately 4 mm thick. Membrane separating fluid and air channels has a typical thickness of about 30 nm. In one embodiment the thickness of one elastomeric layer (e.g. at top or control layer) is about 10 times the thickness of an adjacent layer (e.g. a fluid or bottom layer.

A typical RTV valve of the invention is 100 µm×10 µm×10 µm, connected to an off-chip pneumatic valve by a 10-cm-long air tube. In one example, the pressure applied on the control line is 100 kPa, which is substantially higher than the approximately 40 kPa required to close the valve. Thus, when closing, the valve in this example is pushed closed with a pressure 60 kPa greater than required. When opening, however, the valve is driven back to its rest position only by its own spring force, which is less than or equal to about 40 kPa). A signal to open or close the valve is effected by changing the pressure accordingly. In this example there is a lag between the control signal and the control pressure response, due to the limitations of the miniature valve used to control the pressure. To accommodate this lag, these exemplary valves run comfortably at 75 Hz when filled with aqueous solution. If one used another actuation method which did not have an opening and closing lag, this valve would run at about 375 Hz. Note also that the spring constant can be adjusted by changing the membrane thickness; this allows optimization for either fast opening or fast closing.

The flow channels of the present invention may optionally be designed with different cross sectional sizes and shapes, offering different advantages, depending upon their desired application. For example, the cross sectional shape of a lower fluid channel may have a curved upper surface, either along its entire length or in the region disposed under an upper air channel or cross channel. In certain embodiments a curved upper surface facilitates valve sealing. In an alternate aspect, the bottom of a fluid channel is rounded such that its curved surface mates with the curved upper wall upon valve closure.

EXAMPLE 10

Microfabrication of a Multi-Phase Device

A multiphase device of the invention may be microfabricated using techniques such as those described in Examples 1, 8 and 9, above, for manufacturing other components of microfluidic devices. For example, channels and/or valves forming a droplet extrusion region can be prepared in layers of elastomeric material, such as urethane, by multilayer soft lithography. The example presented in this section describes the manufacture of an exemplary device according to such methods.

Polymer Preparation 10-15 g Urethane diacrylate (Ebecryl 270, UCB Chemicals) was weighed out and heated to about 80 or 85° C. to lower its viscosity. Irgacure 500 (Ciba) was then mixed into the heater material as a catalyst, in an amount such that the weight-to-weight ratio of the catalyst to monomer was about 0.5%. The resulting mixture was then returned to the 85° C. oven for about 15 minutes to remove any trapped bubbles that may have been introduced into the material during the mixing process.

Microfluidic Channel Mold:

The molds for the urethane layers comprised p-type silicon wafers with raised patterns of photoresist consisting of microfluidic channels. The patterns were prepared by spin-coating photoresist (e.g., SJR5740, Shipley) onto silicon wafers at 3000 rpm so that a layer about 10 microns thick was formed on the wafer. The silicon wafer was pretreated with hexamethyldisilizane (HMDS), an adhesion promoter, in vapor phase, to promote adhesion of the photoresist to the wafer.

The photoresist-coated wafer was then baked at 85° C. for about one hour to harden the photoresist layer, and then patterned in a mask aligner. The pattern consisted of sheet film from a linotronic printer (3386 dpi resolution) which had the desired microfluidic pattern on it. Microfilm may also be suitable. Patterns can be created using appropriate software, such as Photoshop (Adobe, San Jose, Calif.). The patterns were each mounted on a sheet of glass, emulsion side up, and placed in the mask aligner. UV light was then be used to expose each patterns on the surface of a wafer. Typical exposure time in a mask aligner was approximately 2-4 minutes (e.g., 2.3 minutes). The patterns on the exposed wafers were then developed, e.g., in 20% Microposit 240 (in deionized water) for approximately 90 seconds, to remove all the photoresist except for the patterned microfluidic channels. The positive channels which remained on the surface were then hard-baked (200° C. for 30 minutes) on the wafer surface to round them and give them good chemical resistance to washing agents such as isopropyl alcohol and acetone.

Fabrication of Elastomeric Layers

A. Top Layer

The top layer of the microfabricated device contained the valve structures of the device, as described in Example 9 above. The layer was prepared by first pouring a thick (e.g. 3-10 mm) layer of Ebecryl 270/Irgacure 500 on the surface of a silicon wafer having the photoresist-based valve structure (prepared as described above). The valve structures ranged from about 45 to about 180 μm in diameter. This top layer was then cured by a UV light source (an ELC500, Electrolyte Corporation) for about five minutes and under nitrogen gas. The polymerized urethane was removed from the mold and input holes for air and valves were drilled through the urethane using a No. 73, 74 or 75 drill bit (preferably No. 74). The layer was next trimmed for size and washed with isopropanol to remove any debris from its surface.

B. Middle Layer

The middle layer contained channels for different, incompatible fluids (e.g., oil and water) that flow through the device. The diameter of the main and sample inlet channels was 60 μm (after rounding). However, in one device, the channels at the cross-flow junction (i.e., the droplet extrusion region) were tapered to 30 μm in diameter. Preferably, the taper angle is about 45 degrees, and the distance covered by this taper is about the width of the wide channel minus the width of the narrow channel, divided by two. The taper assists in facilitating smooth flow, by avoiding sharp corners for droplets to negotiate. The narrower channel allows droplets to shear better, e.g. more easily, by making them thinner and longer. These channels were prepared by spin coating Ebecryl 270/Irgacure 500 on the surface of a silicon wafer to a thickness of about 30 μm. This was accomplished by heating the material to about 175° C. in a glass petri dish and pouring it onto the patterned silicon wafer. The wafer was spun for 45 seconds at 8000 rpm to produce the thin layer. The middle layer was next cured under the UV light source as described, above, for the top layer.

C. Bottom Layer

The bottom layer is typically a structural layer used to tightly seal the crossflow channels in the middle layer so that the device can be operated at high pressures (e.g., as high as 40 psi). Specifically, in the exemplary microfabricated device described here, the bottom layer was a thin (e.g., approximately 0.5 cm) layer of Ebecryl 270/Irgacure 500 which was poured into a petri dish and cured by a UV light system for about 5 minutes under nitrogen gas. The cured bottom layer was then rinsed with isopropyl alcohol to remove surface contaminants and promote adhesion to the middle layer.

Layer Bonding

The individual layers, prepared as described above, were assembled to form a multi-layered, multi-phased microfluidic device of the invention. The top was adhered, with the side containing valve channels facing down, to the cured middle layer by applying gentle pressure. A dissecting microscope was used to precisely place the top layer on the channels of the middle layer such that the valve structures are properly positioned near the output ends of the crossflow device. The two adhered layers were then cured for just under 10 minutes (i.e., 9.9 minutes) under UV light. Input wells for the different fluids, such as water and oil, were then be drilled through the device using a No. 73 drill bit, and the surfaces were cleaned with deionized water and dried with nitrogen gas.

The composite top and middle layers were bonded to the bottom layer by sealing the composite top and middle layers (middle side down) to the bottom layer with gentle pressure and curing the three layers in the UV light system for just under 20 minutes (i.e., 19.8 minutes) to optimize bonding.

EXAMPLE 11

Operation of the Multi-Phase Device

The devices of this invention are useful for partitioning a first fluid into droplets within a second, incompatible fluid.

For example, in preferred embodiments the device partitions droplets of an aqueous solution, which typically contains a sample of molecules or particles (e.g., cells or virions) into a pressurized stream or flow of oil in a main channel of the device.

Fluids, such as oil and water may be loaded into separate syringes fitted with high-pressure connection fittings (available, e.g., from Upchurch, Scientific) for loading into a microfabricated device of the invention. Preferably, the syringes are pressurized, e.g., with pressurized air, to between 0 and 30 psi. Microline tubing (e.g., 0.020 inch inner diameter) with luer stub adapters (e.g., 23 gauge) at the ends can be used to direct the fluids from the syringes for input into their respective input wells of a device (for example, the particular device described in Example 10, above). Preferably, the microline tubing is first purged by subjecting the syringes to gentle air pressure (for example, between about 1-2 psi) before attaching the lines to their respective inlet ports, so that dead air space within the tubing is eliminated.

The microlines are slowly pressurized with their respective fluids (e.g., oil and water) after connecting them to the device to prime the device with fluid and purge any trapped air in channels of the device. For example, the lines are typically pressurized to a pressure of approximately 5 psi, preferably while observing the device, for example using a light microscope with a 10× objective lense.

The pressures of the different fluids are then adjusted so that their pressures are balanced at the droplet extrusion region. Thus, for example, in preferred embodiments wherein droplets of aqueous solution are extruded into a pressurized stream of oil, the pressures of the oil and/or fluid lines are adjusted so that the pressure difference of the oil and water channels at the droplet extrusion region is zero, and the oil and water are in a state of equilibrium. This can be visually observed. Droplet extrusion can then be initiated by slightly adjusting the pressure difference between the different fluids (i.e., at the different inlet lines) so that the droplet fluid (e.g., water) enters the main channel and is sheared off at a fixed frequency. A preferred frequency is 1 Hz because the frequency with which droplets are sheared off into the main channel depends on the pressure difference between the different fluids, the frequency can be readily adjusted by simply adjusting the pressures of the individual fluid lines.

In certain embodiments, air may be used in place of water or another fluid. Saturated air, i.e. air saturated with water vapor, is preferred to prevent miscibility with the oil phase. The air source in these embodiments may be oscillated to control droplet frequency.

Figure 16A:
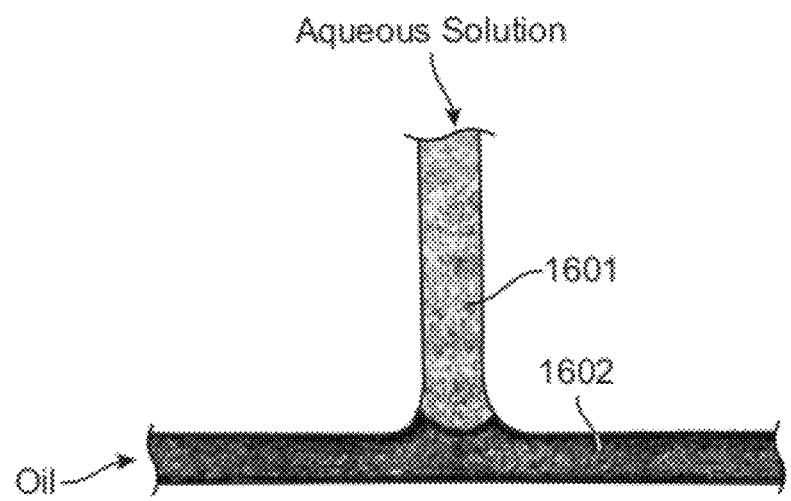
FIGS. 16A and B show exemplary architectures for droplet extrusion regions in a microfabricated device.
Figure 16B:
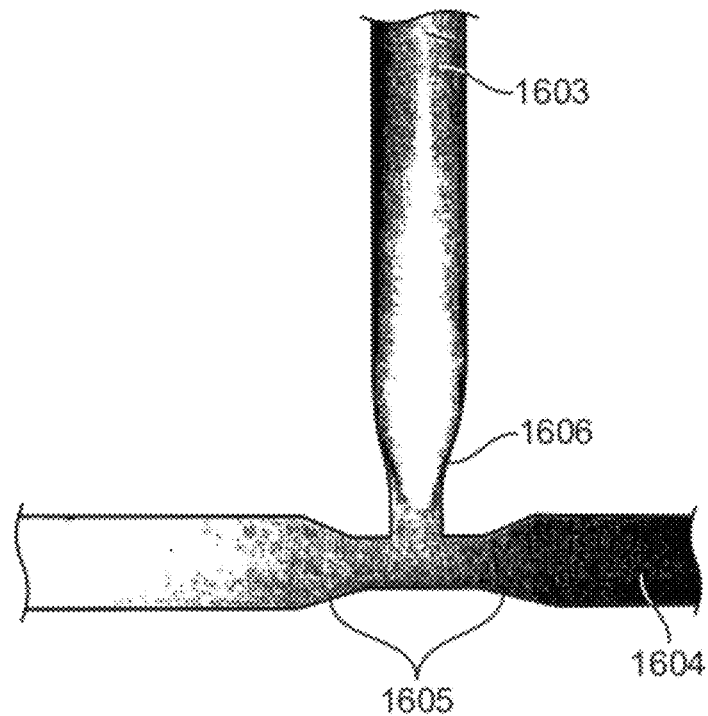

As a specific example, microscopic devices were prepared as described in Example 10, above, and tested. The channel architecture for the droplet extrusion region of the first device is shown in FIG. 16A. In this device, the inlet channel 1601 (inner diameter 30 μm) intersects the main channel 1602 (inner diameter 30 μm) at a T-intersection (i.e., an angle perpendicular to the main channel). Other intersections and angles may be used. The walls of the inlet and main channels were not tapered in this device. The channel architecture for the second exemplary extrusion region is shown in FIG. 16B. In this device, both the inlet channel 1603 and the outlet channel 1604 have inner diameters of 60 μm. However, the channels 1605 and 1606 taper to inner diameters of 30 μm at the droplet extrusion region.

Figure 17A:
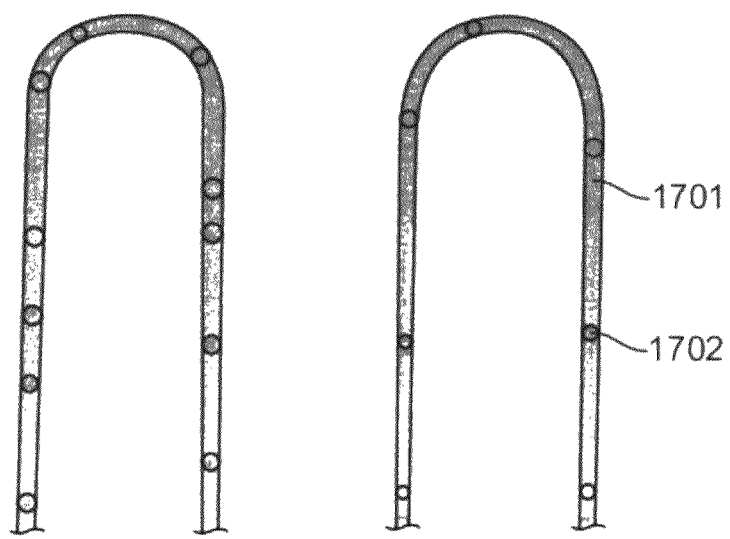
FIGS. 17A-C show channels and junction that can be used to route and/or sort droplets in a microfabricated device.
Figure 17B:
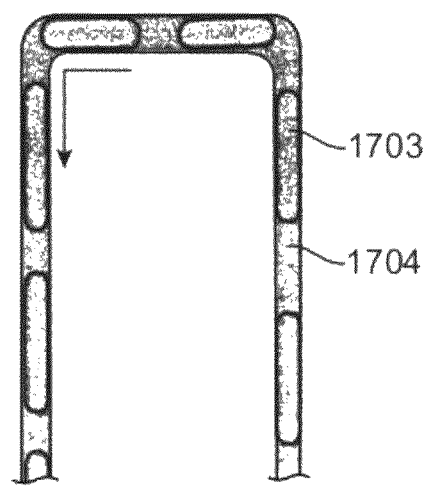
Figure 17C:
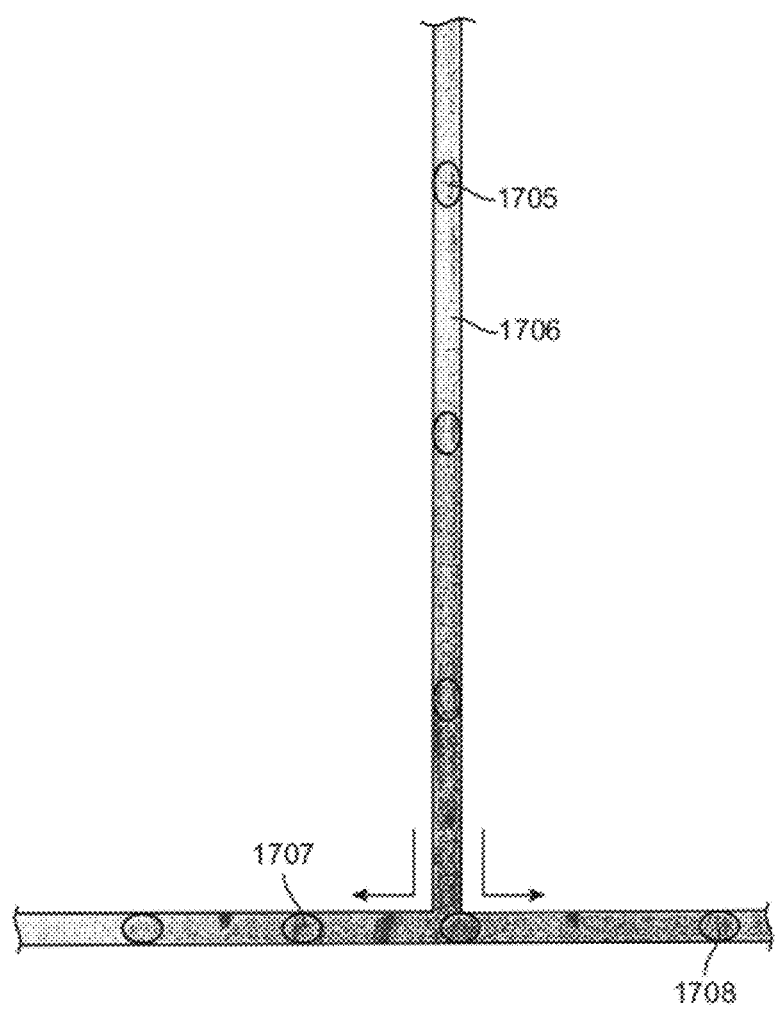

The extruded droplets were routed through different channel architectures which are illustrated in FIGS. 17A-C. Specifically, FIG. 17A shows an exemplary S-shaped channel. Channels with curves may be beneficial in applications where less resistance to flow is desired. Channels with sharp or square are generally easier to fabricate, for example because rounded edges may be pixilated when a pattern is drawn using digital composition and printing (e.g. Photoshop). FIG. 17B shows the channel architecture of an exemplary rectilinear or "U-shaped" channel. Droplets were propelled through each channel by a positive pressure flow control (i.e. using pumps and valves as described herein). Other flow control techniques may also be used. In particular, FIG. 17A illustrates droplets of aqueous solution 1702 transported through an S-shaped channel in a pressurized stream of oil 1701. FIG. 17B illustrates droplets 1703 which were transported through a U-shaped channel in a stream of oil 1704. Typical pressures for the operation of this device are 10-15 psi. Droplets 1705 were also routed through a T-shaped junction, depicted in FIG. 17C, and individual droplets were sorted by directing droplets into a first channel 1707 or a second channel 1708, as desired.

These examples show that the droplets can be directed along any straight, curved, branched, or other path, and can turn corners, without loss of integrity. Droplets of a first fluid (e.g., water or aqueous buffer) can be directed along channels in a pressurized flow of a second, incompatible fluid (e.g., oil) and individual sorted or routed along particular branch channels. Thus, the devices of the invention can be used to sort individual droplets, as well as molecules or particular (e.g., polynucleotides, polypeptides, enzymes, substrates, cells and virions) contained therein, using methods such as those described in Example 6.

EXAMPLE 12

Control of Droplet Size and Frequency

Figure 18A:
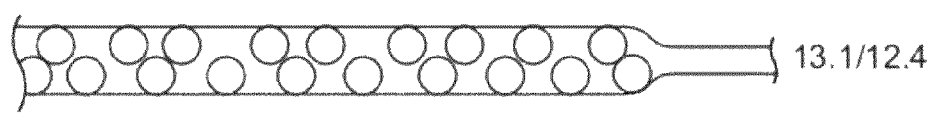
FIGS. 18A-C are photomicrographs showing droplets of aqueous solution in a flow of oil (hexadecane with 2% Span 80 surfactant) in a microfluidic device with rectangular channels. The relative water/oil pressures are provided to the right of each photomicrograph.
Figure 18B:
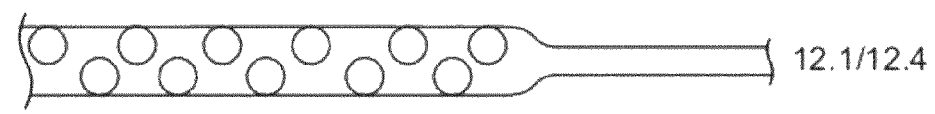
Figure 18C:
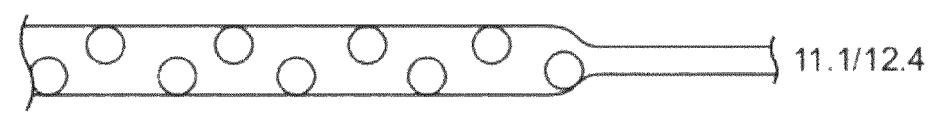

As demonstrated in Example 11, above, the devices of this invention may be used to partition a first fluid into droplets within a second, incompatible or immiscible fluid. For example, the invention provides a preferred embodiment where a microfluidic device partitions droplets of an aqueous solution into a pressurized stream or fluid of oil (for example, decan, tetradecane or hexadecane) in a main channel of the device. The droplets of aqueous solution typically contain a sample of molecules (e.g.; for small scale chemical reactions) or particles (such as cells or virions). As demonstrated here, the size and frequency of droplets formed in a main channel of such devices may be precisely controlled by modifying the relative pressure of the incompatible fluids (e.g., water and oil) in the device. In addition, the shape of the microchannels in these devices may also influence the size distribution and morphology of droplet patterning. Specifically, channels that have not been rounded (e.g., rectangular channels) produce monodisperse droplets with regular periodicity. The droplets associate with the walls of the rectangular channels as they flow downstream from the droplet extrusion region (FIGS. 18A-C). By contrast, the patterns of aqueous droplets formed in round channels are more complex and range from periodic, monodisperse droplets to ordered layers of packed droplets (FIG. 19). Thus, using a microfluidic device of this invention, in conjunction with the methods illustrated in this example, a user may produce a wide variety of droplet shapes and patterns in emulsions, e.g., of water in oil.

As specific, non-limiting examples to illustrate the variety of droplet shapes and patterns that may be produced with a microfluidic device of this invention, polyurethane microfluidic devices were fabricated using methods similar to those described in Example 10, above. Specifically, a positive relief mold was etched onto the surface of a silicon wafer coated with photoresist (SJR5740, Shipley). Acrylated urethane (Ebecryl 270, UCB Chemicals) was then poured onto this positive relief mold and cured using UV light. The microchannels molded into the patterned urethane layer were fully encapsulated by curing a thin urethane layer on a coverslip and bonding the cover slip to the molded urethan layer through additional UV light exposure.

Microfluidic devices having both rounded and non-rounded (e.g., rectangular) channels were manufactured by these methods. Devices having rounded channels were produced by heating the positive-relief mold to a sufficient temperature (80-110° C.) so that the photoresist material flowed, thereby giving the positive relief contours, which are normally rectangular, rounded edges.

The resulting microfluidic devices comprised a droplet extrusion region having the channel architecture illustrated in FIG. 16B. In the particular devices described here, the inlet channel 1603 and the outlet channel 1604 had measured channel dimensions of approximately 60 µm wide by 9 µm high. However, the channels 1605 and 1606 tapered to dimensions of approximately 35 µm by 6.5 µm in the droplet extrusion region.

Fluids were introduced into the urethane microfluidic devices through pneumatically driven syringe reservoirs that contained either an aqueous solution (i.e., water) or an oil. Various oils were tested in the devices, including decane, tetradecane and hexadecane. In each instance, the oil phase introduced into the device also contained a surfactant (Span 80) with concentrations (vol./vol.) of either 0.5, 1.0 or 2.0%. The devices were equilibrated prior to crossflow by priming the outflow channel with oil to eliminate interactions of the aqueous phase with the hydrophilic urethane walls of the channels. Water droplets were then produced in the oil stream by modifying the relative oil and water pressures such that the water entered the droplet extrusion region, shearing off into discrete droplets as described in Example 11, supra.

FIGS. 18A-C provide photomicrographs of water droplets in an oil stream (hexadecane with 2% Span80 surfactant) that formed in non-rounded channels of a microfluidic device prepared as described above. These micrographs illustrate the effect of moving progressively from high water pressure, relative to the oil pressure, to relatively low water pressure and demonstrate the effects the relative water/oil pressure has on the size and spacing between aqueous droplets. Specifically, at low water pressure (FIG. 18C) smaller, monodisperse droplets of aqueous solution are formed in the oil flow. As water pressure is increased relative to the oil pressure (FIG. 18B) the droplets become larger and are spaced closer together. At still higher water pressures (FIG. 18C) the droplets begin to collide in the main channel.

The droplet patterns formed in rounded channels are more complex. FIG. 19 provides photomicrographs of water droplets that formed in an oil stream (hexadecane with 2% Span80 surfactant) that formed in a microfluidic device having rounded channel contours. The relative water/oil pressures are indicated to the right of each micrograph. The droplet patterns range from periodic, single droplets (FIG. 19, Frames J and L) to ordered layers of packed aqueous droplets (e.g., FIG. 19, Frame A).

When the relative oil pressure in the microchannel exceeds the water pressure (i.e., $P_w < P_o$), single monodisperse separated droplets are formed at a frequency of about 20-80 Hz (see, e.g., FIG. 19, Frames J and L). Small adjustments in the water pressure in this range change the radii of the formed droplets, with lower water pressures generating smaller droplets. Eventually, at the lowest pressures the water stream retracts from the droplet extrusion region and droplet generation ceases.

When the relative oil and water pressures are approximately balanced (i.e., $P_w \sim P_o$) droplets begin to stack up against each other during the transition from the 30 µm channel in the droplet extrusion region to the wider 60 µm channel. As a result, the droplets form a "pearl necklace-like" configuration (see, e.g., FIG. 19, Frames D and I).

At water pressures that slightly exceed the oil pressure (i.e., $P_w > P_o$) the packing density of the droplets in the 60 µm channel increases. The first complex structure that emerges with increasing oil pressure is a compressed, single continuous stream of droplets that resembles a zipper (see, e.g., FIG. 19, Frames B and K). As the water pressure becomes moderately higher (e.g., $P_w \sim 10\%$ higher than $P_o$), polydisperse motifs appear as helices and patterned multi-layer ribbon structures (FIG. 19, Frames A and B). These patterns remain coherent as the arrayed droplets flow down the entire length of the channel from the droplet extrusion region to an outlet region, a distance of approximately 4 cm. At excessive water pressure, water fills the urethane channel as a solid stream, stripping the urethane channel of the surfactant coating and causing water to stick to the hydrophilic urethane walls of the channel.

Figure 20:
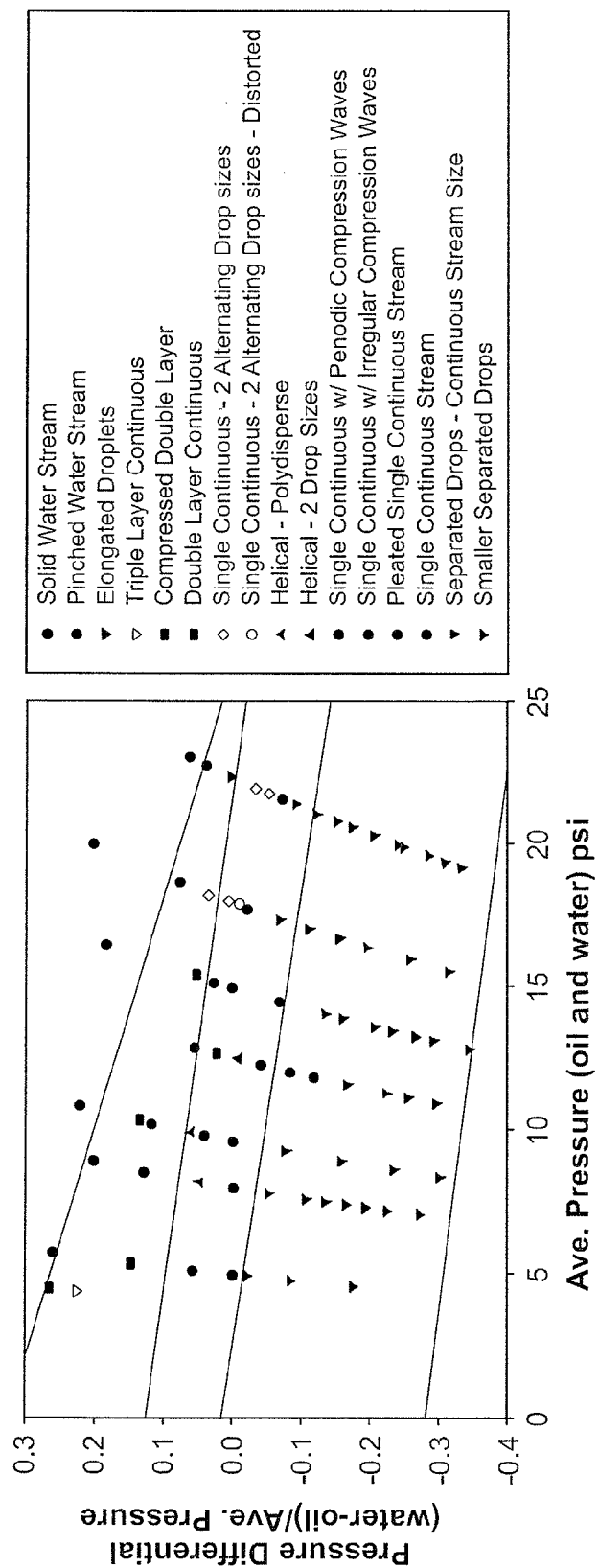
FIG. 20 is a phase diagram of the relationship between pressure and droplet pattern formation in the microfluidic device shown in FIG. 19.

As demonstrated above, the self-organization of droplets in the microfluidic devices of this invention depends on the differential pressure between the aqueous and oil-surfactant phases. Higher relative water pressures drive the formation of increasingly complex droplet arrays. This principle is demonstrated in FIG. 20, which provides a phase diagram indicating the relationship between pressure and droplet pattern formation in a microfluidic device having rounded contours. Higher water pressures give rise to increasingly complex droplet patterns.

Without being bound by any particular theory or mechanism of interaction, coherent droplet formation in a microfluidic device of this invention may be driven by at least two factors: (a) pressure fluctuations as aqueous fluid is sheared into an oil stream at a droplet extrusion region; and (b) the drag force of the droplets in the continuous fluid stream (e.g., of aqueous droplets in an oil stream). Thus, as an aqueous fluid breaks off into droplets at the droplet extrusion region, pressure in the oil stream fluctuates at a frequency based on the relative water and oil pressures. This pressure fluctuation manifests itself as a longitudinal pressure wave propagating in the direction of the flow stream. As the droplets transition from the narrow droplet extrusion region into the wider main channel, they slow down significantly relative to the oil stream. At higher frequencies, the droplets begin to collide and stack up into organized patterns at the transition between the narrow junction in the droplet extrusion region and the wider main channel. Complex structures form in rounded channels at high relative water pressures as colliding droplets are pushed from the center of the flow stream.

The size of a droplet in a microfluidic device of this invention may be provided by the equation:

$$r = \frac{\sigma}{\eta \varepsilon}$$

where r is the final droplet radius in a main channel. η, the viscosity of the continuous phase (e.g., the oil-surfactant phase in the above exemplary devices) and σ, the interfacial tension, may be obtained from values available in the art for the particular fluids used (see, for example, *CRC Handbook of*

*Chemistry and Physics*, CRC Press, Inc., Boca Raton, Fla., 2000). ∈, which denotes the shear rate, may be provided by the formula $$\varepsilon = \frac{2}{y_0} v,$$

where v is the velocity of the dispersed phase fluid (i.e., the droplets) and may be readily calibrated to the input pressures for a particular microfluidic device. $y_0$ denotes the radium of the inlet channel at the droplet extrusion region (i.e., the radius of the tapered channel 1606 in FIG. 16B)

Figure 21:
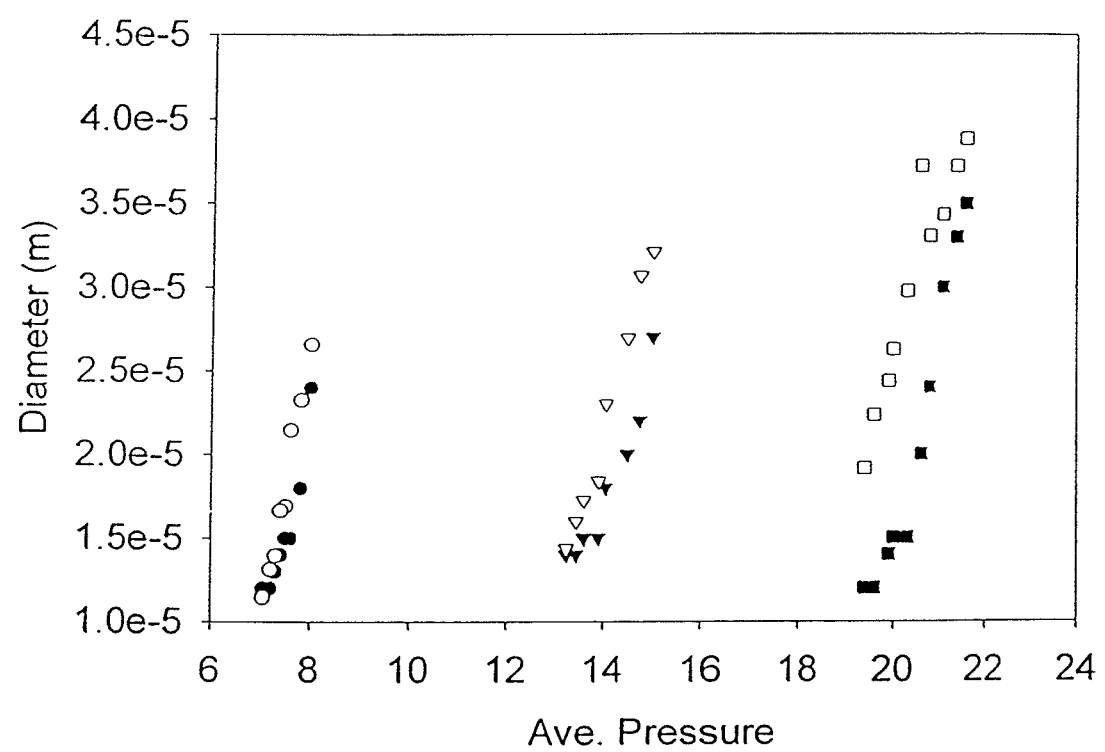
FIG. 21 is a plot showing measured droplet sizes in the microfluidic device shown in FIG. 19, and droplet sizes predicted by the formula $r = \sigma/\eta \in$ at different water/oil pressures. Open symbols (circles, triangles and squares) indicate droplet sizes predicted by the above formula, whereas closed symbols denote measured droplet radii at the corresponding pressures. Different symbols (circles, triangles or squares) denote experimental data sets acquired at different pressure settings.

The diagram provided in FIG. 21 compares droplet sizes predicted using the above equations (open symbols) to actual droplet sizes measured in the experiments described above (closed symbols). The different water/oil pressures used in these experiments are indicated on the horizontal axis. The different symbols (circles, triangles or squares) denote experimental data sets acquired at different pressure settings.

Droplet sizes calculated using the above equations are typically within a factor of about two from actual droplet radii measured in the above experiments. In preferred embodiments, the equations are used to determine or predict droplet sizes in a microfluidic device within a pressure range of 8.0-22.4 psi, or at droplet volume fractions (φ) that are less than about 0.635 (i.e., below the volume fraction of randomly packed spheres, as defined by Mason et al. (42). At higher water volume fractions (e.g., greater than about 0.635), multilayer droplet structures may form in the channels. The radii of these droplet structures are much smaller than the radii provided from the above equations. Droplets at such high volume fractions instead take forms of ribbons, "pearl necklaces" and other intermediate structures seen in FIG. 19. The structures maintain a surprisingly high degree of coherence, despite the fact that they are formed dynamically and far from an equilibrium state. Organized "crystal" structures of micelles have been previously observed in static systems, e.g., after formation by shearing plates (42). However, this example provides the first known demonstration of coherent structures of micelles in a dynamic (i.e., flowing) system of immiscible liquids.

EXAMPLE 13

Droplet Extrusion Regions

The invention provides embodiments of multi-phased devices which contain a plurality of droplet extrusion regions. The different droplet extrusion regions may each be connected to the same or different channels of the device. Embodiments where the different droplet extrusion regions are located along the main channel are preferred.

Figure 22:
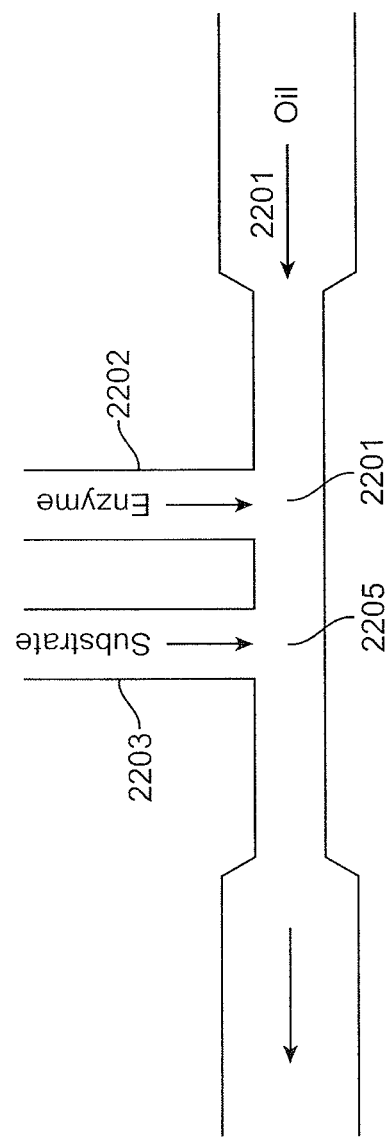
FIG. 22 shows an exemplary channel design for compartmentalization of Enzyme and Substrate.

An exemplary embodiment of such a device is illustrated in FIG. 22. The device comprises a main channel 2201 through which a pressurized stream or flow of a first fluid (e.g., oil) is passed, and two or more inlet channels 2202 and 2203 which intersect the main channel at droplet extrusion regions 2204 and 2205, respectively. Preferably, these inlet channels are parallel to each other and each intercept the main channel at a right angle. In specific embodiments wherein the droplets introduced through the different extrusion regions are mixed, the inlet channels are preferably close together along the main channel. For example, the main channel will typically have a diameter of 60 μm, that tapers to 30 μm at or near the droplet extrusion regions. The inlet channels also preferably have a diameter of about 30 μm and, in embodiments where droplet mixing is preferred, are separated by a distance along the main channel equal to approximately the diameter of the inlet channel (i.e., about 30 μm).

In the preferred embodiment illustrated in FIG. 22, the first inlet channel 2202 may introduce an aqueous solution containing an enzyme so that aqueous droplets containing molecules of the enzyme are introduced into the stream of oil in the main channel 2201. The second inlet channel 2203 may introduce an aqueous solution containing a substrate for the enzyme so that aqueous droplets containing molecules of the substrate are also introduced into the main channel 2201. In more detail, droplets containing the enzyme are first sheared off into the main channel 2201 at the first droplet extrusion region 2204. These droplets them move downstream, with the oil stream in the main channel, and pass through the second droplet extrusion region 2205. Droplet containing the substrate are also sheared off into the main channel, at the second droplet extrusion region. By timing release of these droplets to occur as a droplet of enzyme passes through the second droplet extrusion region, the two droplets are combined and the enzyme is able to react with the substrate.

Examples of enzymes that can be used in such a device include horseradish peroxidase and alkaline phosphatase, to name a few. Preferred substrates that can be introduced to react with these enzymes are ones which produce a detectable signal upon such a reaction; for example, substrates that release detectable dyes upon reacting with an enzyme. Specific examples include, but are not limited to, Dihydrorhodamine 123 and Amplex Red (which react with horseradish peroxidase), and p-nitrophenyl phosphate and fluorescein diphosphate (which react with alkaline phosphatase). Other enzymes and/or substrates can also be used and may be preferred for certain, particular applications.

Although the exemplary embodiment described here, and illustrated in FIG. 22, releases droplets of enzyme upstream from the droplets of substrate, droplets of the different fluid or solutions may be released in any order. Thus, for example, an aqueous solution containing a substrate may be released through the first inlet channel 2202 at the first droplet extrusion region 2204, and droplets of an aqueous solution containing an enzyme may be released through the second inlet channel 2203 at the second droplet extrusion region 2205.

EXAMPLE 14

Identification and Sorting of Viruses

One preferred embodiment is sorting viruses for identification, diagnostic or screening purposes. The viruses can be labeled directly via a fluorescent dye that intercalates into the nucleic acid or indirectly via a fluorescent antibody against a surface component of the virus as discussed in Example 5.

The another embodiment, the device of the invention can also be used to screen recombinant viruses to determine whether they exhibit targeted characteristics and therefore contain altered or improved genetic material.

In a particularly preferred embodiment, the devices and methods of the invention are used to sort and evaluate virus particles. The concentration (i.e., number) of virions in a droplet can influence sorting efficiently and therefore is preferably optimized. In particular, the sample concentration should be dilute enough that most of the droplets contain no more than a single virion, with only a small statistical chance that a droplet will contain two or more virions. This is to ensure that for the level of reporter measured in each droplet as it passes through the detection region corresponds to a single virion and not to two or more virions.

The microfluidic device provided by the invention comprises a main channel and at least one inlet region which is in communication with the main channel at a droplet extrusion region. The fluid which flows through the main channel can be a non-polar solvent, such as decane (e.g., tetradecane or hexadecane) or another oil; and the fluid which passes through the inlet region can be an aqueous solution, for example ultra pure water, TE buffer, phosphate buffer saline and acetate buffer or any solution capable of sustaining viruses. The aqueous solution preferably contains viral particles fix analysis or sorting in the device.

In preferred embodiments, the droplet extrusion region comprises a T-shaped junction between the inlet region and the main channel, so that the aqueous solution containing the virus particles enters the main channel at an angle perpendicular to the flow of fluid through the main channel, and is sheared off into the flow of the non-polar solvent.

The invention also provides a device for sorting viruses comprising: (a) a microfabricated substrate; a detection region; and a flow control region. In more detail, the microfabricated substrate has at least one main channel, an inlet which meets the main channel at a droplet extrusion region, and at least two branch channels meeting at a junction downstream from the droplet extrusion region. The detection region of the device is within or coincident with at least a portion of the main channel, and is also associated with a detector. The flow control system of the device is responsive to the detector and is adapted to direct the viral particles into a branch channel for sorting and analysis.

The invention is also suitable for high throughout or combinatorial screening. High throughout screening (HTS) here includes, for example, screening about $10^6$ to $10^7$ or even $10^{12}$ to $10^{13}$ members of a library, for example a protein library. Libraries of this kind can result, for example, when all permutations of one or more mutations in a protein having 300 amino acids are generated. According to one embodiment of the invention, library members are encapsulated randomly in droplets, e.g. about 100-1000 proteins per droplet. The droplets are then sorted for a detectable characteristic, and those which meet the criteria can be isolated, enriched, and resorted in cyclical fashion to obtain the desired proteins. It will be appreciated that the HTS embodiments of the invention are not limited to proteins: any detectable particle or material can be screened.

BIBLIOGRAPHY

1. P. J. Crosland-Taylor, *Nature (London)* 171, 37 (1953).
2. U.S. Pat. No. 2,656,508 issued to Coulter (1949).
3. L. A. Kamensky, M. R. Melamed, H. Delman, *Science* 150, 630 (1965).
4. A. Moldavan, *Science* 80, 188 (1934).
5. M. A. Van Villa, T. T. Trujillo, P. F. Mullaney, *Science* 163, 1213 (1969).
6. M. A. Van Villa, et al., *A fluorescent cell photometer: a new method for the rapid measurement of biological cells stained with fluorescent dyes*. (Biological and Medical Research Group of the Health Division, LASL., 1997).
7. M. J. Fulwyer, *Science* 156, 910 (1974).
8. H. M. Shapiro, *Practical Flow Cytometry* (Wiley-Liss Inc., New York City, 1995).
9. M. R. Melamed, T. Lindmo, M. L. Mendelsohn, *Flow Cytometry and Sorting* (Wiley-Liss Inc., New York City, 1990).
10. P. H. Li, D. J. Harrison, *Analytical Chemistry* 69, 1564 (1997).
11. S. Fiedler, et al. *Analytical Chemistry* 70, 1909-1915 (1998).
12. H. P. Chou, A. Scherer, C. Spence, S. R. Quake, Proc. Natl. Acad. Sci. USA 96: 11-13 (1998).
13. M. U. Kopp et al., *Science,* 280: 1046 (1998).
14. A. Ashkin, J. M. Dziedzic, *Science* 235, 1517 (1987).
15. A. Ashkin, J. M. Dziedzic, *Nature* 330, 769 (1987).
16. T. N. Buican, M. J. Smyth, H. A. Verissman, *Applied Optics* 26, 5311 (1987).
17. C. Spence, S. R. Quake, "Transformation of cells with DNA sorting on microchips."; personal communication, 1998.
18. D. J. Harrison et al., *Science,* 261: 895 (1993)
19. G. Whitesides, Y. Xia, *Angewandte Chemie International Edition* 37, 550 (1998).
20. J. P. Brody, "Valveless Microswitch, U.S. Pat. No. 5,656, 155 (1998).
21. Benecke et al., U.S. Pat. No. 5,454,472 (1995).
22. Angell et al., Scientific American 248:44-55 (1983).
23. Manz et al., Trends in Analytical Chemistry 10: 144-149 (1991).
24. Thompson, L. F., "Introduction to Lithography", ACS Symposium Series 219:1-13, (1983).
25. Krutenat, R. C., Kirk-Othmer Concise Encyclopedia of Chemical Technology, John Wiley & Sons, New York (1985).
26. Ballantyne, J. P., et al., J. Vac. Sci. Technol. 10:1094 (1973).
27. Stemmer, W. P. C. Nature, 370, 389 (1994).
28. Aine, H. E., et al., U.S. Pat. No. 4,585,209 (1986).
29. Bein, Thomas, Efficient Assays for Combinatorial Methods for the Discovery of Catalysts, Angew. Chem. Int. Ed. 38:3, 323-26 (1999).
30. Tawfik, D. and Griffiths, A. *Nat. Biotechnol.* 16, 656 (1998).
31. Sambrook et al., *Molecular Cloning: A Laboratory Manual $2^{nd}$ Edition*, Cold Spring Harbor Laboratory Press (1989).
32. Baker, D. R., in Capillary Electrophoresis, John Wiley Sons, New York, 1995.
33. Haugland, R. P., in Handbook of Fluorescent Probes and Research Chemicals, 5th Ed., Molecular Probes, Inc., Eugene, Oreg. (1992).
34. J. Affholter and F. Arnold, "Engineering a Revolution," *Chemistry in Britain*, April 1999, p. 48.
35. H. Joo, Z. Lin and F. Arnold, "Laboratory evolution of peroxide-mediated cytochrome P450 hydroxylation," *Nature* 399, 670 (1999).
36. R. V. Hare, "Polyvinylsiloxane impression material."; U.S. Pat. No. 5,661,222, 1997.
37. Inoue, Shinya and Spring, Kenneth R., Video Microscopy: The Fundamentals, 2nd ed., Plenum Press, New York, N.Y. (1997).
38. Harrison et al., International Publication No. 98/52691, published Nov. 26, 1998.
39. Langmuir 2000, 16, 347-51.
40. Gravesen, P., et: al., U.S. Pat. No. 5,452,878 (1995).
41. Wise, K. D., et al., U.S. Pat. No. 5,417,235 (1995).
42. Mason, T. J. and Bibette, J. "Shear Rupturing of Droplets in Complex Fluids", *Langmuir,* 13, 4600-4613.

What is claimed is:

1. A method of making droplets in a microfluidic device, comprising flowing an extrusion fluid through a first inlet channel while flowing a sample fluid through a second inlet channel, wherein the first and second inlet channels have diameters between about 2 and 100 microns or cross-sectional dimensions in the range of 1 to 100 microns;

wherein the first and second inlet channels are in fluidic communication at a junction;

wherein the second inlet channel is tapered towards the junction, wherein the sample fluid is immiscible with the extrusion fluid, and wherein the junction is constructed and arranged so that sample fluid droplets are introduced into the extrusion fluid.

2. The method of claim 1, wherein the first inlet channel is tapered towards the junction.

3. The method of claim 2, wherein the first channel and the second channel have substantially the same diameters at the junction.

4. The method of claim 1, wherein the second channel is tapered along a distance that is about the width of the channel before it is tapered minus the width of the channel after it is tapered, divided by two.

5. The method of claim 1, wherein the second channel is tapered at an angle of about 45 degrees.

6. The method of claim 1, wherein: the sample fluid is an aqueous solution and the extrusion fluid is a non-polar solvent.

7. The method of claim 1, wherein at the junction, the sample fluid flows at a pressure that is higher than that of the extrusion fluid.

8. The method of claim 1, wherein the sample fluid is introduced into the extrusion fluid as single monodisperse droplets.

9. The method of claim 1, wherein the droplets are introduced into the extrusion fluid with regular periodicity.

10. The method of claim 9, wherein the droplets are formed at a frequency of about 20 to 80 Hz.

11. The method of claim 1, wherein the first inlet channel and the second inlet channel form a junction at an angle of about 60 to about 120 degrees.

12. The method of claim 1, wherein the sample fluid droplets contain a biological material.

13. The method of claim 1, wherein the sample fluid droplets contain a polynucleotide or an enzyme or both.

14. The method of claim 1, wherein the sample fluid droplets contain a reporter molecule.

15. The method of claim 14, wherein the reporter molecule is a fluorescent agent.

16. The method of claim 1, further comprising detecting signal produced by a chemical reaction of a substrate catalyzed by an enzyme in the sample fluid droplets.

17. The method of claim 1, further comprising detecting signal produced by a polymerase chain reaction in the sample fluid droplets.

18. A method of making droplets in a microfluidic device, comprising flowing an extrusion fluid through a first inlet channel while flowing an aqueous fluid through a second inlet channel, wherein the first and second inlet channels have cross-sectional dimensions in the range of 1 to 100 microns;

wherein the first and second inlet channels are in fluidic communication at a junction;

wherein the second inlet channel has a diameter that is narrower at the junction than before the junction, wherein the aqueous fluid is immiscible with the extrusion fluid, and wherein the junction is constructed and arranged so that aqueous fluid droplets are introduced into the extrusion fluid.

19. The method of claim 18, wherein the first channel and the second channel have substantially the same diameters at the junction.

20. The method of claim 19, wherein the first inlet channel and the second inlet channel form a junction at an angle of 90 degrees.

21. A microfluidic product comprising a first inlet channel and a second inlet channel that are in fluid communication at a junction, wherein the second inlet channel is connected to a source of sample fluid and the first inlet channel is connected to a source of extrusion fluid that is immiscible with the sample fluid;

wherein the first and second inlet channels have a diameter in the range of 2 to 100 microns or cross-sectional dimensions in the range of 1 to 100 microns;

wherein the second inlet channel is tapered towards the junction;

wherein the junction is configured such that when a sample fluid is flowed through the second channel while an extrusion fluid that is immiscible with the sample fluid is flowed through the first channel, droplets of the sample fluid are introduced into the extrusion fluid.

22. The microfluidic product of claim 21, wherein the first inlet channel and the second inlet channel form a junction at an angle of about 60 to about 120 degrees.

23. The microfluidic product of claim 22, wherein the first inlet channel and the second inlet channel form a junction at an angle of 90 degrees.

24. The microfluidic product of claim 21 wherein the first inlet channel is tapered towards the junction.

25. The microfluidic product of claim 21, wherein the first channel and the second channel have substantially the same diameters at the junction.

26. The microfluidic product of claim 21, wherein the second channel is about 30 microns in diameter at the junction.

27. A method for manufacturing a product according to claim 21, comprising:

forming the first inlet channel, the second inlet channel, and the junction in an elastomer chip; then connecting the second inlet channel to a source of sample fluid and connecting the second input channel to a source of extrusion fluid.

* * * * *